us 
US007176005B2

(12) United States Patent
Melis et al.

(10) Patent No.: US 7,176,005 B2
(45) Date of Patent: Feb. 13, 2007

(54) MODULATION OF SULFATE PERMEASE FOR PHOTOSYNTHETIC HYDROGEN PRODUCTION

(75) Inventors: Anastasios Melis, El Cerrito, CA (US); Hsu-Ching Chen Wintz, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 10/762,769

(22) Filed: Jan. 21, 2004

(65) Prior Publication Data

US 2005/0014239 A1 Jan. 20, 2005

Related U.S. Application Data

(63) Continuation-in-part of application No. 10/350,298, filed on Jan. 22, 2003.

(60) Provisional application No. 60/377,902, filed on May 2, 2002, provisional application No. 60/354,760, filed on Feb. 4, 2002.

(51) Int. Cl.
  *C12P 3/00* (2006.01)
  *C12N 1/12* (2006.01)
  *C12N 9/00* (2006.01)
  *C12N 15/09* (2006.01)
  *C12N 15/00* (2006.01)
  *C12N 15/74* (2006.01)
  *C07H 21/04* (2006.01)

(52) U.S. Cl. ............... 435/168; 435/69.2; 435/183; 435/257.2; 435/320.1; 435/440; 435/471; 536/23.2; 536/24.5

(58) Field of Classification Search ............. 435/320.1, 435/252.1, 419, 183, 440, 168, 69.2, 257.2, 435/471; 536/24.5, 23.2
See application file for complete search history.

(56) References Cited

U.S. PATENT DOCUMENTS

| 4,442,211 | A | | 4/1984 | Greenbaum |
| 4,532,210 | A | * | 7/1985 | Miura et al. ............... 435/168 |
| 5,871,952 | A | | 2/1999 | Ghirardi et al. |
| 6,395,521 | B1 | | 5/2002 | Miura |
| 6,696,292 | B1 | * | 2/2004 | Allen et al. ............... 435/419 |
| 2001/0053543 | A1 | | 12/2001 | Anastasios et al. |

OTHER PUBLICATIONS

Ghirardi et al., Microalgae: a green source of renewable hydrogen. TIBTECH., 18: 506-511, 2000.*
Chen et al., "A Nuclear encoded chloroplast sulfate permease from *Chlamydomones reinhardtii*: application in $H_s$ production". Dept. of Plant and Microb, UC Berkeley (Oct. 22, 2002) (Abstract).

Ghirardi et al., "Microalgae: a green source of renewable $H_x$" *Trends Biotechnol.* 12:506-511 (Dec. 2000).
Happe et al., "Differential regulation of the Fe-hydrogenase during anaerobic adaptation in the green alga *Chlamydomonas reinhardtii*," *Eur. J. Biochem.* 269:1022-1032 (2002).
Melis et al., Properties of $H_x$-production in *Chlamydomonas reinhardtii*, Plant and Microbiology, University of California, (Oct. 29, 2002) (Abstract).
Melis et al., "Hydrogen Production. Green Algae as a Source of Energy" *Plant Physiology* 127:740-748 (Nov. 2001).
Melis et al., "Sustained Photobiological Hydrogen Gas Production upon Reversible Inactivation of Oxygen Evolution in the Green Alga *Chlamydomonas reinhardtii*," *Plant Physiology*, 122:127-135 (Jan. 2000).
Zhang et al., "Biochemical and morphological characterization of sulfur-deprived and $H_x$-producing *Chlamydomonas reinhardtii* (green alga)," Springer-Verlag (2001) (Abstract).
Goodsell, David S., Rubisco (Ribulose Bisphosphate Carboxylase/Oxygenase) Protein Data Bank, Molecule of the Month (Oct. 23, 2002).
Chen et al., "*SulP*, a nuclear gene encoding a putative chloroplast-targeted sulfate permease in *Chlamydomonas reinhardtii*" *Planta* 218:98-106 (2003).
Chen et al., "*Chlamydomonas reinhardtii* chloroplast sulfate transport system permease (SulP) gene, complete cds; nuclear gene for chloropladsst product." Database EMBL XP002368676, accession No. AF 467891 (Feb. 6, 2002).
Chen et al., "*Chlamydomonas reindardtii* chloroplast sulfate transport system permease (SulP) gene, complete cds; nuclear gene for chloroplast product." Database EMBL XP002368677 accession No. AF481828 (Mar. 13, 2002).
Chen et al., "Chloroplast sulfate transport system permease" Database EMBL XP002368678 accession No. Q8RVC7 (Jun. 1, 2002).
Chen et al., "Role of *SulP*, a nuclear-encoded chloroplast sulfate permease, in sulfate transport and $H_2$ evolution in *Chlamydomonas reinhardtii*" *Photosynthesis Research*, 84:289-296 (2005).
Davies et al., "Mutants of *Chlamydomonas* with Aberrant Responses to Sulfur Deprivation" *The Plant Cell*, 6:53-63 (Jan. 1994).
Turmel et al., "The complete chloroplast DNA sequence of the green alga *Nephroselmis olivacea*: Insights into the architecture of ancestral chloroplast genomes" *Proc. Natl. Acad. Sci. USA* 96:10248-10253 (Aug. 1999).
Yildiz et al., "Characterization of Sulfate Transport in *Chlamydomonas reinhardtii* during Sulfur-Limited and Sulfur-Sufficient Growth" *Plant Physiol.* 104:971-987 (1994).

* cited by examiner

*Primary Examiner*—Rebecca E. Prouty
*Assistant Examiner*—Ganapathirama Raghu
(74) *Attorney, Agent, or Firm*—Karl Bozicevic; Bozicevic, Field & Francis LLP

(57) ABSTRACT

Sustained hydrogen production is obtained by the culturing of a genetically-modified algae, where the ability of the chloroplasts to intake sulfate is reduced or eliminated compared to wild-type algae. The alga is cultured in a sealed environment in a liquid or solid medium that contains sulfur, and hydrogen is generated continuously. Alternatively, the algae may be cultured in the presence of bacteria that also produce hydrogen gas. The hydrogen produced can be collected and used as a clean energy source.

5 Claims, 29 Drawing Sheets

FIG. 2

*Chlamydomonas reinhardtii* chloroplast Sulfate Permease (*SulP*) gene structure

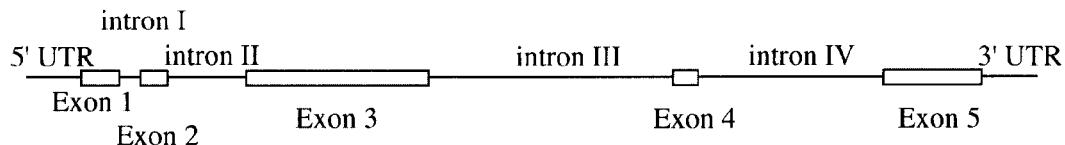

FIG. 3

*reinhardtii* chloroplast Sulfate Permease *(SulP)* amino acid sequence

MERVCSHQLASSRGRPCIAGVQRSPIRLGTSSVAHVQVSPAGLGRYQRQRLQVVASAAAA
AAFDPPGGVSAGFSQPQQQLPQQHPRQPQAVAEVAVAESVSAPASAAPSNDGSPTASMDG
GPSSGLSAVPAAATATDLFSAAARLRLPNLSPIITWTFMLSYMAFMLIMPITALLQKASL
VPLNVFIARATEPVAMHAYYVTFSCSLIAAAINCVFGFVLAWVLVRYNFAGKKILDAAVD
LPFALPTSVAGLTLATVYGDEFFIGQFLQAQGVQVVFTRLGVVIAMIFVSFPFVVRTMQP
VMQEIQKEMEEAAWSLGASQWRTFTDVVLPPLLPALLTGTALAFSRALGEFGSIVIVSSN
FAFKDLIAPVLIFQCLEQYDYVGATVIGTVLLLISLVMMLAVNQLQKLARK* (SEQ ID NO:1)

FIG. 4A

Coding sequence of CrcpSulP
5' UTR:173 bp, Exon1: 124 bp, intronI: 77 bp, Exon2: 78 bp,
intronII: 279 bp Exon3: 620 bp, intronIII: 834 bp,
Exon4: 87 bp, intronIV: 699 bp, Exon5: 327 bp, 3'UTR: 575 bp Total length: 3873 bp

```
gcttagtacc taagcaaaaa taccaaagcc ttatcctgag ttgtcaacaa gaactccagc   60
ctgcgacgat gcaaagcctt tcttgagcgg gttgatggac tttgctttgt tatctgtcca  120
gtaagccacc agacactacc aagtagagta atccatttgt ataggtacag aatatggagc  180
gagtttgcag ccatcagctt gcctcgtcgc gagggaggcc atgcatcgct ggggtgcagc  240
ggtcgcccat ccgactaggg acttcaagcg ttgctcatgt gcaggtctct ccggcaggta  300
agcaccgcgc tcggcggcgt gtacacatgg ggccgtcagg ccaactgcgt ttgttggcta  360
tgcaaccgaa acaggccttg ggagatatca acggcaaaga ctgcaagtcg tggcgtctgc  420
agctgcggca gcggctttcg accctcctgg aggtgcgtgg cgtgagggct gcacgggtgc  480
gggttggcct ggaaaccaag cctcgccacg actacctgca acagcattgc ccgcatctcc  540
agcccctcac cctcgagtgc ctcccgaaga cctctatccc ctgcgcatca ttggttcggg  600
ggcgccgcct gcgggccttg ggcgctggct acgctgaccg cacggcacga cttggcacgg  660
cctggcgcgg cctgagcggc cccccccctc ctgatggccc cacgctttgc cgcccacgcc  720
gctcccgca ggtgtctccg ccgggttctc gcagccgcaa cagcagctgc cacaacagca  780
cccacgccaa ccacaggcgg tggcggaggt agctgtcgcc gagtcagtct cggcgcccgc  840
ttctgcggcg ccctccaatg atggctcgcc cacggcctcc atggacggcg gcccagctc  900
cggcctcagc gccgtgcccg ccgccgccac cgccaccgac ctcttctccg ccgcggcgcg  960
cctccgcctg cccaacctct cccccatcat cacctggacc ttcatgctct cctacatggc 1020
cttcatgctc atcatgccca tcaccgcgct gctgcaaaaa gcctcgctcg tgccgctcaa 1080
cgtcttcatc gcgcgcgcca ccgagccggt ggcgatgcac gcctactacg tcaccttctc 1140
ctgctcgctg atcgcggccg ccatcaactg cgtgtttggc ttcgtgctgg cctgggtgct 1200
ggtgcgctac aatttcgcgg ggaagaagat cctggacgcg gcggtggacc tgccgttcgc 1260
gctgccgacc tcggtggcgg gcctcacgct tgccacggtg tacggcgacg agttcttcat 1320
cggccagttc ctgcaggcgc agggcgtgca ggtgcgtgcg tatagcatag tggagtgtgg 1380
ttagcagctg ggggtccggc agtagttccc gccctagtga ggtcgaaact ataccagaag 1440
aagaggacga acatggggct atccagcaag ctcgtctagg gaaggaggag tttgggagaa 1500
cggtggggtg ggagggagag ggagggcgtt ggctgggagg gaagggtaag gcgggaggga 1560
gatggtagca cggggcgttg gggacgcaga aggatgacag gcggctgcag ggaagggatg 1620
gggaagcgga gctggggaca gtgcgaagag ccgggagaga ggggaagttt gagtcaggaa 1680
gaggggctag agaggggcat gcggactcct gctgggattt aggtgcgtgc tcattgagga 1740
gcccttggaa tcagcggacg gaaacgtggc cgacgggtc tgccgagcac accaggctag 1800
ctagacgcgc ggttgggcaa cgagcagagc tgctgtgcgg ctatggatgg aaggcgatgc 1860
agcgagcatg tgcagtgaac attggtttga ggacagggga ctccgaggtt gcataggcgg 1920
gccgccactg tctctgccgc tagggtgact agctgcctcg aacctggcgg tggccccata 1980
cccgcagttg gaggatgctc cacgcgcttc agcttgccat gtctggggtc tgggtctgga 2040
cgcaatcagc gtgtgagggt ccaactctat atggaattat ggatacctc caactaccag 2100
cacgtaggct gccggaacgc ggctgaagcg gctggcctgc ccctcatcc tctcgttccc 2160
```

FIG. 4B

```
ctgttttgt  ccctgtcca  cccaggtggt  gttcacgcgg  ctgggtgtgg  tgatcgccat  2220
gatcttcgtg  tccttcccct  tcgtggtgcg  caccatgcag  cccgtcatgc  aggtgagagc  2280
gcccaggagg  cggagccatg  gcgggttggg  gcgggttggg  gcgggttggg  gcggggcgcg  2340
gatggggcgg  cttggggagt  aatgtgggc   ggatggggtg  gcagcctggc  agggtatggg  2400
agcgagagga  tagcggggac  aggggacagg  gaagggaagg  gaaggggaag  gatgccctat  2460
gcgagcaaag  ggggtatggg  aaccggcggt  tggggctggg  agcgacggga  gcagggaggg  2520
agtgcacgga  acggggcaa   ggcggacagg  gtgagggagg  gtgcaggccg  gactgggatg  2580
ggtcatgtgt  cctggtcggg  ggtgtagccg  tgggaggcgg  gcaggcagcg  tgtgttctgg  2640
cacggtgttt  tggcgaaaga  taccacggca  tggtatgggg  ccagttgggc  agggaagaac  2700
cgttggacac  gacttcgttg  acagatctag  ttcattgcac  ccgggtcgca  ccaagggtgg  2760
cggcgagccc  ggcccggcac  gtccgagtac  cccggagccg  taacgccgca  acccgccttg  2820
ttgcgcccct  tccctgctcc  cctgctccgc  ataccgtgca  ccatgccctc  tgccgccccc  2880
tcaggccctc  aggccctcac  ctccccctca  cctcctccta  acgccttccc  ctcgccttcc  2940
cttcccctcc  caacgccacc  acgtgcaaca  ggaaatccaa  aaggagatgg  aggaggcggc  3000
atggtcgctg  ggcgcctcgc  agtggcgcac  cttcacagac  gtggtgctgc  cgccgctgct  3060
gcccgcgctg  ctgaccggca  cggcactggc  cttctcgcgc  gcgcttggcg  agttcggatc  3120
cattgtcatc  gtgtcctcca  actttgcctt  caaggacctg  atcgcgcccg  tgctgatctt  3180
ccagtgcctg  gagcagtacg  actacgtggg  cgccaccgtg  atcggcacag  tactgctgtt  3240
gatttcgctg  gtgatgatgt  tggcggtgaa  ccagctgcag  aagctggcgc  gcaagtgagg  3300
ggctgaggcg  tttgaggaga  gtgggcgtct  gcggaggcgc  ttgtggcgca  ggggcaggtg  3360
gaggaggttg  cagggtgagg  caggagtggc  aggtggtgga  gggtgcaggg  cggggtgttg  3420
ggatgggatg  ggatgggacc  gtgggagggg  tgggactttg  ggtgggtggg  agtgggtgct  3480
acgtattagg  atatgggagg  tggtatgcag  ttgaaggggg  gggtggcaat  ctggacgggg  3540
actcactgtt  tactaggcac  gcatgtcgca  ggagtggata  tcgatgggtg  tggggatgtc  3600
agcacgcttg  gcttgagttg  ggccatggga  cccgggacta  ggcttggttg  cgagccgagc  3660
cagtcaccag  ggagacgtac  gagcgcacac  agtgattacg  gggattgatt  aggcggcgaa  3720
ttgacgcaaa  tccacggggg  ctgtggcttg  ggggaggcag  ggattgagcg  aaggacgcac  3780
tgcaagctca  ggcagtcgca  tgcccgtacc  ctgcttctgg  tccagtgtgg  agacaagact  3840
ggcaatcgtg  gtcctttgca  attcatggcg  cgc  (SEQ ID NO:2)
```

FIG. 5

Full length cDNA sequence of *CrcpSulP*: 1984 bp

```
gcttagtacc taagcaaaaa taccaaagcc ttatcctgag ttgtcaacaa gaactccagc   60
ctgcgacgat gcaaagcctt tcttgagcgg gttgatggac tttgctttgt tatctgtcca  120
gtaagccacc agacactacc aagtagagta atccatttgt ataggtacag aatatggagc  180
gagtttgcag ccatcagctt gcctcgtcgc gagggaggcc atgcatcgct ggggtgcagc  240
ggtcgcccat ccgactaggg acttcaagcg ttgctcatgt gcaggtctct ccggcaggcc  300
ttgggagata tcaacggcaa agactgcaag tcgtggcgtc tgcagctgcg gcagcggctt  360
tcgaccctcc tggaggtgtc tccgccgggt tctcgcagcc gcaacagcag ctgccacaac  420
agcacccacg ccaaccacag gcggtggcgg aggtagctgt cgccgagtca gtctcggcgc  480
ccgcttctgc ggcgccctcc aatgatggct cgcccacggc ctccatggac ggcggcccca  540
gctccggcct cagcgccgtg cccgccgccg ccaccgccac cgacctcttc tccgccgcgg  600
cgcgcctccg cctgcccaac ctctccccca tcatcacctg gaccttcatg ctctcctaca  660
tggccttcat gctcatcatg cccatcaccg cgctgctgca aaaagcctcg ctcgtgccgc  720
tcaacgtctt catcgcgcgc gccaccgagc cggtggcgat gcacgcctac tacgtcacct  780
tctcctgctc gctgatcgcg gccgccatca actgcgtgtt tggcttcgtg ctggcctggg  840
tgctggtgcg ctacaatttc gcggggaaga agatcctgga cgcggcggtg gacctgccgt  900
tcgcgctgcc gacctcggtg gcgggcctca cgcttgccac ggtgtacggc gacgagttct  960
tcatcggcca gttcctgcag gcgcagggcg tgcaggtggt gttcacgcgg ctgggtgtgg 1020
tgatcgccat gatcttcgtg tccttcccct tcgtggtgcg caccatgcag cccgtcatgc 1080
aggaaatcca aaaggagatg gaggaggcgg catggtcgct gggcgcctcg cagtggcgca 1140
ccttcacaga cgtggtgctg ccgccgctgc tgcccgcgct gctgaccggc acggcactgg 1200
ccttctcgcg cgcgcttggc gagttcggat ccattgtcat cgtgtcctcc aactttgcct 1260
tcaaggacct gatcgcgccc gtgctgatct tccagtgcct ggagcagtac gactacgtgg 1320
gcgccaccgt gatcggcaca gtactgctgt tgatttcgct ggtgatgatg ttggcggtga 1380
accagctgca gaagctggcg cgcaagtgag gggctgaggc gtttgaggag agtgggcgtc 1440
tgcggaggcg cttgtggcgc aggggcaggt ggaggaggtt gcagggtgag gcaggagtgg 1500
caggtggtgg agggtgcagg gcggggtgtt gggatgggat gggatgggac cgtgggaggg 1560
gtgggacttt gggtggggtgg gagtgggtgc tacgtattag gatatgggag gtggtatgca 1620
gttgaagggg ggggtggcaa tctggacggg gactcactgt ttactaggca cgcatgtcgc 1680
aggagtggat atcgatgggt gtggggatgt cagcacgctt ggcttgagtt gggccatggg 1740
acccgggact aggcttggtt gcgagccgag ccagtcacca gggagacgta cgagcgcaca 1800
cagtgattac ggggattgat taggcggcga attgacgcaa atccacgggg gctgtggctt 1860
gggggaggca gggattgagc gaaggacgca ctgcaagctc aggcagtcgc atgcccgtac 1920
cctgcttctg gtccagtgtg gagacaagac tggcaatcgt ggtcctttgc aattcatggc 1980
gcgc                                                              1984
```
(SEQ ID NO: 3)

FIG. 8A

```
Nephroselmis    ------------------------------------------------------------
Mesostigma      MERVCSHQLASSRGRPCIAGVQRSPIRLGTSSVAHVQVSPAGLGRYQRQRLQVVASAAAA  60
Chlamydomonas   ------------------------------------------------------------
Chlorella       ------------------------------------------------------------
Syn.PCC7942     ------------------------------------------------------------
Marchantia      ------------------------------------------------------------
Bacillus        ------------------------------------------------------------

Nephroselmis    ---------------------------------------------------MFDPKSLD-   8
Mesostigma      ------------------------------------------------------MN---   2
Chlamydomonas   AAFDPPGGVSAGFSQPQQQLPQQHPRQPQAVAEVAVAESVSAPASAAPSNDGSPTASMDG 120
Chlorella       ------------------------------------------------------------
Syn.PCC7942     --------------------------------------------------MSLR-----   4
Marchantia      ------------------------------------------------------MIPLFFIP-   8
Bacillus        -------------------------------------------------------MKSVR-   5

Nephroselmis    ---------SGSRSILTMKNRLVSWAWALTLMYMLVSLILPIGALLQKSSQ            50
Mesostigma      ------------YFSK----LSCSWRITLGYLLFMLILPILALLSRASQL            35
Chlamydomonas   GPSSGLSAVPAAATATDLFSAAAARLRLPNLSPIITWTFMLSYMAFMLIMPITALLQKASL 180
Chlorella       ---------------------MKRYPTFIKNSILLFYFFLLILPVVVLFLIFQ         34
Syn.PCC7942     -------------LPSLSFTWLTR---LSWSWRFTWVYLTLILFTPIIALFLKSAS      44
Marchantia      ---------PFIILFITKGKFRFLT-KFELVLACALHYGTFILALPIEFLLYKTKQ       54
Bacillus        -----------SWKNHNILPG--FGLSLGFTMYLGILVLLPLSMVFINTSS           44
                                         .      *                   *: :

Nephroselmis    ESVSEFVSIATAPVAMSAYAVTLSSALIAALLNGVFGLLIAWVLVRYEFPGRRLLDAAVD   110
Mesostigma      ELFSNFWSIAMEPAAIYAYSITLSMALIASIVNGIFGIFIAWILVRYNFPGKRIVDAAID    95
Chlamydomonas   VPLNVFIARATEPDPIAVSAYLLTVQMAFYAALVNSIEGFIITWVLVRYQFWGREFLDAAVD 240
Chlorella       NNWHEVLRKATDPIAVSAYLLTVQMAFYAALVNSIEGFIITWVLVRYQFWGREFLDAAVD   94
Syn.PCC7942     LPLGRIWELATOPVAVAAYEVTFGLSLAAALATIINAIFGLILAWVLVRYDFPGKKLFDSFID  104
Marchantia      QPWNILLQTALEPVVLSAYGFTELTALLATIINAIFGLILAWVLVRYEFPGKKLLDATVD   114
Bacillus        MGWQAFWQAITEPRVLASYRLSFGAAITAASINAVFGLLIAWLVRYHFPGKRIIDGLVD   104
                                    :  .   :     .  :  . :**::**::**::** . :.
```

FIG. 8A CONT.

```
Nephroselmis     LPFALPTSVAGLTLATVYSDQGWIGTWLSSLNIQVAFTRLGVMLAMLFVSFPFVVRTLQP   170
Mesostigma       LPFALPTSVAGLTLATVYSEKGWIGHFLQSLSIKVVFTKLGVGVAMIFVSFPFVVRTLQP   155
Chlamydomonas    LPFALPTSVAGLTLATVYGDEFFIGQFLQAQGVQVVFTRLGVVIAMIFVSFPFVVRTMQP   300
Chlorella        LPFALPTSVAGLTLATVYGDQGWIGSLFNLEGFLQAFPFGVVLLAMIFVSLPFVVRTLQP   154
Syn.PCC7942      LPFALPTAVAGLTLATVYSDKGWIGQFIAPFGVQIAFTRWGVLLAMIFISLPFVVRTVEP   174
Marchantia       LPFALPTAVAGIALTTLYTTNGWIGQYLEVFGIRIAFTPLGVIVALTFIGLPFVVRMVQP   164
Bacillus         *:*****:*** ..*      :*: .    : :   : *.*: *::** :***:   *

Nephroselmis     VLQQDMERELEEAAWSLGASPFNTFLRVLCPPLMPAMMTGIALAFSRAVGEYGSVVIVSGN   230
Mesostigma       VLQDIEKELEEAAWSLGASSWTTFFWKVIFPSLLIPSLLTGIALAFSRAVGEYGSVVIASN   215
Chlamydomonas    VMQEIQKEMEEAAWSLGASQWRTFTFTDVVLPPLLTWPALFTGFTLSFSRALGEFGSIVIVSSN   360
Chlorella        VLQEMEKSLEEAAWSLGASSWETFRKVILPTLWPALFTGVLAGVAQGFSRAVGEFGSVVIISGN   214
Syn.PCC7942      LLELEVEAEEAAASLGASPSETFWRVILPPILPGVLAGVAQGFSRAVGEYGSIVLIASN   224
Marchantia       VLQNMEEDLEEAAWCLGASPWITFWHILFPPLTPSLLTGTTLGFSRALGEFALAFARALGEYGSIVLIASN   234
Bacillus         VLQGIEKELEEASACLGANRLQTFSKIIFPTVLPALLTGFALAFARALGEYGSVVFISGN   224
                 : . : ...:**:: ****          :: ** :  ::**  *  ***.  . :

Nephroselmis     IPFQDLIAPVLIFQRLEQYDYSGATVIGTVVLLISLTLLLAINWIQASNRKFLG-     284
Mesostigma       IPFKDLTAPVLIFQKLEQYDYTGATVIGTVILSLFILVGINIIQSLNQMYSK---     269
Chlamydomonas    FAFKDLIAPVLIFQCLEQYDYCGATVIGTVLLLIVMMLAVNQLQKLARK------     411
Chlorella        LPFKDLVASVLIYQSLEQYDYLGASVIGAVVLIHALFTLLLINAFQIMKFRV---     266
Syn.PCC7942      LPFDDLIAPVLIFERLEQYDYKSATIIASFVLIISFTALFFINKIQLWKKTFHK-     278
Marchantia       IPMKDLVISVLLFQKLEQYDYKSATIIASFVLIISFTALFFINKIQLWKKTFHK-     288
Bacillus         LPMQTEITPLLIMTKLEQFDVAGATALAAVMLIISFFMLLFINILQWWSQRRQLS    279
                 :.: .* :* :  :***:*  :*  :. .::: .
```

Nephroselmis
Mesostigma
Chlamydomonas
Chlorella
Syn.PCC7942
Marchantia
Bacillus

```
CATTCAATTTGCAGCGTTCCTAAAATGGCAAGCACAACGCTGCTCCAGCCCGCGCTTGGTCTGCCCTCGCGGGTAGGG
CCTCGCTCCCCTCTGTCGCTTCCCAAAAATTCCTCGCGTGTGCACGCACACTAGTGCTCCCTCTACCTCAAAGTACTGC
GACTCATCATCAGTTATAGAGAGCACGCTAGGGCGGCAAACATCGGTTGCCGGGAGACCATGGCTTGCACCCCGGCCT
GCGCCTCAACAAAGCCGAGGCGACCTACTGGTCTCCAAATCGGGGCAGCAGGAGGCATGGGCGCCCATGGAGGGGGC
TTAGGGGAACCGGTCGATAATTGGATCAAGAAGCTACTCGTTGGTGTCGCGGCGGCGTACATCGGCTTGGTCGTGCTG
GTGCCCTTCCTGAATGTCTTCGTCCAGGCGTTCGCCAAGGGCATCATTCCCTTCCTGGAGCACTGCGCGGACCCGGAC
TTTCTGCACGCACTCAAGATGACGCTGATGCTGGCGTTCGTGACGGTGCCGCTCAACACGGTGTTTGGCACGGTGGCC
GCGATCAACCTCACGCGCAACGAGTTCCCCGGCAAGGTGTTCCTGATGTCGCTGCTGGACCTGCCCTTCTCCATCTCG
CCCGTGGTGACTGGCCTGATGCTCACGCTGCTGTACGGCCGCACCGGCTGGTTCGCGGCGCTGCTGCGGGAGACCGGC
ATCAACGTGGTGTTCGCATTCACGGGCATGGCCCTGGCCACCATGTTTGTGACGCTGCCGTTCGTGGTGCGCGAGCTG
ATCCCCATCCTGGAGAACATGGACCTGTCGCAGGAGGAGGCGGCGAGAACGCTGGGGGCCAACGACTGGCAGGTGTTC
TGGAACGTGACGCTGCCCAACATCCGCTGGGGCCTGCTGTACGGCGTGATCCTGTGCAACGCCCGAGCCATGGGCGAG
TTCGGAGCCGTGTCCGTCATCTCGGGCAACATCATCGGCCGCACGCAGACGCTGACGCTGTTCGTCGAGTCCGCCTAC
AAGGAGTACAACACGGAGGCGGCGTTCGCGGCGGCTGTGCTGCTGAGCGCGCTGGCGCTGGGCACCCTGTGGATCAAG
GACAAGGTGGAGGAGGCGGCGGCGGCGGAGAGCCGCAAGTAGAGAGGAGCAGGCGGCGTCGGCAGCGGCGGCAGTGGC
AGCGGCAGCGGCGGAGAGCGGCAGCTGGAGAGGAGCAGGCGGTGGCGGCGGAGCGGCGGAAATAGAGAGGTGCAGCAA
GGAGGCAGGCGCCGACGCGAGGGGAGGGCGTGGTGGTGGGCTTGCGTGGGTGCTTGGTCCGTGGCCAGGGTGCCTGGC
CTGGGTAGTTGGTGTGTGGGTGAAGCTGATTCCTGTTTGGGTGAGGCGGCCGAGTTCCTGAAGGAAGCAAGGAAGGAC
AGTGCCGCAGTGACCAGCGGGTAATGGTAAGGGAGCTGACACGTGTGGCGTTCTGTTGCTGGTCGCCGCATGCTTAAC
GCAGCGGGAGCAGCTTCTCTGTCTGATGTCTAACGGGGCGTTGTATGCTGATAATAGACGGAGGCGAAGGGAGCAG
GCGCGGTTCAGATGGGTAAAAGCTGTTGGAAATCAACACGTGCAGCGGGTGGGTTGCATTTGTGATCACTGGACGTT
CTGAGTGGTCCGTGCGCCTATAGCGCGTGCTGTGCATATATACGCGCGCCGGCGCATAAAACATGACTGCATGTGTCG
GTGTTGACGGTACAGTTATGCCGTGCCCCGTTTTACAAGCGGGATAGAGGCACACTCCACGTAGTATGCATTGAGCCC
AGTAGACTCTGGTCAGAAGGCCGGTAAATTTACATGTGTCGTGGTGAACCCTGTAAGTCATGGCCCAAG
```
(SEQ ID NO: 04)

FIG. 21

```
GTACTTCAATTGTCAGAATGGCGTCGCTGCTCGCTCAAACAACATCGCGCCTTGGCGCTCGCCCAGCTGCGCAA
GCTGGCCCTGTCGCCCAAATGGCACCGATGGCAAGCCGAGTGCAGCCGGCGATGCCTAGCGCGCTGCTCCCACT
GCACGCCAGAGCGACAACAACTTCAGTCGCTTGCCGGGCAGCCAGCATCGACAAACCTGTCGTTTACACTCCTC
GAGATTCGTCGCAACAGTCCTCCAATGGGGCAGGAGAAGTGTCCATGTCCATATCATCCATGGACGAGGTTGGA
CCCTCTTATGAGGGAATCATTACAGACGCGCCTACACGACCAACGGGGCTTTATGTGCGGGTGCGCAACATGGT
GAAGCACTTCAGCACCGCCAAAGGCCTGTTCAGGGCGGTGGACGGCGTGGACGTGGACATCGAGCCCAGCTCCA
TCGTGGCGCTGCTGGGGCCCAGCGGCAGCGGCAAGACCACATTGCTGCGCCTCATTGCAGGCCTGGAGCAGCCC
ACGGGCGGCAACATCTACTTTGACGACACGGACGCGACCAACCTGTCCGTCCAGGACCGCCAGATCGGCTTCGT
GTTCCAGAGCTATGCGCTGTTCAACCACAAGACAGTTGCGGAGAACATCAAGTTTGGACTGGAGGTGCGCAAGC
TCAACATCGACCACGACAAGCGCGTGGCGGAGCTGCTGGCGCTGGTGCAGCTCACCGGCCTGGGCGACCGCTAC
CCGCGCCAACTGTCGGGCGGCCAGCGGCAGCGTGTGGCGCTGGCGCGCGCCCTGGCCTCCAACCCGCGGCTGCT
GCTGCTGGACGAGCCCTTTGGCGCGCTGGACGCGGTGGTGCGCAAGCAGCTGCGCACGGGGCTGCGCGAGATCG
TGCGCAGCGTGGGCGTGACCACCATCATTGTGACGCACGACCAGGAGGAGGCGTTCGACCTGGCGGACAAGGTG
GTGGTGTTCAACAGGGGCCTGGTGGAGCAGCAGGGCAGCCCCACCGAGATCATCAAGCGGCCGCGCACGCCCTT
CATTATGAAGTTCGTGGGCGAGACCAACGTGGTGCCGGCCACGTCGCTGCTGGCCAAGCGCATGCGCTTCAACA
CCTCCAAGACCAGCGTCATGTTCCGGCCGCACGACATTAAGCTGTTCAAGACGGTGCCGCCGGAGAGCGGCGAG
GGCGCGCTGACCACGGTGGGCGCCAACGTGGCGGACAAAGCCAACCTGGGCTGGGTGGTCAAGTACACGCTGCG
CTTCGATGACGACGTGGAGTGCGAGCTGCAGCTCAGCCGCGACCAGGACGAGCGCGAGTACAACCTGGTGGTGG
GCAGCCGCGTGTTCGTGCACGTGCCGCACCGCACCATGATGGGCTTCAACGCCAGCGACGTGGACAGCACGCCC
ATCGTGTAATGTGCGGGGTTGGCGGCTGTGGCCAGCGATTGTTGCAATGCAGTCCAGCGTGCTCTTGGTTTGGT
TCCAGTGACACCCATCCAGGGCACAGGTCCCTGAGCAGCGGGTGTTGGTGATGGGTTGGAGCAGTTGTACCCGA
TTCTCGCATGCAAGGGGGCGGGGCGCCCACGGGGTGGGAGAGCGGAATGGCGGTGAGGTGGGCTACTGCATGCG
GCCGTGGAGGAACGGAGGGGTGCACAGGCGGGCAGGTAGACAGGCGGAGCGGGCTGGGTGAGCGGGGCTGTAGT
TTGGGGGTGGAGGCCGTGCAGACTGGTTGGGATACTGACAGATCAATGAGCGGCGTCTGCTCCATGGGTCAGTA
GGAGAGCGGTGTGGGTGTGTGCAGTTGCGAGTTCTGGAGCGTTGTGCGCCTCGCGCTGTGTGCGCGCGCCCGTG
CGTCTGCGGGCGCTGTCGGAGACGGGCGATGTACATGAAGCTGGACCTGGGCCTGTCTCACAAATATCCCTTAT
GTTAATAGTAGGATGTCGCAATCGTGCCTTGGAGCCCACCTGATGTGTGTGTCACAGGTGGCAGTAGTTTGGCC
TTGCGGGAGGTAGCACGTCTTTCATGAGAGTGCGTGTGCGTGACCGCTTTTACATTGCCAATCACGCTGGAAGG
TGAAACCATGCATCATGCGTGCTATCAGGAGATGCAGACGGCGGATTGCTGCCAAAATGTTCTGTTGTTGGTGT
GCAGACTTGGTGGCGAAGGGGCCAGGCGCCCAGGGGTATGCTGCGTGCCAAGGAGCTGCTGCCGCCACGAGTGA
CCAGCGAAACTTGTAAATTGAATATTGTATCCT (SEQ ID NO: 05)
```

FIG. 22

```
GGGCAGCGTATAAGTAATGTCGTTCTTGGCTCCCAGCTTAGGCGTCGCGCGGGGGATTCTGGAGCCGGCGAGTGC
AGCGAGGCCGCCTGCGCACGCGGCCGGTCACGCACCCGTTCTAACAAGCGATAGGACTGGTGGACCTGCCGCTAA
TCATGACAGGCCTGCCGGTGCTCCCAGCCCCCATGCGGCGTCGTTGACGCCCTCCAGCAGCGGGCAAGCAAGCCA
GCAAGGCGACCCCCAGCGCTCGCAGCACCAGCAAGCGCAGCGCCAGGACCAGCAGCAGTCGCAGTCGCGGTCGCT
CCAATCACACCTCATCACCGCGGCCACGCTGCTGCCAGCCCTGCCGCCTCCGCCTCCCGGCGGCAACGGCGACGG
CGATGGCGGCGAAGCTGCGGGGCCGCAGCCGCTCGCGGACGTCGCGGCTCAGCCGCCGGAGGTTGTGCTGACGCT
GGCGTCGTTCGCGGTGACCAAGCTGGCGTACGTGCGTGTGACGCGCGCGTTCCGGGAGTGGTACGAGCGCACGAA
GGGCGTGGATGTGCGCTTCCGCCTCACCTTCGCCGCCAGTGGCGTGCAGGCCCGCGCCGTGATCGATGGCCTGCC
CGCCGACATCGTGGCCCTGGCGCTGCCTCTGGACCTGGACAAGATCGTGTCGGCGGGCTGATCCGGCCCGACTG
GCGCAGCGCCTACCCGGCAGCCAGCGTGGTGTGCGAGACCACCGTGGCGTTCGTGGTGCGCCAGGGCAACCCCAA
GAACATCCGCACCTGGGAGGACCTCACGCGGGCGGGTGTGGAGGTGGTGCTGGCCAACCCCAAGACCGCCGGAGT
GGCCAGGTGGATCTTCCTGGCCCTGTGGGGCGCCAAGATGAAGAAGGGCAACGCCGCCGCGCTGGCGTATGTGCA
GCGCGTGTTCGAGAACGTGGTGGTGCAGCCGCGTGATGCGCGCGAGGCGTCGGACGTGTTCTATAAGCAGAAGGT
GGGCGACGTGCTGTTGACGTACGAGAACGAGGTGATCCTGACCAACGAGGTGTACGGCGACAAGGCGCTGCCGTA
CCTGGTGCCCTCCTACAACATCCGCATCGAGTGCCCGCTGGCGCTGGTGGACAAGGTGGTGGATGCCCGCGGCCC
CGAGGTGCGCGAGGCGGCGTCCGAGTTCTGCCGTTTCCTGTTCACGCCCGCGGCGCAGCACGAGTTCGCGCGGCT
GGGCTTCCGCGTGAACCCGCGCACCTGCAAGGAGGTGGCGGCGCAGCAGACCGGACTGCCGCCCGCAAACCTGTG
GCAGGTGGACAAGGAGCTGGGCGGCTGGGCTGCGGCCCAGAAGAAGTTTTTCGACGCTGGCGCCATCCTTGACGA
CATCCAGTCCGCCGTGGGCAAGCTGCGTGTGGAGCAGCGCAAGGCGGCGCAGGCGGCGGCCAGGCGGTAGAGAGA
CGCGGTACAAGTGCTCGGGTGCTCAGCAGGAGCTGCAGCAGGGGCAGCAAGAGGGCCTTGACAGGAGGGAATGGT
AGGCAAAGGCGGCAGGGGAGGCGGGATGCGGGATGAAGTGAGGGTGTGCAAGCAGCGATGTGTGCCAAGGACGG
TGTCGGCGATGTACATGATAACATGAGGAGACAGGAGCATCTCCTGGCAGGAGGCGGCAACCGTGGAGTGTCTGA
AAGGAGAACTTGATTGCTCAGTGTGGGACAGATAACGGAGGGCGGGGTGTGGGGCGTGGGGCTTATCGGTGTGCT
TCTATGGGGAGGCCTGACTGCATTGGGGGCGACGTAGTGTGATGGCCGCTACACGCTTGCTCGGAACTGACATAA
ACAGGCGTTCAGGCCATGGCTGCATGAGGCTTGATGTCGTATCGCGGACTGTC (SEQ ID NO: 06)
```

FIG. 23

MASTTLLQPALGLPSRVGPRSPLSLPKIPRVCTHTSAPSTSKYCDSSSVIESTLGRQTSV
AGRPWLAPRPAPQQSRGDLLVSKSGAAGGMGAHGGGLGEPVDNWIKKLLVGVAAAYIGLV
VLVPFLNVFVQAFAKGIIPFLEHCADPDFLHALKMTLMLAFVTVPLNTVFGTVAAINLTR
NEFPGKVFLMSLLDLPFSISPVVTGLMLTLLYGRTGWFAALLRETGINVVFAFTGMALAT
MFVTLPFVVRELIPILENMDLSQEEAARTLGANDWQVFWNVTLPNIRWGLLYGVILCNAR
AMGEFGAVSVISGNIIGRTQTLTLFVESAYKEYNTEAAFAAAVLLSALALGTLWIKDKVE
EAAAAESRK* (SEQ ID NO: 07)

FIG. 24

MASLLAQTTSRLGARPAAQAGPVAQMAPMASRVQPAMPSALLPLHARATTTSVAC
RAASIDKPVVYTPRDSSQQSSNGAGEVSMSISSMDEVGPSYEGIITDAPTRPTGL
YVRVRNMVKHFSTAKGLFRAVDGVDVDIEPSSIVALLGPSGSGKTTLLRLIAGLE
QPTGGNIYFDDTDATNLSVQDRQIGFVFQSYALFNHKTVAENIKFGLEVRKLNID
HDKRVAELLALVQLTGLGDRYPRQLSGGQRQRVALARALASNPRLLLLDEPFGAL
DAVVRKQLRTGLREIVRSVGVTTIIVTHDQEEAFDLADKVVVFNRGLVEQQGSPT
EIIKRPRTPFIMKFVGETNVVPATSLLAKRMRFNTSKTSVMFRPHDIKLFKTVPP
ESGEGALTTVGANVADKANLGWVVKYTLRFDDDVECELQLSRDQDEREYNLVXGS
RVFVHVPHRTMMGFNASDVDSTPIV* (SEQ ID NO: 08)

FIG. 25

MSFLAPSLGVARGILEPASAARPPAHAAGHAPVLTSDRTGGPAANHDRPAGAPSPH
AASLTPSSSGQASQQGDPQRSQHQQAQRQDQQQSQSRSLQSHLITAATLLPALPPPP
PGGNGDGDGGEAAGPQPLADVAAQPPEVVLTLASFAVTKLAYVRVTRAFREWYE
RTKGVDVRFRLTFAASGVQARAVIDGLPADIVALALPLDLDKIVSAGLIRPDWRSA
YPAASVVCETTVAFVVRQGNPKNIRTWEDLTRAGVEVVLANPKTAGVARWIFLAL
WGAKMKKGNAAALAYVQRVFENVVVQPRDAREASDVFYKQKVGDVLLTYENEV
ILTNEVYGDKALPYLVPSYNIRIECPLALVDKVVDARGPEVREAASEFCRFLFTPAA
QHEFARLGFRVNPRTCKEVAAQQTGLPPANLWQVDKELGGWAAAQKKFFDAGAI
LDDIQSAVGKLRVEQRKAAQAAARR* (SEQ ID NO: 09)

FIG. 26

Chloroplast Sulfate Transport System

SEQUENCE LISTING

<160> NUMBER OF SEQ ID NOS: 9

<210> SEQ ID NO 1
<211> LENGTH: 411
<212> TYPE: PRT
<213> ORGANISM: Chlamydomonas reinhardtii

<400> SEQUENCE: 1

```
Met Glu Arg Val Cys Ser His Gln Leu Ala Ser Ser Arg Gly Arg Pro
 1               5                  10                  15

Cys Ile Ala Gly Val Gln Arg Ser Pro Ile Arg Leu Gly Thr Ser Ser
            20                  25                  30

Val Ala His Val Gln Val Ser Pro Ala Gly Leu Gly Arg Tyr Gln Arg
        35                  40                  45

Gln Arg Leu Gln Val Val Ala Ser Ala Ala Ala Ala Ala Phe Asp
    50                  55                  60

Pro Pro Gly Gly Val Ser Ala Gly Phe Ser Gln Pro Gln Gln Gln Leu
65                  70                  75                  80

Pro Gln Gln His Pro Arg Gln Pro Gln Ala Val Ala Glu Val Ala Val
                85                  90                  95

Ala Glu Ser Val Ser Ala Pro Ala Ser Ala Ala Pro Ser Asn Asp Gly
            100                 105                 110

Ser Pro Thr Ala Ser Met Asp Gly Gly Pro Ser Ser Gly Leu Ser Ala
        115                 120                 125

Val Pro Ala Ala Thr Ala Thr Asp Leu Phe Ser Ala Ala Ala Arg
    130                 135                 140

Leu Arg Leu Pro Asn Leu Ser Pro Ile Ile Thr Trp Thr Phe Met Leu
145                 150                 155                 160

Ser Tyr Met Ala Phe Met Leu Ile Met Pro Ile Thr Ala Leu Leu Gln
                165                 170                 175

Lys Ala Ser Leu Val Pro Leu Asn Val Phe Ile Ala Arg Ala Thr Glu
            180                 185                 190

Pro Val Ala Met His Ala Tyr Tyr Val Thr Phe Ser Cys Ser Leu Ile
        195                 200                 205

Ala Ala Ala Ile Asn Cys Val Phe Gly Phe Val Leu Ala Trp Val Leu
    210                 215                 220

Val Arg Tyr Asn Phe Ala Gly Lys Lys Ile Leu Asp Ala Ala Val Asp
```

```
                225                 230                 235                 240
Leu Pro Phe Ala Leu Pro Thr Ser Val Ala Gly Leu Thr Leu Ala Thr
                    245                 250                 255
Val Tyr Gly Asp Glu Phe Phe Ile Gly Gln Phe Leu Gln Ala Gln Gly
                260                 265                 270
Val Gln Val Val Phe Thr Arg Leu Gly Val Val Ile Ala Met Ile Phe
            275                 280                 285
Val Ser Phe Pro Phe Val Val Arg Thr Met Gln Pro Val Met Gln Glu
        290                 295                 300
Ile Gln Lys Glu Met Glu Glu Ala Ala Trp Ser Leu Gly Ala Ser Gln
305                 310                 315                 320
Trp Arg Thr Phe Thr Asp Val Val Leu Pro Pro Leu Leu Pro Ala Leu
                325                 330                 335
Leu Thr Gly Thr Ala Leu Ala Phe Ser Arg Ala Leu Gly Glu Phe Gly
                340                 345                 350
Ser Ile Val Ile Val Ser Ser Asn Phe Ala Phe Lys Asp Leu Ile Ala
                355                 360                 365
Pro Val Leu Ile Phe Gln Cys Leu Glu Gln Tyr Asp Tyr Val Gly Ala
            370                 375                 380
Thr Val Ile Gly Thr Val Leu Leu Leu Ile Ser Leu Val Met Met Leu
385                 390                 395                 400
Ala Val Asn Gln Leu Gln Lys Leu Ala Arg Lys
                    405                 410

<210> SEQ ID NO 2
<211> LENGTH: 3873
<212> TYPE: DNA
<213> ORGANISM: Chlamydomonas reinhardtii

<400> SEQUENCE: 2
gcttagtacc taagcaaaaa taccaaagcc ttatcctgag ttgtcaacaa gaactccagc      60
ctgcgacgat gcaaagcctt tcttgagcgg gttgatggac tttgctttgt tatctgtcca     120
gtaagccacc agacactacc aagtagagta atccatttgt ataggtacag aatatggagc     180
gagtttgcag ccatcagctt gcctcgtcgc gagggaggcc atgcatcgct ggggtgcagc     240
ggtcgcccat ccgactaggg acttcaagcg ttgctcatgt gcaggtctct ccggcaggta     300
agcaccgcgc tcggcggcgt gtacacatgg ggccgtcagg ccaactgcgt tgttggcta     360 tgcaaccgaa acaggccttg ggagatatca acggcaaaga ctgcaagtcg tggcgtctgc     420
agctgcggca gcggctttcg accctcctgg aggtgcgtgg cgtgagggct gcacgggtgc     480
gggttggcct ggaaaccaag cctcgccacg actacctgca acagcattgc cgcatctcc      540 agcccctcac cctcgagtgc ctcccgaaga cctctatccc ctgcgcatca ttggttcggg     600
ggcgccgcct gcgggccttg ggcgctggct acgctgaccg cacggcacga cttggcacgg     660
cctggcgcgg cctgagcggc ccccccctc ctgatggccc cacgctttgc cgcccacgcc      720
gctccccgca ggtgtctccg ccgggttctc gcagccgcaa cagcagctgc acaacagca      780 cccacgccaa ccacaggcgg tggcggaggt agctgtcgcc gagtcagtct cggcgcccgc     840
ttctgcggcg ccctccaatg atggctcgcc cacggcctcc atgacggcg gccccagctc      900 cggcctcagc gccgtgcccg ccgccgccac cgccaccgac ctcttctccg ccgcggcgcg     960
cctccgcctg cccaacctct cccccatcat cacctggacc ttcatgctct cctacatggc    1020
cttcatgctc atcatgccca tcaccgcgct gctgcaaaaa gcctcgctcg tgccgctcaa    1080
```

-continued

```
cgtcttcatc gcgcgcgcca ccgagccggt ggcgatgcac gcctactacg tcaccttctc    1140
ctgctcgctg atcgcggccg ccatcaactg cgtgtttggc ttcgtgctgg cctgggtgct    1200
ggtgcgctac aatttcgcgg ggaagaagat cctggacgcg gcggtggacc tgccgttcgc    1260
gctgccgacc tcggtggcgg gcctcacgct tgccacggtg tacggcgacg agttcttcat    1320
cggccagttc ctgcaggcgc agggcgtgca ggtgcgtgcg tatagcatag tggagtgtgg    1380
ttagcagctg ggggtccggc agtagttccc gccctagtga ggtcgaaact ataccagaag    1440
aagaggacga acatgggct atccagcaag ctcgtctagg aaggaggag tttgggagaa    1500 cggtggggtg ggagggagag ggagggcgtt ggctgggagg gaagggtaag gcggagggga    1560
gatggtagca cggggcgttg gggacgcaga aggatgacag gcggctgcag ggaagggatg    1620
gggaagcgga gctggggaca gtgcgaagag ccggggagaga ggggaagttt gagtcaggaa    1680
gaggggctag agaggggcat gcggactcct gctgggattt aggtgcgtgc tcattgagga    1740
gcccttggaa tcagcggacg gaaacgtggc cgacggggtc tgccgagcac accaggctag    1800
ctagacgcgc ggttgggcaa cgagcagagc tgctgtgcgg ctatggatgg aaggcgatgc    1860
agcgagcatg tgcagtgaac attggtttga ggacagggga ctccgaggtt gcataggcgg    1920
gccgccactg tctctgccgc tagggtgact agctgcctcg aacctggcgg tggccccata    1980
cccgcagttg gaggatgctc cacgcgcttc agcttgccat gtctgggtc tgggtctgga    2040 cgcaatcagc gtgtgagggt ccaactctat atggaattat ggatacctcc caactaccag    2100
cacgtaggct gccggaacgc ggctgaagcg gctggcctgc cccctcatcc tctcgttccc    2160 ctgttttgt cccctgtcca cccaggtggt gttcacgcgg ctgggtgtgg tgatcgccat    2220
gatcttcgtg tccttcccct tcgtggtgcg caccatgcag cccgtcatgc aggtgagagc    2280
gcccaggagg cggagccatg gcgggttggg gcgggttggg gcgggttggg gcggggcgcg    2340
gatgggcggg cttggggagt aatgtggggc ggatgggtg gcagcctggc agggtatggg    2400
agcgagagga tagcggggac aggggacagg gaagggaagg gaagggaagg gatgccctat    2460
gcgagcaaag ggggtatggg aaccggcggt tggggctggg agcgacggga gcagggaggg    2520
agtgcacgga acggggcaa gcggacagg gtgagggagg gtgcaggccg gactgggatg    2580
ggtcatgtgt cctggtcggg ggtgtagccg tgggaggcgg gcaggcagcg tgtgttctgg    2640
cacggtgttt tggcgaaaga taccacggca tggtatgggg ccagttgggc agggaagaac    2700
cgttggacac gacttcgttg acagatctag ttcattgcac ccgggtcgca ccaagggtgg    2760
cggcgagccc ggcccggcac gtccgagtac cccgagccg taacgccgca acccgccttg    2820
ttgcgcccct tccctgctcc cctgctccgc ataccgtgca ccatgccctc tgccgccccc    2880
tcaggccctc aggccctcac ctccccctca cctcctccta acgccttccc ctcgccttcc    2940
cttcccctcc caacgccacc acgtgcaaca ggaaatccaa aaggagatgg aggaggcggc    3000
atggtcgctg ggcgcctcgc agtggcgcac cttcacagac gtggtgctgc cgccgctgct    3060
gcccgcgctg ctgaccggca cggcactggc cttctcgcgc gcgcttggcg agttcggatc    3120
cattgtcatc gtgtcctcca actttgcctt caaggacctg atcgcgcccg tgctgatctt    3180
ccagtgcctg gagcagtacg actacgtggg cgccaccgtg atcggcacag tactgctgtt    3240
gatttcgctg gtgatgatgt tggcggtgaa ccagctgcag aagctggcgc gcaagtgagg    3300
ggctgaggcg tttgaggaga gtgggcgtct gcggaggcgc ttgtggcgca ggggcaggtg    3360
gaggaggttg cagggtgagg caggagtggc agtggtggga gggtgcaggg cggggtgttg    3420
ggatgggatg ggatgggacc gtgggagggg tgggactttg ggtggtgggg agtgggtgct    3480
```

-continued

```
acgtattagg atatgggagg tggtatgcag ttgaaggggg gggtggcaat ctggacgggg      3540
actcactgtt tactaggcac gcatgtcgca ggagtggata tcgatgggtg tggggatgtc      3600
agcacgcttg gcttgagttg ggccatggga cccgggacta ggcttggttg cgagccgagc      3660
cagtcaccag ggagacgtac gagcgcacac agtgattacg gggattgatt aggcggcgaa      3720
ttgacgcaaa tccacggggg ctgtggcttg ggggaggcag ggattgagcg aaggacgcac      3780
tgcaagctca ggcagtcgca tgcccgtacc ctgcttctgg tccagtgtgg agacaagact      3840
ggcaatcgtg gtcctttgca attcatggcg cgc                                  3873
```

<210> SEQ ID NO 3
<211> LENGTH: 1984
<212> TYPE: DNA
<213> ORGANISM: Chlamydomonas reinhardtii

<400> SEQUENCE: 3

```
gcttagtacc taagcaaaaa taccaaagcc ttatcctgag ttgtcaacaa gaactccagc       60
ctgcgacgat gcaaagcctt tcttgagcgg gttgatggac tttgctttgt tatctgtcca      120
gtaagccacc agacactacc aagtagagta atccatttgt ataggtacag aatatggagc      180
gagtttgcag ccatcagctt gcctcgtcgc gagggaggcc atgcatcgct ggggtgcagc      240
ggtcgcccat ccgactaggg acttcaagcg ttgctcatgt gcaggtctct ccggcaggcc      300
ttgggagata tcaacggcaa agactgcaag tcgtggcgtc tgcagctgcg gcagcggctt      360
tcgaccctcc tggaggtgtc tccgccgggt tctcgcagcc gcaacagcag ctgccacaac      420
agcacccacg ccaaccacag gcggtggcgg aggtagctgt cgccgagtca gtctcggcgc      480
ccgcttctgc ggcgccctcc aatgatggct cgcccacggc ctccatggac ggcggcccca      540
gctccggcct cagcgccgtg cccgccgccg ccaccgccac cgacctcttc tccgccgcgg      600
cgcgcctccg cctgcccaac ctctcccca tcatcacctg gaccttcatg ctctcctaca      660
tggccttcat gctcatcatg cccatcaccg cgctgctgca aaaagcctcg ctcgtgccgc      720
tcaacgtctt catcgcgcgc gccaccgagc cggtggcgat gcacgcctac tacgtcacct      780
tctcctgctc gctgatcgcg gccgccatca actgcgtgtt tggcttcgtg ctggcctggg      840
tgctggtgcg ctacaatttc gcggggaaga agatcctgga cgcggcggtg gacctgccgt      900
tcgcgctgcc gacctcggtg gcgggcctca cgcttgccac ggtgtacggc gacgagttct      960
tcatcggcca gttcctgcag gcgcagggcg tgcaggtggt gttcacgcgg ctgggtgtgg     1020
tgatcgccat gatcttcgtg tccttcccct tcgtggtgcg caccatgcag cccgtcatgc     1080
aggaaatcca aaaggagatg gaggaggcgg catggtcgct gggcgcctcg cagtggcgca     1140
ccttcacaga cgtggtgctg ccgccgctgc tgcccgcgct gctgaccggc acggcactgg     1200
ccttctcgcg cgcgcttggc gagttcggat ccattgtcat cgtgtcctcc aactttgcct     1260
tcaaggacct gatcgcgccc gtgctgatct tccagtgcct ggagcagtac gactacgtgg     1320
gcgccaccgt gatcggcaca gtactgctgt tgatttcgct ggtgatgatg ttggcggtga     1380
accagctgca gaagctggcg cgcaagtgag ggctgaggc gtttgaggag agtgggcgtc     1440
tgcggaggcg cttgtggcgc aggggcaggt ggaggaggtt gcaggtgag gcaggagtgg      1500 caggtggtgg agggtgcagg gcgggtgtt gggatgggat gggatgggac cgtgggaggg     1560
gtgggacttt gggtgggtgg gagtgggtgc tacgtattag gatatgggag gtggtatgca     1620
gttgaagggg ggggtggcaa tctggacggg gactcactgt ttactaggca cgcatgtcgc     1680
```

-continued

| | |
|---|---|
| aggagtggat atcgatgggt gtggggatgt cagcacgctt ggcttgagtt gggccatggg | 1740 |
| acccgggact aggcttggtt gcgagccgag ccagtcacca gggagacgta cgagcgcaca | 1800 |
| cagtgattac ggggattgat taggcggcga attgacgcaa atccacgggg gctgtggctt | 1860 |
| gggggaggca gggattgagc gaaggacgca ctgcaagctc aggcagtcgc atgcccgtac | 1920 |
| cctgcttctg gtccagtgtg gagacaagac tggcaatcgt ggtcctttgc aattcatggc | 1980 |
| gcgc | 1984 |

<210> SEQ ID NO 4
<211> LENGTH: 1863
<212> TYPE: DNA
<213> ORGANISM: Chlamydomonas reinhardtii

<400> SEQUENCE: 4

| | |
|---|---|
| cattcaattt gcagcgttcc taaaatggca agcacaacgc tgctccagcc cgcgcttggt | 60 |
| ctgccctcgc gggtagggcc tcgctcccct ctgtcgcttc ccaaaattcc tcgcgtgtgc | 120 |
| acgcacacta gtgctccctc tacctcaaag tactgcgact catcatcagt tatagagagc | 180 |
| acgctagggc ggcaaacatc ggttgccggg agaccatggc ttgcaccccg gcctgcgcct | 240 |
| caacaaagcc gaggcgacct actggtctcc aaatcggggg cagcaggagg catgggcgcc | 300 |
| catggagggg gcttagggga accggtcgat aattggatca agaagctact cgttggtgtc | 360 |
| gcggcggcgt acatcggctt ggtcgtgctg gtgcccttcc tgaatgtctt cgtccaggcg | 420 |
| ttcgccaagg gcatcattcc cttcctggag cactgcgcgg acccggactt tctgcacgca | 480 |
| ctcaagatga cgctgatgct ggcgttcgtg acggtgccgc tcaacacggt gtttggcacg | 540 |
| gtggccgcga tcaacctcac gcgcaacgag ttccccggca aggtgttcct gatgtcgctg | 600 |
| ctggacctgc ccttctccat ctcgcccgtg gtgactggcc tgatgctcac gctgctgtac | 660 |
| ggccgcaccg gctggttcgc ggcgctgctg cgggagaccg gcatcaacgt ggtgttcgca | 720 |
| ttcacgggca tggccctggc caccatgttt gtgacgctgc cgttcgtggt gcgcgagctg | 780 |
| atccccatcc tggagaacat ggacctgtcg caggaggagg cggcgagaac gctgggggcc | 840 |
| aacgactggc aggtgttctg gaacgtgacg ctgcccaaca tccgctgggg cctgctgtac | 900 |
| ggcgtgatcc tgtgcaacgc ccgagccatg ggcgagttcg gagccgtgtc cgtcatctcg | 960 |
| ggcaacatca tcggccgcac gcagacgctg acgctgttcg tcgagtccgc ctacaaggag | 1020 |
| tacaacacgg aggcggcgtt cgcggcggct gtgctgctga gcgcgctggc gctgggcacc | 1080 |
| ctgtggatca aggacaaggt ggaggaggcg gcggcggcg agagccgcaa gtagagagga | 1140 |
| gcaggcggcg tcggcagcgg cggcagtggc agcggcagcg gcggagagcg gcagctggag | 1200 |
| aggagcaggc ggtggcggcg gagcggcgga aatagagagg tgcagcaagg aggcaggcgc | 1260 |
| cgacgcgagg ggagggcgtg gtggtgggct tgcgtgggtg cttggtccgt ggccagggtg | 1320 |
| cctggcctgg gtagttggtg tgtgggtgaa gctgattcct gtttgggtga ggcggccgag | 1380 |
| ttcctgaagg aagcaaggaa ggacagtgcc gcagtgacca gcgggtaatg gtaagggagc | 1440 |
| tgacacgtgt ggcgttctgt tgctggtcgc cgcatgctta acgcagcggg agcagcttct | 1500 |
| ctgtctgatg tctaacgggg gcgttgtatg ctgataatag acggagggcg aagggagcag | 1560 |
| gcgcggttca gatggggtaa aagctgttgg aaatcaacac gtgcagcggg tggggttgcat | 1620 |
| ttgtgatcac tggacgttct gagtggtccg tgcgcctata gcgcgtgctg tgcatatata | 1680 |
| cgcgcgccgg cgcataaaac atgactgcat tgtgtcggtgt tgacggtaca gttatgccgt | 1740 |
| gccccgttttt acaagcggga tagaggcaca ctccacgtag tatgcattga gcccagtaga | 1800 |

```
ctctggtcag aaggccggta aatttacatg tgtcgtggtg aaccctgtaa gtcatggccc    1860
aag                                                                  1863
```

<210> SEQ ID NO 5
<211> LENGTH: 2253
<212> TYPE: DNA
<213> ORGANISM: Chlamydomonas reinhardtii

<400> SEQUENCE: 5

```
gtacttcaat tgtcagaatg gcgtcgctgc tcgctcaaac aacatcgcgc cttggcgctc      60
gcccagctgc gcaagctggc cctgtcgccc aaatggcacc gatggcaagc cgagtgcagc     120
cggcgatgcc tagcgcgctg ctcccactgc acgccagagc gacaacaact tcagtcgctt     180
gccgggcagc cagcatcgac aaacctgtcg tttacactcc tcgagattcg tcgcaacagt     240
cctccaatgg ggcaggagaa gtgtccatgt ccatatcatc catggacgag gttggaccct     300
cttatgaggg aatcattaca gacgcgccta cacgaccaac ggggctttat gtgcgggtgc     360
gcaacatggt gaagcacttc agcaccgcca aaggcctgtt cagggcggtg gacggcgtgg     420
acgtggacat cgagcccagc tccatcgtgg cgctgctggg gcccagcggc agcggcaaga     480
ccacattgct gcgcctcatt gcaggcctgg agcagcccac gggcggcaac atctactttg     540
acgacacgga cgcgaccaac ctgtccgtcc aggaccgcca gatcggcttc gtgttccaga     600
gctatgcgct gttcaaccac aagacagttg cggagaacat caagtttgga ctggaggtgc     660
gcaagctcaa catcgaccac gacaagcgcg tggcggagct gctggcgctg gtgcagctca     720
ccggcctggg cgaccgctac ccgcgccaac tgtcgggcgg ccagcggcag cgtgtggcgc     780
tggcgcgcgc cctggcctcc aacccgcggc tgctgctgct ggacgagccc tttggcgcgc     840
tggacgcggt ggtgcgcaag cagctgcgca cggggctgcg cgagatcgtg cgcagcgtgg     900
gcgtgaccac catcattgtg acgcacgacc aggaggaggc gttcgacctg gcggacaagg     960
tggtggtgtt caacaggggc ctggtggagc agcagggcag ccccaccgag atcatcaagc    1020
ggccgcgcac gcccttcatt atgaagttcg tgggcgagac caacgtggtg ccggccacgt    1080
cgctgctggc caagcgcatg cgcttcaaca cctccaagac cagcgtcatg ttccggccgc    1140
acgacattaa gctgttcaag acggtgccgc cggagagcgg cgaggcgcg ctgaccacgg     1200
tgggcgccaa cgtggcggac aaagccaacc tgggctgggt ggtcaagtac acgctgcgct    1260
tcgatgacga cgtggagtgc gagctgcagc tcagccgcga ccaggacgag cgcgagtaca    1320
acctggtggt gggcagccgc gtgttcgtgc acgtgccgca ccgcaccatg atgggcttca    1380
acgccagcga cgtggacagc acgcccatcg tgtaatgtgc gggtttggcg gctgtggcca    1440
gcgattgttg caatgcagtc cagcgtgctc ttggtttggt tccagtgaca cccatccagg    1500
gcacaggtcc ctgagcagcg ggtgttggtg atgggttgga gcagttgtac ccgattctcg    1560
catgcaaggg ggcggggcgc ccacggggtg ggagagcgga atggcggtga ggtgggctac    1620
tgcatgcggc cgtggaggaa cggaggggtg cacaggcggg caggtagaca ggcggagcgg    1680
gctgggtgag cggggctgta gtttgggggt ggaggccgtg cagactggtt gggatactga    1740
cagatcaatg agcggcgtct gctccatggg tcagtaggag agcggtgtgg gtgtgtgcag    1800
ttgcgagttc tggagcgttg tgcgcctcgc gctgtgtgcg cgcgcccgtg cgtctgcggg    1860
cgctgtcgga gacgggcgat gtacatgaag ctggacctgg gcctgtctca caaatatccc    1920
ttatgttaat agtaggatgt cgcaatcgtg ccttggagcc cacctgatgt gtgtgtcaca    1980
```

-continued

```
ggtggcagta gtttggcctt gcgggaggta gcacgtcttt catgagagtg cgtgtgcgtg    2040
accgctttta cattgccaat cacgctggaa ggtgaaacca tgcatcatgc gtgctatcag    2100
gagatgcaga cggcggattg ctgccaaaat gttctgttgt tggtgtgcag acttggtggc    2160
gaagggccca ggcgcccagg ggtatgctgc gtgccaagga gctgctgccg ccacgagtga    2220
ccagcgaaac ttgtaaattg aatattgtat cct                                 2253
```

<210> SEQ ID NO 6
<211> LENGTH: 1853
<212> TYPE: DNA
<213> ORGANISM: Chlamydomonas reinhardtii

<400> SEQUENCE: 6

```
gggcagcgta taagtaatgt cgttcttggc tcccagctta ggcgtcgcgc ggggattct      60 ggagccggcg agtgcagcga ggccgcctgc gcacgcggcc ggtcacgcac ccgttctaac    120
aagcgatagg actggtggac ctgccgctaa tcatgacagg cctgccggtg ctcccagccc    180
ccatgcggcg tcgttgacgc cctccagcag cgggcaagca agccagcaag gcgaccccca    240
gcgctcgcag caccagcaag cgcagcgcca ggaccagcag cagtcgcagt cgcggtcgct    300
ccaatcacac ctcatcaccg cggccacgct gctgccagcc ctgccgcctc cgcctcccgg    360
cggcaacggc gacggcgatg gcggcgaagc tgcggggccg cagccgctcg cggacgtcgc    420
ggctcagccg ccggaggttg tgctgacgct ggcgtcgttc gcggtgacca agctggcgta    480
cgtgcgtgtg acgcgcgcgt tccgggagtg gtacgagcgc acgaagggcg tggatgtgcg    540
cttccgcctc accttcgccg ccagtggcgt gcaggcccgc gccgtgatcg atggcctgcc    600
cgccgacatc gtggccctgg cgctgcctct ggacctggac aagatcgtgt cggcggggct    660
gatccggccc gactggcgca cgcctaccc ggcagccagc gtggtgtgcg agaccaccgt     720
ggcgttcgtg gtgcgccagg gcaaccccaa gaacatccgc acctgggagg acctcacgcg    780
ggcgggtgtg gaggtggtgc tggccaaccc caagaccgcc ggagtggcca ggtggatctt    840
cctggccctg tggggcgcca agatgaagaa gggcaacgcc gccgcgctgg cgtatgtgca    900
gcgcgtgttc gagaacgtgg tggtgcagcc gcgtgatgcg cgcgaggcgt cggacgtgtt    960
ctataagcag aaggtgggcg acgtgctgtt gacgtacgag aacgaggtga tcctgaccaa    1020
cgaggtgtac ggcgacaagg cgctgccgta cctggtgccc tcctacaaca tccgcatcga    1080
gtgcccgctg cgcgctggtg acaaggtggt ggatgcccgc ggccccgagg tgcgcgaggc    1140
ggcgtccgag ttctgccgtt tcctgttcac gcccgcggcg cagcacgagt tcgcgcggct    1200
gggcttccgc gtgaacccgc gcacctgcaa ggaggtggcg gcgcagcaga ccggactgcc    1260
gcccgcaaac ctgtggcagg tggacaagga gctgggcggc tgggctgcgg cccagaagaa    1320
gtttttcgac gctggcgcca tccttgacga catccagtcc gccgtgggca agctgcgtgt    1380
ggagcagcgc aaggcggcgc aggcggcgg caggcggtag agagacgcgg tacaagtgct    1440
cgggtgctca gcaggagctg cagcagggc agcaagaggg ccttgacagg agggaatggt    1500
aggcaaaggc ggcaggggag gcgggatggc gggatgaagt gagggtgtgc aagcagcgat    1560
gtgtgccaag gacggtgtcg gcgatgtaca tgataacatg aggagacagg agcatctcct    1620
ggcaggaggc ggcaaccgtg gagtgtctga aggagaact  tgattgctca gtgtgggaca    1680
gataacggag ggcggggtgt ggggcgtggg gcttatcggt gtgcttctat ggggaggcct    1740
gactgcattg ggggcgacgt agtgtgatgg ccgctcacg cttgctcgga actgacataa     1800
acaggcgttc aggccatggc tgcatgaggc ttgatgtcgt atcgcggact gtc            1853
```

<210> SEQ ID NO 7
<211> LENGTH: 369
<212> TYPE: PRT
<213> ORGANISM: Chlamydomonas reinhardtii

<400> SEQUENCE: 7

```
Met Ala Ser Thr Thr Leu Leu Gln Pro Ala Leu Gly Leu Pro Ser Arg
 1               5                  10                  15

Val Gly Pro Arg Ser Pro Leu Ser Leu Pro Lys Ile Pro Arg Val Cys
            20                  25                  30

Thr His Thr Ser Ala Pro Ser Thr Ser Lys Tyr Cys Asp Ser Ser Ser
        35                  40                  45

Val Ile Glu Ser Thr Leu Gly Arg Gln Thr Ser Val Ala Gly Arg Pro
    50                  55                  60

Trp Leu Ala Pro Arg Pro Ala Pro Gln Gln Ser Arg Gly Asp Leu Leu
 65                  70                  75                  80

Val Ser Lys Ser Gly Ala Ala Gly Gly Met Gly Ala His Gly Gly Gly
                85                  90                  95

Leu Gly Glu Pro Val Asp Asn Trp Ile Lys Lys Leu Leu Val Gly Val
            100                 105                 110

Ala Ala Ala Tyr Ile Gly Leu Val Val Leu Val Pro Phe Leu Asn Val
        115                 120                 125

Phe Val Gln Ala Phe Ala Lys Gly Ile Ile Pro Phe Leu Glu His Cys
    130                 135                 140

Ala Asp Pro Asp Phe Leu His Ala Leu Lys Met Thr Leu Met Leu Ala
145                 150                 155                 160

Phe Val Thr Val Pro Leu Asn Thr Val Phe Gly Thr Val Ala Ala Ile
                165                 170                 175

Asn Leu Thr Arg Asn Glu Phe Pro Gly Lys Val Phe Leu Met Ser Leu
            180                 185                 190

Leu Asp Leu Pro Phe Ser Ile Ser Pro Val Val Thr Gly Leu Met Leu
        195                 200                 205

Thr Leu Leu Tyr Gly Arg Thr Gly Trp Phe Ala Ala Leu Leu Arg Glu
    210                 215                 220

Thr Gly Ile Asn Val Val Phe Ala Phe Thr Gly Met Ala Leu Ala Thr
225                 230                 235                 240

Met Phe Val Thr Leu Pro Phe Val Val Arg Glu Leu Ile Pro Ile Leu
                245                 250                 255

Glu Asn Met Asp Leu Ser Gln Glu Glu Ala Ala Arg Thr Leu Gly Ala
            260                 265                 270

Asn Asp Trp Gln Val Phe Trp Asn Val Thr Leu Pro Asn Ile Arg Trp
        275                 280                 285

Gly Leu Leu Tyr Gly Val Ile Leu Cys Asn Ala Arg Ala Met Gly Glu
    290                 295                 300

Phe Gly Ala Val Ser Val Ile Ser Gly Asn Ile Ile Gly Arg Thr Gln
305                 310                 315                 320

Thr Leu Thr Leu Phe Val Glu Ser Ala Tyr Lys Glu Tyr Asn Thr Glu
                325                 330                 335

Ala Ala Phe Ala Ala Val Leu Leu Ser Ala Leu Ala Leu Gly Thr
            340                 345                 350

Leu Trp Ile Lys Asp Lys Val Glu Glu Ala Ala Ala Glu Ser Arg
        355                 360                 365

Lys
```

```
<210> SEQ ID NO 8
<211> LENGTH: 465
<212> TYPE: PRT
<213> ORGANISM: Chlamydomonas reinhardtii
<220> FEATURE:
<221> NAME/KEY: VARIANT
<222> LOCATION: 438
<223> OTHER INFORMATION: Xaa = Any Amino Acid

<400> SEQUENCE: 8

Met Ala Ser Leu Leu Ala Gln Thr Thr Ser Arg Leu Gly Ala Arg Pro
  1               5                  10                  15

Ala Ala Gln Ala Gly Pro Val Ala Gln Met Ala Pro Met Ala Ser Arg
             20                  25                  30

Val Gln Pro Ala Met Pro Ser Ala Leu Leu Pro Leu His Ala Arg Ala
         35                  40                  45

Thr Thr Thr Ser Val Ala Cys Arg Ala Ala Ser Ile Asp Lys Pro Val
 50                  55                  60

Val Tyr Thr Pro Arg Asp Ser Gln Gln Ser Ser Asn Gly Ala Gly
 65                  70                  75                  80

Glu Val Ser Met Ser Ile Ser Ser Met Asp Glu Val Gly Pro Ser Tyr
                 85                  90                  95

Glu Gly Ile Ile Thr Asp Ala Pro Thr Arg Pro Thr Gly Leu Tyr Val
            100                 105                 110

Arg Val Arg Asn Met Val Lys His Phe Ser Thr Ala Lys Gly Leu Phe
        115                 120                 125

Arg Ala Val Asp Gly Val Asp Val Asp Ile Glu Pro Ser Ser Ile Val
    130                 135                 140

Ala Leu Leu Gly Pro Ser Gly Ser Gly Lys Thr Thr Leu Leu Arg Leu
145                 150                 155                 160

Ile Ala Gly Leu Glu Gln Pro Thr Gly Gly Asn Ile Tyr Phe Asp Asp
                165                 170                 175

Thr Asp Ala Thr Asn Leu Ser Val Gln Asp Arg Gln Ile Gly Phe Val
            180                 185                 190

Phe Gln Ser Tyr Ala Leu Phe Asn His Lys Thr Val Ala Glu Asn Ile
        195                 200                 205

Lys Phe Gly Leu Glu Val Arg Lys Leu Asn Ile Asp His Asp Lys Arg
    210                 215                 220

Val Ala Glu Leu Leu Ala Leu Val Gln Leu Thr Gly Leu Gly Asp Arg
225                 230                 235                 240

Tyr Pro Arg Gln Leu Ser Gly Gly Gln Arg Gln Arg Val Ala Leu Ala
                245                 250                 255

Arg Ala Leu Ala Ser Asn Pro Arg Leu Leu Leu Asp Glu Pro Phe
            260                 265                 270

Gly Ala Leu Asp Ala Val Val Arg Lys Gln Leu Arg Thr Gly Leu Arg
        275                 280                 285

Glu Ile Val Arg Ser Val Gly Val Thr Thr Ile Ile Val Thr His Asp
    290                 295                 300

Gln Glu Glu Ala Phe Asp Leu Ala Asp Lys Val Val Phe Asn Arg
305                 310                 315                 320

Gly Leu Val Glu Gln Gln Gly Ser Pro Thr Glu Ile Ile Lys Arg Pro
                325                 330                 335

Arg Thr Pro Phe Ile Met Lys Phe Val Gly Glu Thr Asn Val Val Pro
            340                 345                 350
```

```
Ala Thr Ser Leu Leu Ala Lys Arg Met Arg Phe Asn Thr Ser Lys Thr
            355                 360                 365

Ser Val Met Phe Arg Pro His Asp Ile Lys Leu Phe Lys Thr Val Pro
    370                 375                 380

Pro Glu Ser Gly Glu Gly Ala Leu Thr Thr Val Gly Ala Asn Val Ala
385                 390                 395                 400

Asp Lys Ala Asn Leu Gly Trp Val Val Lys Tyr Thr Leu Arg Phe Asp
            405                 410                 415

Asp Asp Val Glu Cys Glu Leu Gln Leu Ser Arg Asp Gln Asp Glu Arg
        420                 425                 430

Glu Tyr Asn Leu Val Xaa Gly Ser Arg Val Phe Val His Val Pro His
            435                 440                 445

Arg Thr Met Met Gly Phe Asn Ala Ser Asp Val Asp Ser Thr Pro Ile
    450                 455                 460

Val
465

<210> SEQ ID NO 9
<211> LENGTH: 467
<212> TYPE: PRT
<213> ORGANISM: Chlamydomonas reinhardtii

<400> SEQUENCE: 9

Met Ser Phe Leu Ala Pro Ser Leu Gly Val Ala Arg Gly Ile Leu Glu
1               5                   10                  15

Pro Ala Ser Ala Arg Pro Pro Ala His Ala Ala Gly His Ala Pro
            20                  25                  30

Val Leu Thr Ser Asp Arg Thr Gly Gly Pro Ala Ala Asn His Asp Arg
            35                  40                  45

Pro Ala Gly Ala Pro Ser Pro His Ala Ala Ser Leu Thr Pro Ser Ser
    50                  55                  60

Ser Gly Gln Ala Ser Gln Gln Gly Asp Pro Gln Arg Ser Gln His Gln
65                  70                  75                  80

Gln Ala Gln Arg Gln Asp Gln Gln Ser Gln Ser Arg Ser Leu Gln
            85                  90                  95

Ser His Leu Ile Thr Ala Ala Thr Leu Leu Pro Ala Leu Pro Pro Pro
            100                 105                 110

Pro Pro Gly Gly Asn Gly Asp Gly Asp Gly Gly Glu Ala Ala Gly Pro
        115                 120                 125

Gln Pro Leu Ala Asp Val Ala Ala Gln Pro Pro Glu Val Val Leu Thr
    130                 135                 140

Leu Ala Ser Phe Ala Val Thr Lys Leu Ala Tyr Val Arg Val Thr Arg
145                 150                 155                 160

Ala Phe Arg Glu Trp Tyr Glu Arg Thr Lys Gly Val Asp Val Arg Phe
            165                 170                 175

Arg Leu Thr Phe Ala Ala Ser Gly Val Gln Ala Arg Ala Val Ile Asp
        180                 185                 190

Gly Leu Pro Ala Asp Ile Val Ala Leu Ala Leu Pro Leu Asp Leu Asp
    195                 200                 205

Lys Ile Val Ser Ala Gly Leu Ile Arg Pro Asp Trp Arg Ser Ala Tyr
    210                 215                 220

Pro Ala Ala Ser Val Val Cys Glu Thr Thr Val Ala Phe Val Val Arg
225                 230                 235                 240

Gln Gly Asn Pro Lys Asn Ile Arg Thr Trp Glu Asp Leu Thr Arg Ala
            245                 250                 255
```

-continued

```
Gly Val Glu Val Val Leu Ala Asn Pro Lys Thr Ala Gly Val Ala Arg
            260                 265                 270

Trp Ile Phe Leu Ala Leu Trp Gly Ala Lys Met Lys Lys Gly Asn Ala
            275                 280                 285

Ala Ala Leu Ala Tyr Val Gln Arg Val Phe Glu Asn Val Val Val Gln
            290                 295                 300

Pro Arg Asp Ala Arg Glu Ala Ser Asp Val Phe Tyr Lys Gln Lys Val
305                 310                 315                 320

Gly Asp Val Leu Leu Thr Tyr Glu Asn Glu Val Ile Leu Thr Asn Glu
            325                 330                 335

Val Tyr Gly Asp Lys Ala Leu Pro Tyr Leu Val Pro Ser Tyr Asn Ile
            340                 345                 350

Arg Ile Glu Cys Pro Leu Ala Leu Val Asp Lys Val Val Asp Ala Arg
            355                 360                 365

Gly Pro Glu Val Arg Glu Ala Ala Ser Glu Phe Cys Arg Phe Leu Phe
370                 375                 380

Thr Pro Ala Ala Gln His Glu Phe Ala Arg Leu Gly Phe Arg Val Asn
385                 390                 395                 400

Pro Arg Thr Cys Lys Glu Val Ala Ala Gln Gln Thr Gly Leu Pro Pro
            405                 410                 415

Ala Asn Leu Trp Gln Val Asp Lys Glu Leu Gly Gly Trp Ala Ala Ala
            420                 425                 430

Gln Lys Lys Phe Phe Asp Ala Gly Ala Ile Leu Asp Asp Ile Gln Ser
            435                 440                 445

Ala Val Gly Lys Leu Arg Val Glu Gln Arg Lys Ala Ala Gln Ala Ala
            450                 455                 460

Ala Arg Arg
465
```

MODULATION OF SULFATE PERMEASE FOR PHOTOSYNTHETIC HYDROGEN PRODUCTION

CROSS-REFERENCE

This application is a continuation-in-part of pending application Ser. No. 10/350,298 filed Jan. 22, 2003 which application claims the benefit of priority to U.S. Provisional Application No. 60/354,760, filed Feb. 4, 2002, and U.S. Provisional Application No. 60/377,902, filed May 2, 2002, all of which applications are incorporated herein by reference.

GOVERNMENT RIGHTS

The United States Government may have certain rights in this application pursuant to Grant FD-2002-35100-12278-MELI-08/04 and 1998-35100-6148, awarded by the USDA-NRI Competitive Grant.

FIELD OF THE INVENTION

The invention relates generally to the field of hydrogen gas generation and to genetically modified algae that generate hydrogen gas under substantially anaerobic conditions in the presence of light and a media containing sulfur.

BACKGROUND

It has been known for years that some algae and bacteria naturally produce small amounts of hydrogen gas. The limiting factor is the fact that hydrogenase (the enzyme that catalyzes the hydrogen production reaction) is downregulated in the presence of oxygen. Because oxygen is a by-product of photosynthesis, it was necessary to shut down photosynthesis in the alga in an anaerobic environment for the production of greater amounts of hydrogen. This naturally was not a sustainable process, as the algae would initially produce hydrogen in response to the environmental stress and then die in short order. Several attempts were made to try and trick the algae into producing hydrogen without killing them in the process. For example, U.S. Pat. No. 4,442,211 disclosed a process for producing hydrogen by subjecting algae in an aqueous phase to light. Irradiation is increased by culturing algae which has been bleached during a first period of irradiation in a culture medium in a aerobic atmosphere until it has regained color and then subjecting this algae to a second period of irradiation wherein hydrogen is produced at an enhanced rate.

It was later discovered that in the absence of sulfur from the growth media, algae produce hydrogen gas. Sulfur is taken in by the cell through the chloroplasts as sulfate ions. CrcpSulP is a sulfate permease that migrates from the site of transcription in the nucleus to the chloroplasts. Its function as an enzyme is to facilitate sulfate uptake by the chloroplast. Sulfate availability to the chloroplast influences the rate of oxygenic photosynthesis. If the chloroplast is unable to intake an adequate amount of sulfate, then normal oxygen-producing photosynthesis is reduced. If the alga is in a substantially oxygen-free system in the presence of light, it begins photosynthesizing through an alternate cellular pathway, which leads to hydrogen production.

Under oxygenic photosynthesis conditions, and following a dark anaerobic induction, the activity of the hydrogenase is only transient in nature. It lasts from several seconds to a few minutes. This is because photosynthetic $O_2$ is a powerful inhibitor of the [Fe]-hydrogenase (Ghirardi et al. (2000) *Trends Biotechnol.* 12:506–511) and a positive suppressor of hydrogenase gene expression (Happe and Kaminski (2002) *Eur. J. Biochem.* 269(3):1022–1032).

Accordingly, there is a need for a process that obviates the need for removing sulfur from the algal growth medium, and thus alleviates cumbersome nutrient removal procedures or adding new algae to the culture. Further, there is a need for a process that permits a continuous and streamlined production of hydrogen from sunlight and water, while alleviating the need for the cells to go back to normal photosynthesis in order to recover lost metabolites such as starch and protein. Further, there is a need to produce hydrogen, making use as broad a portion of the solar spectrum as possible. Thus, there is a need to provide efficient hydrogen production in a closed system using green algae and photosynthetic purple bacteria. Additionally, there is a need for an assay to identify transgenic algae that have decreased ability to uptake sulfate. Using algae to produce hydrogen on a commercial scale has clear advantages for the environment, for reversing the effects of global warming, for decreasing dependence on a limited supply of energy such as oil, and for creating a nearly limitless source of energy. The present invention was developed in an attempt to meet these and other needs.

SUMMARY OF THE INVENTION

A process for sustained and continuous hydrogen production by algae is disclosed. The process comprises growing genetically modified green alga, which is a unicellular, photosynthesis, anoxygenic algae which is preferably *Chlamydomonas reinhardtii*. The algae is grown in an aqueous or solid medium under illuminated, substantially anaerobic conditions. The alga is genetically modified such that sulfur uptake mechanisms are downregulated by 50% or more preferably 75% or more (or eliminated) in the chloroplasts compared to the wild-type alga. The culture is sealed from atmospheric oxygen and incubated in light, whereby the algae's rate of light-induced oxygen production is equal to or less than its rate of respiration. The hydrogen gas that is generated from the culture is preferably collected and stored for use as a clean burning source of energy.

The invention further provides a sustainable and commercially viable integrated biological hydrogen production process. Photobiological hydrogen production by algae, utilizing the visible sunlight, is coupled to anaerobic bacterial hydrogen production, utilizing the near infrared region of the solar spectrum. Biomass accumulation in the course of photosynthesis by the two organisms is utilized in anaerobic fermentations for the further production of hydrogen and quantities of small organic acids. The organic acids serve as substrate for biomass and hydrogen production by the algae and photosynthetic bacteria.

Another aspect of the invention is a process whereby hydrogen gas is produced continuously by an algae where the sulfate permease gene has been downregulated, e.g. by insertion of antisense nucleotides into the genome, ablation of the gene itself, disruption of translation of the protein, or by selecting mutant strains that naturally have downregulated activity.

Another aspect of the invention is that the medium used to grow microorganisms need not be artificially depleted of sulfur.

Another feature of the invention is that the expression of the CrcpSulP gene is downregulated or preferably, eliminated.

A feature of the invention is that the algae are genetically altered by insertion of an antisense polynucleotide upstream or downstream of the CrcpSulP gene.

A further aspect of the invention is that the CrcpSulP gene is ablated.

An advantage of the invention is that the medium used can be more closely aligned with naturally occurring media as compared to prior processes that require nutrient depletion from the media.

Another aspect of the invention is that hydrogen is produced continuously, without having to restore viability to the alga in the culture after 80–100 hours.

A further aspect of the invention is an assay for screening algae cells transformed by the antisense polynucleotide, or by ablation of a sulfate permease gene.

The isolated amino acid sequence of SEQ ID NO:1 is a novel sequence and an aspect of the invention. The term "isolated" is used herein to mean the protein is separated from its natural milieu such that the product of nature is not claimed as an invention here. The same is true with respect to the nucleotide sequences of SEQ ID NO:2 and SEQ ID NO:3.

Another feature of the invention is the genomic DNA sequence of SEQ ID NO:2, the cDNA sequence of SEQ ID NO:3 and the amino acid sequence of SEQ ID NO:1.

Other aspects of the invention comprise novel amino acid sequences with a high degree of homology to SEQ ID NO: 1, e.g., 90% or more homology, preferably 95% or more homology.

Still other aspects of the invention comprise nucleotide sequences, which hybridize to either SEQ ID NO:2 or SEQ ID NO:3.

These and other aspects, objects, advantages, and features of the invention will become apparent to those persons skilled in the art upon reading the details of the invention as more fully described below.

BRIEF DESCRIPTION OF THE DRAWINGS

FIG. 2 is a schematic drawing of a chloroplast sulfate permease (CrcpSulP) gene structure from the wild-type *Chlamydomonas reinhardtii*.

FIG. 3 is the amino acid sequence (SEQ ID NO:1) of *Chlamydomonas reinhardtii* sulfate permease where the underlined amino acids in the N-terminal region of the protein comprise the chloroplast transit peptide.

FIG. 4A and FIG. 4B, which together provide the complete nucleotide sequence (SEQ ID NO:2) coding for CrcpSulP including the introns and exons.

FIG. 5 is the nucleotide sequence (SEQ ID NO:3) for the full length cDNA of CrcpSulP having a total length of 1984 bp.

FIG. 7A is a schematic representation of the pJD67 insertion site in the rep55 genomic DNA and the isolation of a flanking genomic DNA segment by inverse PCR (iPCR). Plasmid pJD67, containing the ARG7 gene in the vector pBluescriptII KS+ (Stratagene), was used for the transformation of *C. reinhardtii* strain CC425. The restriction enzyme KpnI was used in the digestion of the genomic DNA. ScaI was used for the subsequent linearization of ligated KpnI genomic DNA fragments prior to iPCR reactions (see "Methods"). iPCR5'-iPCR3' and Nested5'-Nested3' represent the two sets of primers used in the first and second iPCR reactions, respectively. The 126 bp DNA fragment corresponds to the isolated genomic DNA of the flanking region.

FIG. 7B is a restriction map of the SacI 7 kb genomic DNA fragment. The location of the ORF is indicated. Gray shaded boxes represent exons and clear boxes represent introns. The arrow indicates the direction of the open reading frame (ORF) transcription.

FIG. 8A. Deduced amino acid sequence alignment and phylogenetic comparison of chloroplast sulfate permease genes from a variety of organisms. Deduced amino acid sequence alignment of sulfate permeases from *N. olivacea* (SEQ ID NO:10) *M. viride* (SEQ ID NO:11). *C. reinhardtii* (SEQ ID NO:12) and *C. vulgaris* (SEQ ID NO:13) (green algae), *Synechococcus* sp. PCC 7942(SEQ ID NO:14) (cyanobacterium), *M. polyrnorpha* (SEQ ID NO:15) (liverwort), and *B. halodurans* (SEQ ID NO:16) (a non-photosynthetic prokaryote). The alignment of the amino acid sequences was based on a ClustalW analysis.

FIG. 11A. Coomassie-stained SDS-PAGE profile of total protein extract (T), envelope membrane proteins (Env) and thylakoid membrane proteins (Thy). Total and thylakoid protein samples were loaded on an equal chlorophyll basis. Each protein sample contained 1 nmol of total chlorophyll. For the envelope membrane proteins, 6.25 micrograms of protein were used for loading and the subsequent analysis. FIG. 11B is a Western blot analysis of the above cellular fractions probed with specific polyclonal anti-CrcpSulP antibodies. Note the cross reaction with a ~37 kD polypeptide.

FIG. 12A shows the steady state level of CrcpSulP gene transcripts upon S-deprivation of *C. reinhardtii*. Samples were incubated in the absence of sulfate nutrients from the growth medium for 0, 6 or 24 h. Equal amounts of total RNA (30 microgram) from each sample were loaded on the agarose gel lanes prior to Northern blot analysis (upper panel). Ethidium bromide staining of rRNA (lower panel). FIG. 12B is a Western blot analysis of the above cellular fractions with specific anti-CrcpSulP polyclonal antibodies. Samples were loaded on an equal chlorophyll basis. Note the cross reaction with a ~37 kD polypeptide.

FIG. 14A shows Western blot analysis of the CrcpSulP protein and the wild-type with 400, 50 and 0 microM sulfate. FIG. 14B. Coomassie-stained SDS-PAGE profile of total protein extracts from wild-type and asulp29. FIG. 14C. Western blot analysis of the SDS-PAGE-resolved proteins shown in FIG. 14B.

FIG. 15A. Sulfate uptake experiments were carried out with cells grown under normal growth conditions (TAP with 400 microM sulfate in the medium). Aliquots were removed upon incubation for 0, 15, 30, 45, 60 and 90 min in the presence of $^{35}$S-sulfate. FIG. 15B. Radiolabeling ($^{35}$S-sulfate) of *C. reinhardtii* proteins as revealed by SDS-PAGE and autoradiography. Aliquots were removed from the labeling reaction mix at 0, 15, 30, 45, 60 and 90 min, respectively. Total cellular proteins were extracted, loaded on an equal cell basis and analyzed by SDS-PAGE. Air-dried polyacrylamide gels were exposed to X-ray film and the autoradiography of the $^{35}$S-label of proteins was recorded. The protein bands corresponding to RbcL, RbcS and D1 are indicated by arrows.

FIG. 18A. Absolute activity of oxygenic photosynthesis (P, open circles) and respiration (R, solid circles) in wild-type *C. reinhardtii* suspended in media lacking a source of sulfur. The rate of cellular respiration (R) was recorded in the dark, followed by measurement of the light-saturated rate of photosynthesis (P). Cultures at 0 h contained 2.2×10$^6$ cell ml$^{-1}$. FIG. 18B. Hydrogen gas production and accumulation by *C. reinhardtii* cells suspended in media lacking sulfur. Gases were collected in an inverted burette and measured from the volume of water displacement.

FIG. 21 cDNA sequence of Sulp2 gene encoding *Chlamydomonas reinhardtii* chloroplast sulfate transport system. cDNA sequence of a gene encoding a novel subunit of a chloroplast envelope-localized sulfate transport system. The translation start codon (ATG) and termination codon (TAG) are underlined.

FIG. 22 cDNA sequence of Sabc gene encoding *Chiamydomonas reinhardtii* chloroplast sulfate transport system. cDNA sequence of gene encoding a novel ATP-binding protein, Sabc. The translation start codon (ATG) and termination codon (TAA) are underlined.

FIG. 23 cDNA sequence of the Sbp gene encoding *Chlamydomonas reinhardtii* chloroplast sulfate transport system. cDNA sequence of a gene encoding a sulfate binding protein, Sbp. The translation start codon (ATG) and termination codon (TGA) are underlined.

FIG. 24 *C. reinhardtii* chloroplast Sulfate Permease Sulp2 amino acid sequence Protein sequence: 369 aa, chloroplast transit peptide 82 aa, mature protein: 287 aa.

FIG. 25 *C. reinhardtii* chloroplast ATP-binding protein Sabc_amino acid sequence Protein sequence 465 aa, chloroplast transit peptide 56 aa, mature protein 409 aa FIG. 26 *C. reinhardtii* sulfate binding protein Sbp_amino acid sequence Protein sequence: 467 aa FIG. 27 Function of the Chloroplast Sulfate Transport System in the green alga *Chlamydomonas reinhardtii*. Sulfate nutrients are taken up by the cell as sulfate anions through the plasma membrane sulfate transporter. Once inside the cytosol, sulfate anions are carried by the sulfate binding protein, Sbp, to the Chloroplast Sulfate Transport System in order for them to be transported through the envelope membrane into the chloroplast. The chloroplast sulfate transporter is composed of two transmembrane proteins: CrcpSulP and Sulp2, which form a dimeric complex integral to the chloroplast envelope; and the ATP-binding protein, Sabc, localized on the chloroplast side of the envelope. Binding of ATP to the Sabc protein causes a conformational change of the two transmembrane proteins, which opens a channel between them allowing the sulfate anions to pass through. Limitation of sulfate availability in the *C. reinhardtii* chloroplast, induced as a result of the application of antisense technology (or RNAi) to any of the genes coding for the above proteins, leads to hydrogen photo-production by the green alga chloroplast.

DESCRIPTION OF THE PREFERRED EMBODIMENTS

Figure 1:
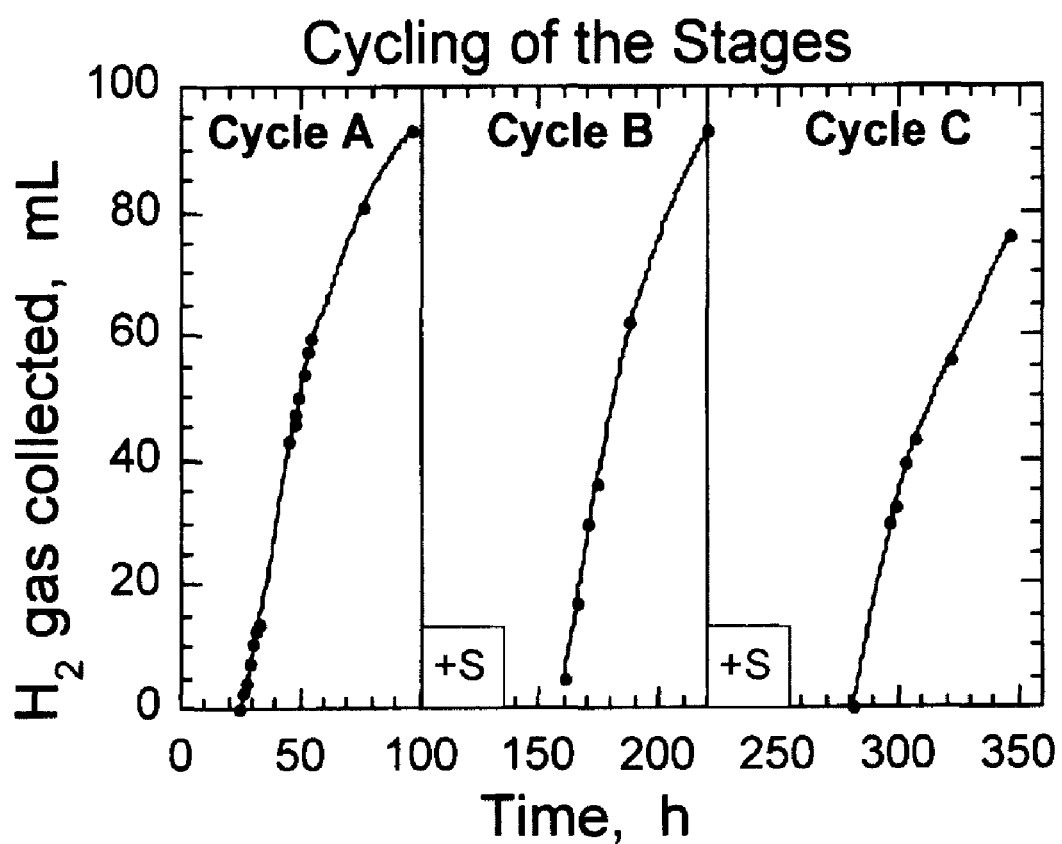
FIG. 1 is a schematic graph showing cycling stages of hydrogen production from native *Chlamydomonas reinhardtii* showing points of sulfur addition to the media.

Before the present invention is described, it is to be understood that this invention is not limited to a particular embodiment described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and" and "the" include plural referents unless the context clearly dictates otherwise. Thus, for example, reference to "a cell" includes a plurality of such cells and reference to "the fermentation" includes reference to one or more fermentation steps and equivalents thereof known to those skilled in the art, and so forth.

DEFINITIONS

Algae, alga or the like, refer to plants belonging to the subphylum Algae of the phylum Thallophyta. The algae are unicellular, photosynthetic, anoxygenic algae and are non-parasitic plants without roots, stems or leaves; they contain chlorophyll and have a great variety in size, from microscopic to large seaweeds. Green algae, belonging to Eukaryota—Viridiplantae-Chlorophyta—Chlorophyceae, is a preferred embodiment of the invention, with *C. reinhardtii*, belonging to Volvocales—Chlamydomonadaceae, as the most preferred embodiment. However, algae useful in the invention may also be blue-green, red, or brown, so long as the algae is able to produce hydrogen.

"Hybridization" refers to the association of two nucleic acid sequences to one another by hydrogen bonding. Two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See, Sambrook, et al., Molecular Cloning: A Laboratory Manual, 2nd Ed. (1989), Volume 2, chapter 9, pages 9.47 to 9.57. The hybridization may be under conditions considered conventional in the field.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5.times.SSC, 0.1% SDS, 0.25% milk, and no formamide; or 30% formamide, 5.times.SSC, 0.5% SDS). Moderate stringency hybridization conditions correspond to a higher $T_m$, e.g., 40% formamide, with 5.times. or 6.times.SCC. High stringency hybridization conditions correspond to the highest $T_m$, e.g., 50% formamide, 5.times. or 6.times.SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2.times.SSC, at 42° C. in 50% formamide, 4.times.SSC, or under conditions that afford levels of hybridization equivalent to those observed under either of these two conditions.

"Downregulation" refers to a decrease in the level of activity compared to the wild-type activity level. Preferred reductions in activity are at least 20%, preferably 40%, more preferably 50%, even more preferably 70%, and most preferred is 90% and above.

"Polynucleotide" and "nucleic acid" as used interchangeably herein refer to an oligonucleotide, nucleotide, and fragments or portions thereof, as well as to peptide nucleic acids (PNA), fragments, portions or antisense molecules thereof, and to DNA or RNA of genomic or synthetic origin, which can be single- or double-stranded, and represent the sense or antisense strand. Where "polynucleotide" or "nucleic acid" is used to refer to a specific polynucleotide sequence (e.g., encoding a CrcpSulP gene), the terms are meant to encompass polynucleotides that encode a polypeptide that is functionally equivalent to the recited polypeptide, e.g., polynucleotides that are degenerate variants, or polynucleotides that encode biologically active variants or fragments of the recited polypeptide.

By "antisense polynucleotide" is meant a polynucleotide having a nucleotide sequence complementary to a given polynucleotide sequence including polynucleotide sequences associated with the transcription or translation of the given polynucleotide sequence (e.g., a promoter), where the antisense polynucleotide is capable of hybridizing to a polynucleotide sequence. Of particular interest are antisense polynucleotides capable of inhibiting transcription and/or translation, either in vitro or in vivo.

"Polypeptide" as used herein refers to an oligopeptide, peptide, modified polypeptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but is meant to encompass analogues, degenerate substitutions, etc.

The nucleic acids of the invention also include naturally occurring variants of the nucleotide sequences, e.g., degenerate variants, allelic variants, etc. Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25–30% base pair mismatches relative to the selected nucleic acid probe. In general, allelic variants contain 15–25% base pair mismatches, and can contain as few as even 5–15%, or 2–5%, or 1–2% base pair mismatches, as well as a single base-pair mismatch.

As used herein the term "isolated" is meant to describe a compound of interest (e.g., either a polynucleotide or a polypeptide) that is in an environment different from that in which the compound naturally occurs e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

The use of the word "culture" is meant to refer to the propagation of living cells in media that is conducive to growth under the appropriate environmental conditions. The most common media include broths, gelatin, and agar, all of which will include sulfur as a component. The culture may be solid or liquid. Culturing may be done on a commercial scale, or in a single Petri dish.

"Modulation" is meant to refer to the alteration of activity level for the CrcpSulP protein, specifically in response to the genetic modification of the genome by addition of an antisense strand, or by knocking out the activity of the protein at the transcription or translation level.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates, which may need to be independently confirmed.

OVERVIEW OF THE INVENTION

The cycling of stages in a discontinuous green alga hydrogen production is shown in FIG. 1. Reversibility and reproducibility of the S-removal and hydrogen production sequence of events was demonstrated by cycling a single C. reinhardtii culture between the two stages (oxygenic photosynthesis in the presence of sulfur nutrients (+S) and hydrogen production in its absence) for up to three full cycles. At the end of hydrogen production in cycle A, the culture was supplemented with inorganic S (t=100 h).

It has been known for decades that many species of algae and bacteria give off small amounts of hydrogen. The problem from a commercial perspective is hydrogenase, the enzyme that produces hydrogen, is active only in the absence of oxygen. Because the hydrogenase pathway shuts down in the presence of oxygen, it does not function during photosynthesis. See, Melis and Happe, *Plant Physiol*. 127: 740–748 (November 2001).

*Chlamydomonas* is a genus of unicellular green algae (*Chlorophyta*) that is found all over the world. More than 500 different species of *Chlamydomonas* are known, but the most widely used laboratory species is *Chlamydomonas reinhardtii*. *C. reinhardtii*, like other photosynthetic organisms, require several macronutrients taken from the surrounding media for survival, including potassium, calcium, and sulfur. Sulfur is absorbed into the cell membrane of the chloroplast as sulfate ions, and is utilized as a component of two amino acids and is a component of many enzymes and proteins.

Removal of sulfur from the growth medium of green algae alters the photosynthesis pathway and causes the production of hydrogen gas in the presence of light. However, such removal of a nutrient on a commercial scale is unwieldy and costly in mass cultures of algae where thousands or millions of gallons of media are involved. Moreover, green alga hydrogen production upon sulfur removal is a discontinuous process at best because of the quick demise of the algae, which must be either replenished in the culture media by addition of sulfur, or new algae must be added to the existing sulfur-less media. See, for example, US 2001/0053543 A1 and Melis et al. (January 2000) *Plant Physiol.* 122:127–135.

The regulation of endogenous substrate catabolism and the attendant supply of electrons to the electron transport chain of photosynthesis form an aspect of the invention. Whereas rates of water oxidation by the photosynthetic apparatus can be measured continuously and precisely, measurements of electron transport supported by endogenous substrate catabolism and NAD(P)H-plastoquinone oxidoreductase activity are more difficult to make. Hydrogen photoproduction with anaerobically-incubated and DCMU-poisoned chloroplasts (Florin et al. (2001), supra) suggests that, initially, substantial rates of hydrogen production can be detected. However, this process could not be sustained for significant periods of time (Zhang et al. (2002) *Planta* 214(4):552–561). The present invention shows this is a result of a limitation in the capacity of the electron transport reactions associated with the NAD(P)H-plastoquinone oxidoreductase activity. The present invention provides endogenous starch, protein and lipid catabolism to feed electrons into the plastoquinone pool, thus contributing to hydrogen photoproduction.

In one aspect of the invention, the alga, which is genetically modified to downregulate expression of sulfate permease, is cultured with *Rhodobacter sphaeroides*, an anaerobic photosynthetic bacterium that uses sunlight to produce hydrogen via the nitrogenase/hydrogenase enzymic system. Fermentative processing of the *Chlamydomonas/Rhodobacter* biomass via *Clostridium* sp. further enhances the yield of biological hydrogen production.

Hydrogen production at significant rates can occur in certain unicellular green algae (e.g., *Chlamydomonas*) and anaerobic fermentative bacteria (e.g., *Clostridium*), catalyzed by an [Fe]-hydrogenase (Melis and Happe (2001) *Plant Physiol.* 127:740–748). Anaerobic photosynthetic bacteria (e.g., *Rhodobacter*) can produce hydrogen by means of a nitrogenase/hydrogenase enzyme.

Hydrogen gas is produced in algae with the help of a hydrogenase enzyme. The monomeric form of the hydrogenase enzyme belongs to the class of [Fe]-hydrogenases (Voordouw et al. (1989) *J. Bacteriol.* 171:3881–3889; Adams, M. (1990) *Biochim. Biophys. Acta* 1020:115–145; Meyer and Gagnon (1991) *Biochem.* 30:9697–9704; and Happe et al. (1994) *Eur. J. Biochem.* 222:769–774), and is encoded in the nucleus of the unicellular green algae. However, the mature protein is localized and functions in the chloroplast stroma. Light absorption by the photosynthetic apparatus is essential for the generation of molecular hydrogen since light-energy facilitates the oxidation of water molecules, the release of electrons and protons, and the endergonic transport of these electrons to ferredoxin. The photosynthetic ferredoxin (PetF) serves as the physiological electron donor to the [Fe]-hydrogenase and, therefore, links the soluble [Fe]-hydrogenase to the electron transport chain in the green alga chloroplast (Florin et al. (2001) *J. Biol. Chem.* 276:6125–6132). Absence of $CO_2$ enhances the light-driven hydrogen production, suggesting a competition for electrons between the $CO_2$ fixation and the hydrogen production processes (Cinco et al. (1993) *Photosynth. Res.* 38:27–33).

Fermentative bacteria do not utilize the energy of the sun in the process of hydrogen production. They depend solely on the catabolism of organic matter, which must be supplied in the growth medium. Hydrogen is the end-product of their anaerobic metabolism. Anaerobic photosynthetic bacteria are photoheterotrophs that can grow anaerobically and produce hydrogen from small organic acids (Warthmann et al. (1993) *Appl. Microbiol. Biotechnol.* 39:358–362). Most of these photosynthetic bacteria are nitrogen fixing microorganisms, utilizing the enzyme nitrogenase/hydrogenase, which catalyzes the reduction of molecular $N_2$ to $NH_3$. However, the simultaneous evolution of hydrogen by this enzyme is inherent in the process (Hall et al. (1995) *Photosynth. Res.* 46:159–167). In the absence of $N_2$ gas, the enzyme simply reduces protons ($H^+$) to hydrogen gas according to the equation $8H^+ + 8e^- + 16ATP \rightarrow 4\text{hydrogen} + 16ADP + 16Pi$ (1).

Infrared light, usually absorbed by these microorganisms, plays a critical role in the catalysis of this reaction as photosynthesis in these organisms generates the ATP needed to drive the hydrogen production reaction forward (Equation 1). Anaerobic photosynthetic bacteria, utilizing infrared radiation and small organic acids, can achieve high yields of hydrogen production. However, solar conversion efficiencies are low due to the high energetic demand of 4 ATP/hydrogen (Equation 1) and the very low intensity for the saturation of their photosynthesis, which prevents efficient utilization of solar irradiance (Rocha et al. (2001) in: Bio-Hydrogen II. An Approach to Environmentally Acceptable Technology, Miyaki et al., Eds., Elsevier Science, New York).

Algae have the advantage of being able to utilize the visible region of the spectrum in photosynthesis to oxidize water molecules. By this pathway, the algae may extract electrons ($e^-$) and protons ($H^+$) from an abundant supply. Moreover, via photosynthetic electron transport in their chloroplasts, they can recombine these electrons ($e^-$) and protons ($H^+$) to generate molecular hydrogen. Unlike fermentative and anaerobic photosynthetic bacteria, they are able to generate biomass from simple inorganic minerals and water by means of photosynthesis. They can operate with much better solar conversion efficiencies than the anaerobic photosynthetic bacteria. Given the more direct process of hydrogen production, and better solar conversion efficiencies, algae are thought to be more promising in long-term efforts of commercial hydrogen production. The present invention provides an integrated system for hydrogen production that may combine and exploit the strengths of genetically-modified algae, anaerobic photosynthetic bacteria and fermentative bacteria to achieve superior yields of hydrogen production.

DETAILED DESCRIPTION OF THE PREFERRED EMBODIMENTS

Through DNA insertional mutagenesis and screening, a *Chlamydomonas reinhardtii* chloroplast envelope-localized sulfate permease (CrcpSulP) was identified. Complete genomic DNA (bases 1 through 3873) of SEQ ID NO:2, cDNA (bases 1 through 1984) of SEQ ID NO:3 and protein sequences (amino acids 1 through 411) of SEQ ID NO:1 for this chloroplast-envelope localized sulfate permease are provided (Genbank Accession Number AF467891).

The gene structure and protein sequence of a *Chlamydomonas reinhardtii* chloroplast envelope-localized sulfate permease is shown in FIG. 2. The structure of the CrcpSulP sulfate permease gene showing the transcription start site and 5' UTR, five exons and four introns, plus the 3' UTR region is provided in FIG. 2. The complete DNA sequence (SEQ ID NO:2) is shown in FIG. 4. The amino acid sequence of *C. reinhardtii* sulfate permease (SEQ ID NO:1) is shown in FIG. 3. Underlined amino acids in the N-terminal region of the protein constitute the chloroplast transit peptide. The cDNA that encodes the peptide (SEQ ID NO:3) is provided in FIG. 5.

Based on a hydropathy plot of the mature protein, there are 7 predicted transmembrane helices and two extended hydrophilic loops. Sequence analysis and homology with sulfate permeases from *Marchantia polymorpha* (Ohyma et al. (1986) *Nature* 322:572–574), *Chlorella vulgaris* (Wakasugi et al. (1997) *Proc. Natl. Acad. Sci. USA* 94:5967–5972), *Synechococcus* sp PCC 7942 (Laudenbach and Grossman (1991) *J. Bacteriol.* 173:2739–2750), and *Synechocystis* sp. PCC6803 (Kohn and Schumann (1993) *Plant Mol. Biol.* 21:409–412; and Kaneko et al. (1996) *DNA Res.* 3:109–136) indicates a role for the CrSulP in sulfur uptake by the chloroplast in *Chlamydomonas reinhardtii*. The function of CrSulP is to regulate sulfate uptake by the chloroplast in this green alga. As discussed above, sulfate availability to the chloroplast regulates the rate of oxygenic photosynthesis. The application of antisense technology in *C. reinhardtii* to down-regulate CrSulP expression will provide a transformant with a capacity of photosynthesis that is less than that of cellular respiration. Such antisense transformants will grow in the presence of acetate (TAP media). Sealed cultures of such strains will become anaerobic in the light, as the capacity for respiration would be equal to or greater than the capacity of photosynthesis. In sealed cultures, such strains express the "hydrogenase pathway" and produce hydrogen upon illumination even when sulfate salts are abundant in the growth medium. The engineering of such *C. reinhardtii* strain permit a continuous hydrogen production process in the light and alleviate the need to perform nutrient replacement (S-deprivation) or nutrient calibration (S-titration) in order to induce the hydrogen production activity of the green algae.

Figure 6:
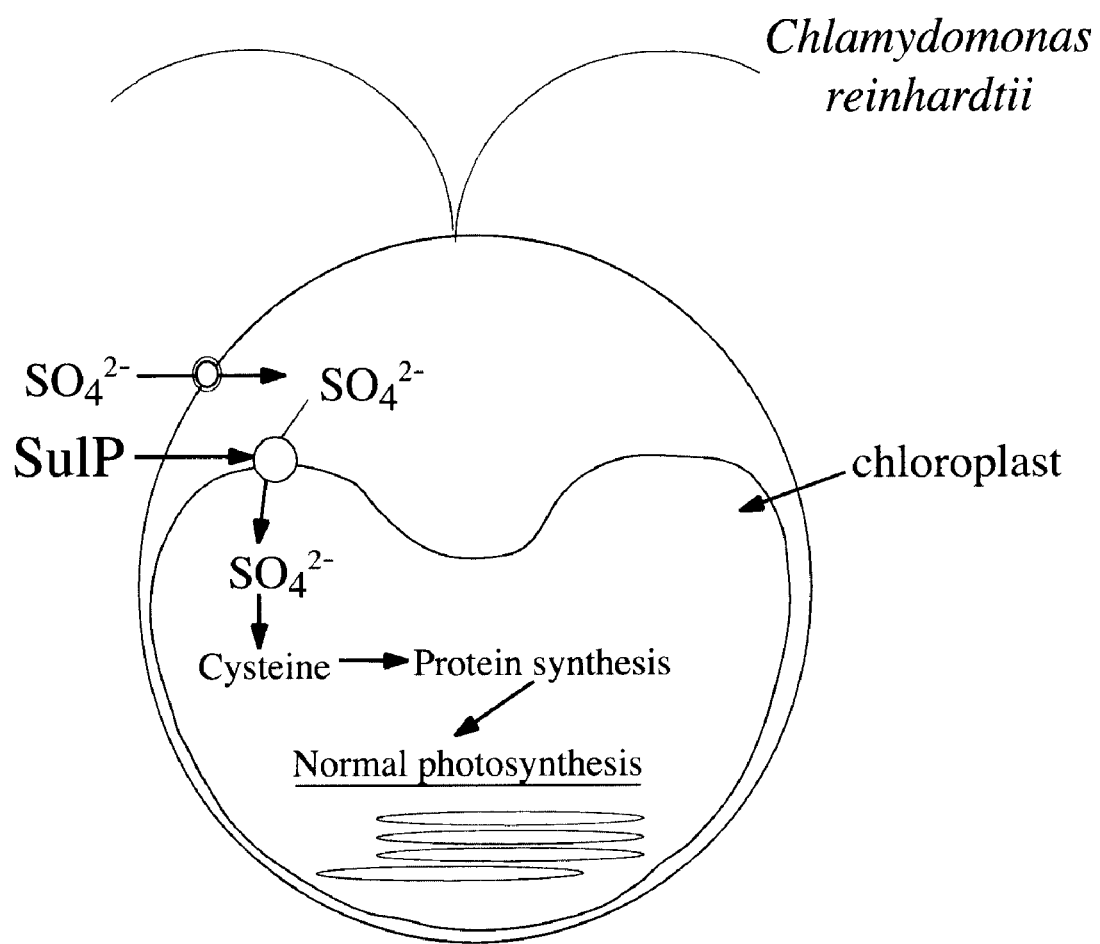
FIG. 6 is a schematic drawing showing the pathway of sulfate uptake by the cell and chloroplast in *Chlamydomonas reinhardtii* and pointing to the role of sulfur-mediated protein synthesis on the activity of oxygen-producing photosynthesis.

FIG. 6 is a schematic representation of the function of a sulfate permease (SuIP) in the transport of sulfate to the chloroplast of the green alga *Chlamydomonas reinhardtii*. Sulfur nutrients are transported from the cytosol, through a chloroplast-envelope localized sulfate permease (SuIP) into the chloroplast of the green algae where they are assimilated into cysteine, an amino acid. Cysteine and its derivative methionine are required for protein synthesis, which enables normal oxygenic photosynthesis, carbon accumulation and biomass increase.

The function of the sulfate permease is to direct sulfur uptake by the chloroplast. The sulfate permease gene can be manipulated by genetic transformation of the algae (antisense technology, knock-out, attenuation, etc.) to modulate the uptake of sulfate nutrients by the chloroplast. Such antisense transformants of green algae produce hydrogen in the light without having to remove sulfur nutrients from the growth medium.

The chlorophyll D1/32 kD reaction center protein of PSII accounts for less than 1% of the total thylakoid membrane protein. Yet, the rate of its biosynthesis is comparable to or exceeds that of the abundant large subunit of Rubisco in the chloroplast (Bottomley et al. (1974) *Arch. Biochem. Biophys.* 164:106–117; Eaglesham and Ellis (1974) *Biochim. Biophys. Acta* 335:396–407; Mattoo and Edelman (1987) *Proc. Natl. Acad. Sci. USA* 84:1497–1501). The reason for the high rates of de novo D1 biosynthesis is the frequent turnover of this protein, which is a consequence of a photo-oxidative damage in chloroplasts (Melis, A. (1999) *Trends Plant Sci.* 4:130–135). Investigations on the PSII damage and repair cycle (Guenther and Melis (1990) *Photosynth. Res.* 23:105–109) revealed that a constant supply of sulfate nutrients to the chloroplast is needed to sustain D1 biosynthesis and recovery of PSII from the photo-oxidative damage (Ohad et al. (1984) *J. Cell Biol.* 99:481–485; Vasilikiotis and Melis (1994) *Proc. Natl. Acad. Sci. USA* 91:7222–7226; Wykoff et al. (1998) *Plant Physiol.* 117:129–139). Upon S-deprivation, D1 biosynthesis slows-down and the PSII repair process is impeded. A gradual loss of PSII activity and loss of oxygen evolution is then manifested as photodamaged PSII centers accumulate in the chloroplast thylakoids (Wykoff et al. (1998), supra). Rates of photosynthetic oxygen evolution drop below those of mitochondrial respiration in the green algae (Melis et al. (2000) *Plant Physiol.* 122:127–135), causing anaerobiosis in a sealed culture (Ghirardi et al. (2000) *Trends Biotechnol.* 18:506–511). This condition is necessary and sufficient for the induction of the [Fe]-hydrogenase pathway in green algae (Melis and Happe (2001) *Plant Physiol.* 127:740–748), leading to sustained rates of hydrogen photoproduction by the culture. In this respect, changes in the expression of the CrcpSulP gene can downregulate sulfate nutrient uptake by the chloroplast in *C. reinhardtii*, leading to sustained rates of hydrogen photoproduction in sulfate replete media of this green alga. The latter can be achieved through antisense technology of the CrcpSulP gene, which lowers the sulfate uptake capacity of the cell. In this respect, induction of aryl-sulfatase (ARS) activity is a useful indicator of the sulfate limitation-state in the cell and, as such, it may be used as an assay in the high throughput screening of sulfate permease transformants. An increase of 5% or more of ARS activity is indicative of a lowered sulfate intake in the cell.

Methods for the regulation of gene expression are well-known in the art. Two principal methods are commonly employed, these being referred to loosely as "sense" and "antisense" regulation. In antisense regulation a gene construct is assembled which, when inserted into the genome of a cell, results in expression of a messenger RNA which is of complementary sequence to the messenger RNA initially transcribed by a target gene. The theory is that the complementary RNA sequences form a duplex thereby inhibiting translation to protein. The complementary sequence may be equivalent in length to the whole sequence of the target gene but a fragment is usually sufficient and is more convenient to handle.

In sense regulation, one or more copies of the target gene is inserted into the genome. Again, this may be a full length or partial sequence. A range of phenotypes is obtained from the cells in which the expression of the protein encoded by the target gene is inhibited. These cells exhibiting the activity of interest may then be identified and isolated using techniques known in the art. Sense regulation using partial sequences tends to favor inhibition. The mechanism for sense regulation is not well understood. Reference is made to European Patent Appl. No. 140,308 and U.S. Pat. No. 5,107,065, which are both concerned with antisense regulation and International Patent Application No. WO 90/12084, which describes sense regulation.

The application of antisense technology to the CrcpSulP gene renders obsolete the prior art sulfur-deprivation method in green alga hydrogen production, as it obviates the need to physically remove sulfur nutrients from the growth medium of the algae in order to induce the hydrogen production process. Moreover, application of such gene technology with the CrcpSulP gene permits a continuous hydrogen production with the green algae as opposed to the discontinuous process currently achieved. The genetically modified algae may also be used in the co-culture with bacteria for hydrogen production.

The gene structure of this CrcpSulP, including the transcription start site, 5' UTR, five exons, four introns and the 3' UTR region is shown in FIG. 2 and the complete DNA sequence (SEQ ID NO:2) as provided in FIG. 4. The amino acid sequence of the 411 amino acid precursor protein is provided as SEQ ID NO:1. Based on a hydropathy plot of the mature protein, there are 7 transmembrane helices and two extended hydrophilic loops. Sequence analysis and homology with sulfate permeases from *Marchantia polymorpha* (Ohyma et al. (1986) *Nature* 322:572–574), *Chlorella vulgaris* (Wakasugi (1997) *Proc. Natl. Acad. Sci. USA* 94:5967–5972), *Synechococcus* sp PCC 7942 (Laudenbach and Grossman (1991) *J. Bacteriol.* 173:2739–275), and *Synechocystis* sp. PCC6803 (Kohn and Schumann (1993) *Plant Mol. Biol.* 21:409–412; and Kaneko (1996) *DNA Res.* 3:109–136) indicated that the CrcpSulP protein regulates sulfur uptake by the chloroplast in *Chlamydomonas reinhardtii*.

Antisense Technology

Antisense molecules can be used to down-regulate expression of CrcpSulP polypeptide genes in cells. The antisense reagent may be antisense oligodeoxynucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Preferred sequence length is 10 to 3000 nucleotides. More preferred sequence length is 100–2000 nucleotides. Even more preferred sequence length is 600 to 1200 nucleotides. The most preferred sequence length is 800–1000 nucleotides. The length is governed by efficiency of inhibition, specificity, including absence of cross-reactivity, and the like. However, it has also been found that short oligonucleotides, of from 7 to 8 bases in length, can be strong and selective inhibitors of gene expression (see Wagner et al. (1996) *Nature Biotechnol.* 14:840–844).

A specific region or regions of the endogenous sense strand mRNA sequence is chosen to be complementary to the antisense sequence. Selection of a specific sequence for the oligonucleotide may use an empirical method, where several candidate sequences are assayed for inhibition of expression of the target gene in an in vivo model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. The sequence of the 5' flanking region may be utilized for promoter elements that provide for regulation in the chloroplasts where CrcpSulP polypeptides are expressed. The tissue specific expression is useful for determining the pattern of expression, and for providing promoters that mimic the native pattern of expression. Naturally occurring polymorphisms in the promoter region are useful for determining natural variations in expression.

Alternatively, mutations may be introduced into the promoter region to determine the effect of altering expression in experimentally defined systems. Methods for the identification of specific DNA motifs involved in the binding of transcriptional factors are known in the art, e.g., sequence similarity to known binding motifs, gel retardation studies, etc. For example, see Blackwell et al. (1995) *Mol. Med.* 1:194–205; Mortlock et al. (1996) *Genome Res.* 6:327–333; and Joulin and Richard-Foy (1995) *Eur. J. Biochem.* 232: 620–626.

The regulatory sequences may be used to identify cis acting sequences required for transcriptional or translational regulation of expression, and to identify cis-acting sequences and trans-acting factors that regulate or mediate expression. Such transcription or translational control regions may be operably linked to one of the subject genes in order to promote expression of the antisense CrcpSulP polypeptide.

The nucleic acid compositions of the subject invention may encode all or a part of the CrcpSulP polypeptides of the invention. Double or single stranded fragments of the DNA sequence may be obtained by chemically synthesizing oligonucleotides in accordance with conventional methods, by restriction enzyme digestion, by PCR amplification, etc. For the most part, DNA fragments will be at least 25 nt, usually at least 50 nt or 75 nt or 100 nt but may be as long as 200 nt, 240 nt, 270 nt, 300 nt, and even as long as 400 nt. Small DNA fragments are useful as primers for PCR, hybridization screening probes, etc. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of CrcpSulP gene expression in the sample.

The sequence of a CrcpSulP nucleic acid or gene, including any flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e., will differ by at least one amino acid, and may differ by at least one or two but not more than about ten amino acids. The sequence changes may be substitutions, insertions or deletions. Deletions may further include larger changes, such as deletions of a domain or an exon. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–539 (1985); and Prentki et al., *Gene* 29:303–313 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–596 (1992); Jones and Winistorfer, *Biotechniques* 12:528–530 (1992); Barton et al., *Nucl. Acids Res.* 18:7349–7355 (1990); Marotti and Tomich, *Gene Anal Tech* 6:67–70 (1989); and Zhu, *Anal. Biochem.* 177:120–124 (1989). Such mutated genes may be used to study structure-function relationships of CrepSulP family polypeptides or to alter properties of the protein that affect its function or regulation. Additionally, the gene expressing a sulfate permease can be ablated using the "knock out" technology as described in U.S. Pat. Nos. 5,464,764 and 5,487,992, all of which are incorporated herein by reference in their entirety, and specifically incorporated to disclose and describe methods of ablating endogenous genes.

Based on the above, it will be understood that reducing or eliminating sulfate uptake by the chloroplast enhances hydrogen production. Specifically, the sulfate uptake is decreased or eliminated by disrupting the sulfate permease enzyme in its activity level, by disrupting the gene's transcription to mRNA, or by disrupting the protein translation from the mRNA. Sulfate permease activity and/or its synthesis can be disrupted by a number of different mechanisms that can be used alone or in combination with each other. For example, an antisense polynucleotide may be added to the cell culture to hybridize with the mRNA transcript of the CrcpSulP gene. Alternatively, a gene expressing a sulfate permease can be disrupted by the application of antisense technology in *C. reinhardtii* to down-regulate CrcpSulP expression. This provides the subsequent generation of transformants with a capacity of photosynthesis that is less than that of cellular respiration. Such antisense transformants grow in the presence of acetate (TAP media). Sealed cultures of such strains become anaerobic in the light, as the capacity for respiration is equal to or greater than the capacity of photosynthesis.

Hydrogen Gas Production

In sealed and illuminated cultures, the genetically modified algae strains described above express the "hydrogenase pathway" and produce hydrogen continuously, even when sulfate nutrients are abundant in the growth medium. The genetic engineering of such algae strains, e.g., *C. reinhardtii*, permits a continuous hydrogen production process in the light as it obviates the need to perform nutrient replacement (S-deprivation) or nutrient calibration (S-titration) in order to induce the hydrogen production activity in the algae. When produced in commercially viable quantities, hydrogen can serve as a non-polluting and renewable fuel.

The alga used in the invention may be any alga capable of producing hydrogen. Preferably a green alga is used, and even more preferably *C. reinhardtii*. A blue-green alga (*Synechococcus* sp.) is also preferred in the invention. See, U.S. Pat. No. 4,532,210. However, any alga capable of hydrogen production would be useful in the invention.

The production of hydrogen is carried out in lighted conditions. Preferably the light is continuous, with sunlight as the source during daylight hours, and artificial illumination used at night, and in cloudy conditions. Sunlight may also be used alone, with no extra illumination provided at night, although this may decrease the yield of hydrogen.

The production of hydrogen is carried out in a substantially anaerobic environment. The oxygen may be forced out of the system by addition of helium gas, for example. Alternatively, and more preferably, the system may be initially closed from the external environment, without any removal of the oxygen. The lack of photosynthesis from the alga will naturally decrease the amount of oxygen present in the system over time such that the environment is substantially anaerobic, and efficient generation of hydrogen may then be effected.

The media used in the invention may be any of the standard commercial preparations used for culturing alga that also contain sulfur. Preferably, TAP media is used. The algae may be cultured in a liquid or solid media, with liquid media being preferred.

In the absence of sulfur, the rate of photosynthetic $O_2$ evolution drops below the rate of $O_2$ consumption by respiration. As a result, sealed cultures of algae become substantially anaerobic in the light. This induces the "Fe-hydrogenase" pathway of electron transport, which subsequently causes the alga to photosynthetically produce hydrogen gas. In the course of such hydrogen production, the algal cells consume significant amounts of internal starch and protein. Such catabolic reactions may sustain, directly or indirectly, the hydrogen production process. Profile analysis of selected photosynthetic proteins showed a precipitous decline in the amount of Rubisco as a function of time in S-deprivation, a more gradual decline in the level of photosystem (PS) II and PSI proteins, and change in the composition of the LHC-II. Increase in the level of the enzyme Fe-hydrogenase was noted during the initial stages of S-deprivation (0–72 h) followed by a decline in the level of this enzyme during longer (t>72 h) S-deprivation times. Under S-deprivation conditions, electrons derived from a residual PSII water-oxidation activity feed into the Fe-hydrogenase pathway, thereby contributing to the hydrogen production process in algae. Interplay between oxygenic photosynthesis, mitochondrial respiration, catabolism of endogenous substrate, and electron transport via the Fe-hydrogenase pathway is essential for this light-mediated hydrogen production process.

It will be understood by those skilled in the art that interruption of any one of several different cellular mechanisms would disrupt normal photosynthesis. The disruption of normal oxygenic photosynthesis induces hydrogen production in an anaerobic environment. As a non-limiting example, a removal of sulfur from the chloroplast, caused by the application of antisense CrcpSulP gene technology, disrupts photosynthesis and induces hydrogen production in the alga chloroplast.

A number of non-photosynthetic anaerobic bacteria can produce hydrogen upon fermentation of a variety of organic substrates. For example, *Enterobacter aerogenes* and *Clostridium beijerinckii* can produce hydrogen from glucose and starch (Taguchi et al. (1995) *Enzyme Microb. Technol.* 17:147–150; Taguchi et al. (1996) *J. Ferment. Bioeng.* 82:80–83; and Perego et al. (1998) *Bioproc. Eng.* 19:205–211). *Clostridium* sp. is known to convert cellulolytic materials into hydrogen. During such anaerobic fermentation and hydrogen production, small organic acids (glycolate, acetate, lactate, malate, etc.) accumulate in the growth medium as inevitable byproducts (Majizat et al. (1997) *Wat. Sci. Tech.* 36:279–286). Accumulation of small organic acids stops hydrogen production as it causes inhibition in the rate of metabolic fermentation and growth.

The system of the invention uses the accumulated excess biomass from a hybrid *Chlamydomonas/Rhodobacter* system as substrate for hydrogen production by non-photosynthetic anaerobic bacteria. The invention establishes the operation of such a fermentation system, to be supported by green alga and photosynthetic bacterial biomass. *Clostridium* sp. strain no. 2 were found to be the most suitable for the anaerobic fermentation of cellulose and other polysaccharides that will be generated from a hybrid *Chlamydomonas/Rhodobacter* system.

Figure 20:
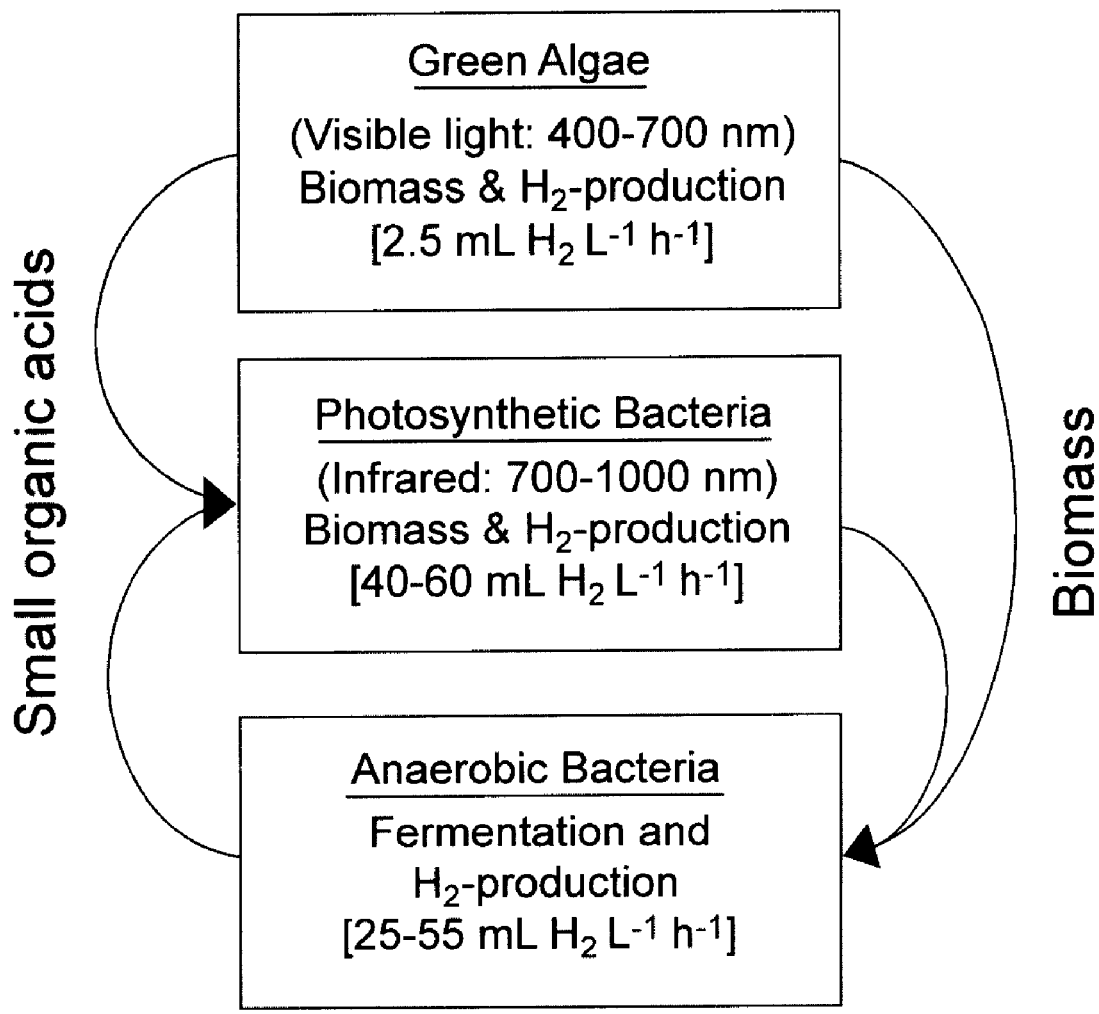
FIG. 20. Integrated three-organism system for commercial hydrogen production. Green algae and photosynthetic bacteria co-cultivated in the same photobioreactor, thereby minimizing facility costs. Photobioreactor surface area for the capturing of solar irradiance is a requirement for this stage. Anaerobic bacteria can be cultivated in traditional fermentors where surface area is not a requirement. Integration of the three processes is expected to significantly prolong high yields of hydrogen production by the three processes.

In turn, small organic acids, the byproduct of the *Clostridium* fermentation are employed as the source of organic carbon needed to sustain growth and hydrogen production in the *Chlamydomonas/Rhodobacter* hybrid system (FIG. 20).

The process of photosynthetic hydrogen production with electrons derived from water, which is also referred to as "biophotolysis" (Miura (1995) *Process Biochem.* 30:1–7; and Benemann, J. R. (1996) *Nature Biotechnol.* 14:1101–1103) entails water oxidation and a light-dependent transfer of electrons to the [Fe]-hydrogenase, leading to the synthesis of molecular hydrogen. Electrons are generated upon the photochemical oxidation of water by PSII. These are transferred through the thylakoid membrane electron-transport chain and, via PSI and ferredoxin, are donated to the HC cluster of [Fe]-hydrogenase (Florin et al. (2001), supra). Protons ($H^+$) are the terminal acceptors of these photosynthetically generated electrons in the chloroplast. The process does not involve $CO_2$ fixation or energy storage into cellular metabolites. This process results in the simultaneous production of $O_2$ and $H_2$ with an $H_2:O_2=2:1$ ratio (Spruit, C. P. (1958) *Landbouwhogeschool Wageningen* 58:1–17; and Greenbaum et al. (1983) *Photochem. Photobiol.* 37:649–655). This mechanism generates hydrogen continuously and efficiently through the solar conversion ability of the photosynthetic apparatus.

The metabolic and hydrogen production properties of the organisms described above indicate the design of an integrated system in which oxygenic and anoxygenic photosynthesis are employed in tandem to harvest the visible and infrared energy of the sun and to convert this solar energy into hydrogen energy. Hydrogen can be collected, while biomass extracted from this hybrid process can be converted, through the use of industrial enzymes, into cellulolytic material composed of hydrolysates of polyglucose and protein, which can directly feed anaerobic bacterial fermentations. Such nonphotosynthetic anaerobic bacterial fermentations would generate hydrogen and a variety of small organic acids. The latter can feed back into the anoxygenic photosynthetic bacterial hydrogen production reactions (FIG. 20). Such integrated systems would constitute a high yield, sustainable and viable hydrogen production process.

Isolation and Characterization of the CrcpSulP Gene

Figure 7A:
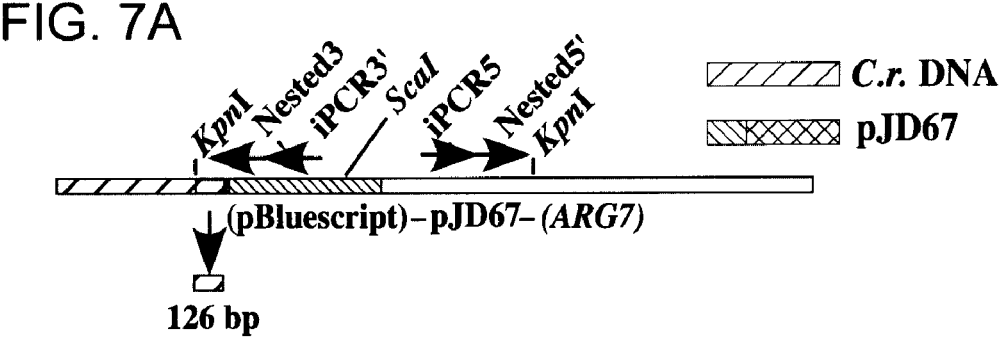
FIGS. 7A and 7B. Mapping and characterization of pJD67 insertion site in *Chlamydomonas reinhardtii*.
Figure 7B:
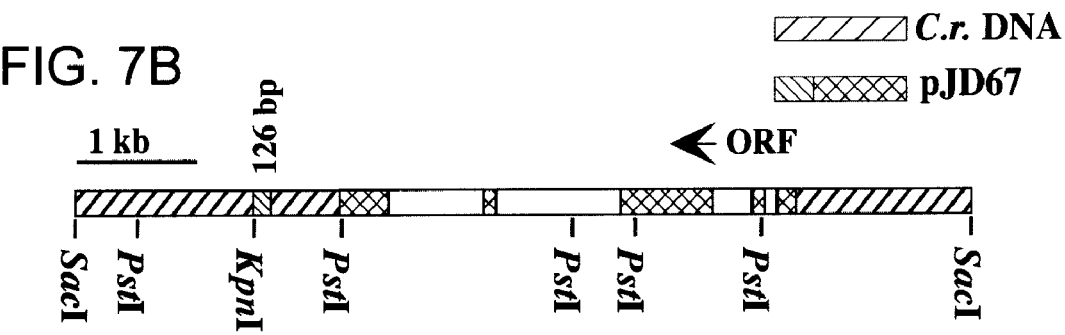

A photosynthesis mutant, rep55, was initially isolated by screening a library of DNA insertional transformants of *Chlamydomonas reinhardtii* for the isolation of PSII repair-aberrant strains. The screening protocol for the isolation of repair-aberrant strains was reported earlier (Zhang et al. (1997) *Photosyn. Res.* 53:173–184). This transformant showed a low yield of variable Chl fluorescence in vivo, low light-saturated rates of photosynthesis, and low steady-state levels of D1 protein in its thylakoid membranes. To identify the gene(s) affected by the ARG7 insertion in rep55, a molecular characterization of the insertion site and cloned the genomic DNA regions that were flanking the insertion was conducted. The upstream flanking region of the insertion site in rep55 was cloned first, by using an inverse PCR (iPCR) approach. The iPCR was carried out using the KpnI-digested rep55 genomic DNA as a template (see schematic in FIG. 7A). After self-ligation, and following linearization of the ligated DNA, two sets of primers were used (iPCR5'/iPCR3' & Nested5'/Nested3') to amplify a specific iPCR product, as shown in FIG. 7A. Sequence analysis showed that the iPCR product contained a 126 bp fragment of the *C. reinhardtii* genomic DNA. This 126 bp flanking region DNA fragment was subsequently used as a probe for the screening of a *C. reinhardtii* BAC genomic library (Incyte Genomics, Inc). Two BAC clones (20 g15 and 9b18) that hybridized strongly to the 126 bp probe were identified. Analysis of these BAC clones, by restriction digestion and by using the 126 bp fragment as a probe, showed common restriction fragments and identical hybridization patterns. This indicated that each of these BAC clones harbored the same region of the *C. reinhardtii* genomic DNA that contained the 126 bp sequence. Moreover, Southern hybridization analyses of the two BAC clones and of wild-type genomic DNA, with the 126 bp DNA fragment as a probe, yielded identical hybridization patterns, indicating that this region is unique in the *C. reinhardtii* genome (restriction map shown in FIG. 1B).

Through restriction mapping analysis of the *C. reinhardtii* genomic DNA, the 126 bp DNA fragment was localized on a SacI fragment of about 7 kb. After sequencing of the SacI fragment, an ORF was identified in the region adjacent to the 126 bp sequence. Analysis of the nucleotide sequence of this ORF did not reveal any similarity with other known DNA sequences. However, a deduced amino acid sequence from this ORF indicated similarity with sulfate permeases from a diversity of bacteria and alga (Altschul et al. (1997) *Nucl. Acids Res.* 25:3389–3402). In particular, high similarity was found with the deduced amino acid sequence of chloroplast sulfate permeases from green algae such as *Mesostigma viride* (Lemieux et al. (2000) *Nature* 403:649–652), *Nephroselmis olivacea* (Tunnel et al. (1999) *Proc. Natl. Acad. Sci. USA* 96:10248–10253), *Chlorella vulgaris* (Wakasugi et al. (1997) *Proc. Natl. Acad. Sci. USA* 94:5967–5972), the colorless alga *Prototheca wickerhamii* (Knauf and Hachtel (1999) Genbank Accession No. AJ245645) and the liverwort *Marchantia polymorpha* (Ohyma et al. (1986) *Nature* 322: 572–574). This type of sulfate pernease is of prokaryotic origin, as high similarity was also found with the sulfate permease from the cyanobacteria *Synechococcus* sp. PCC7942 (Laudenbach and Grossman (1991) *J. Bacteriol.* 173:2739–2750), *Synechocystis* sp. PCC6803 (Kaneko et al. (1986) *DNA Res.* 3:109–136; and Kohn and Schumann (1993) *Plant Mol. Biol.* 21:409–412), and the sulfate ABC transporter permease from various bacteria (Sirko et al. (1990) *J. Bacteriol.* 172:3351–3357 and Takami et al. (2000) *Nucl. Acids Res.* 28:4317–4331). It became apparent, therefore, that this *C. reinhardtii* ORF coded for a sulfate permease of prokaryotic origin.

Figure 8B:
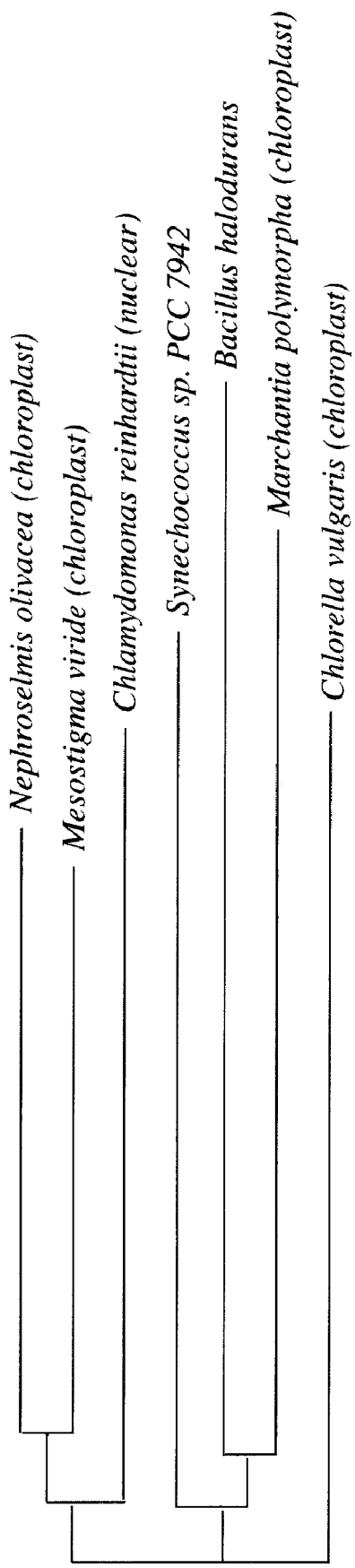
FIG. 8B. Phylogenetic tree of the above sulfate permeases based on the amino acid sequence comparisons shown above.

The deduced amino acid sequence of the gene showed close to 60% identity (80% similarity) with its green alga counterparts, while no significant similarity could be found at the DNA nucleotide sequence level. The ClustalW alignment of the deduced amino acid sequence of the sulfate permease from various green algae, including *C. reinhardtii*, as well as *Synechococcus* sp. PCC7942, *Bacillus halodurans* (Takami et al. (1999) *Extremophiles* 3:21–28) and *Marchantia polymorpha* is shown in FIG. 8A. Noteworthy in the *C. reinhardtii* protein is the rather extended N-terminus, which includes an apparent transit peptide and other features unique to this green alga sulfate permease. The phylogenetic tree of these proteins is also shown (FIG. 8B). This analysis revealed that, although the sulfate permease gene in *C. reinhardtii* has migrated from the chloroplast to the nuclear genome, the amino acid sequence of its protein remained closer to that of the ancestral green alga (*Mesostigma viride*) than the chloroplast-encoded homologue in *Chlorella vulgaris*. The latter has apparently diverged further from its ancestral sequence.

Structure of a Chloroplast Sulfate Permease Gene (CrcpSulP)

Figure 9:
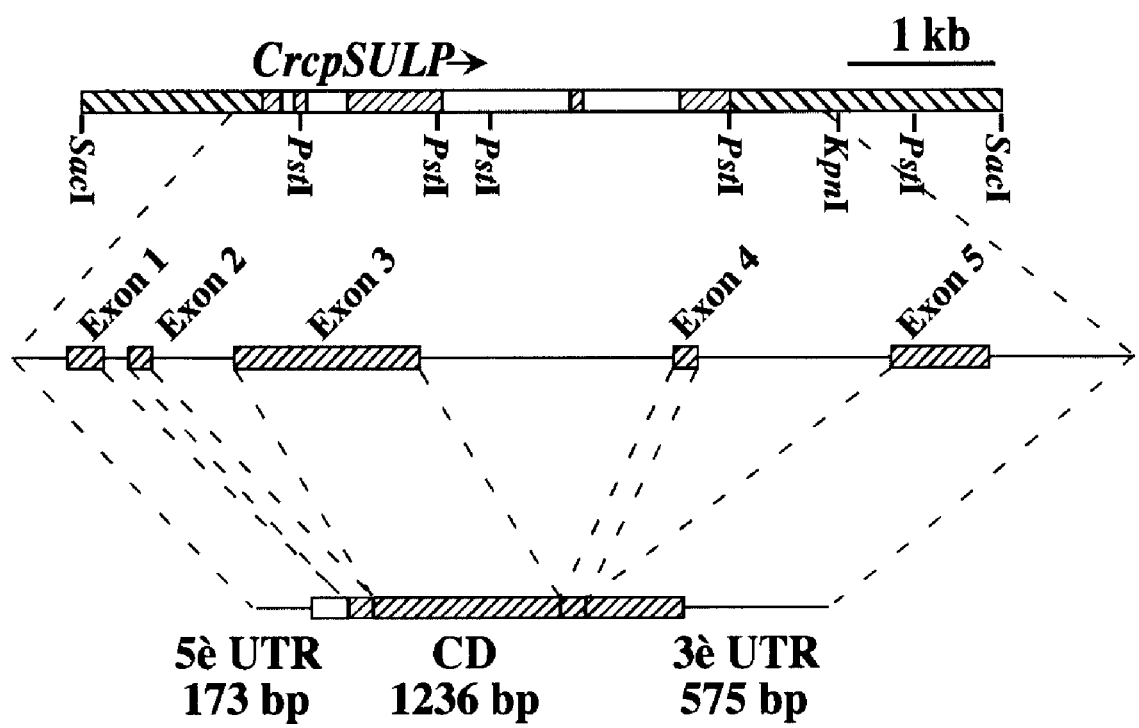
FIG. 9. Structure of the CrcpSulP gene. The CrcpSulP gene contains 5 exons and 4 introns in the coding region. The exons are represented by gray-shaded boxes. The size of the 5' UTR (173 bp), the coding region (CD: 1236 bp) and the 3' UTR (575 bp) are also indicated.
Figure 10:
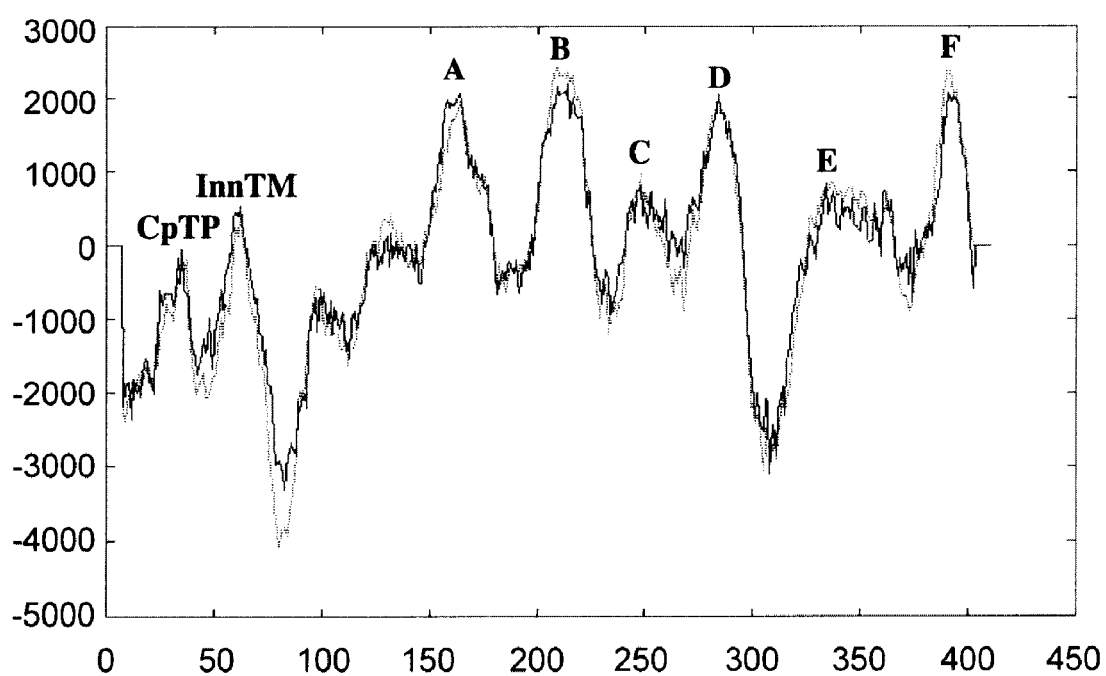
FIG. 10 shows a hydropathy plot of the CrcpSulP protein. The predicted chloroplast transit peptide (CpTP) is indicated. Seven transmembrane helices of the mature protein are indicated as InnTM and A–F.

The known chloroplast sulfate permease genes of algae are encoded in the chloroplast genome, and none of these genes contain introns in their coding region. In this regard, the structure of the *C. reinhardtii* sulfate permease gene is noted by the presence of four introns in the coding region (Genbank Accession No. AF467891, FIG. 9). The position of the four introns was initially identified by sequence comparison with other intron-less homologous gene sequences and by a splice-site prediction analysis from the "Berkeley Drosophila Genome Project" web site (http://www.fruitfly.org/). The position of introns was subsequently confirmed upon comparison with the cDNA sequence of the sulfate permease (Genbank Accession No. AF482818, FIG. 9), generated by RT-PCR using specific sets of primers. The 5' and 3' UTR sequences of the cDNA were determined by 5' and 3' RACE (Rapid Amplification of cDNA Ends), respectively. This analysis revealed that the 5' and 3' UTR of the transcripts were 157 bp and 575 bp long, respectively. Analysis of the deduced amino acid sequence of the gene showed the presence of a putative chloroplast transit peptide of 54 amino acids in the N-terminal region (FIG. 3), predicted by both ChloroP and TargetP analysis (Emanuelsson et al. (1999) *Protein Sci.* 8:978–984). Hydropathy analysis of the protein by TMperd (Hofmann and Stoffel (1993) *Biol. Chem. Hoppe-Seyler* 374:166) revealed the presence of 7 transmembrane helices. A noticeably large hydrophilic loop could be identified between helices D and E, which is a typical feature of permeases belonging to the ABC (ATP-binding cassette) transporter family. In addition to the putative chloroplast transit peptide at the N-terminus, a unique structural feature of the N-terminal sequence of the mature *C. reinhardtii* protein was observed. It contained an additional short transmembrane domain, which is absent from its chloroplast-encoded counterparts, followed by a long hydrophilic region. Such structural feature may be related to the folding of the protein into the chloroplast envelope.

CrcpSulP Protein is Localized in the Chloroplast

Figure 11A:
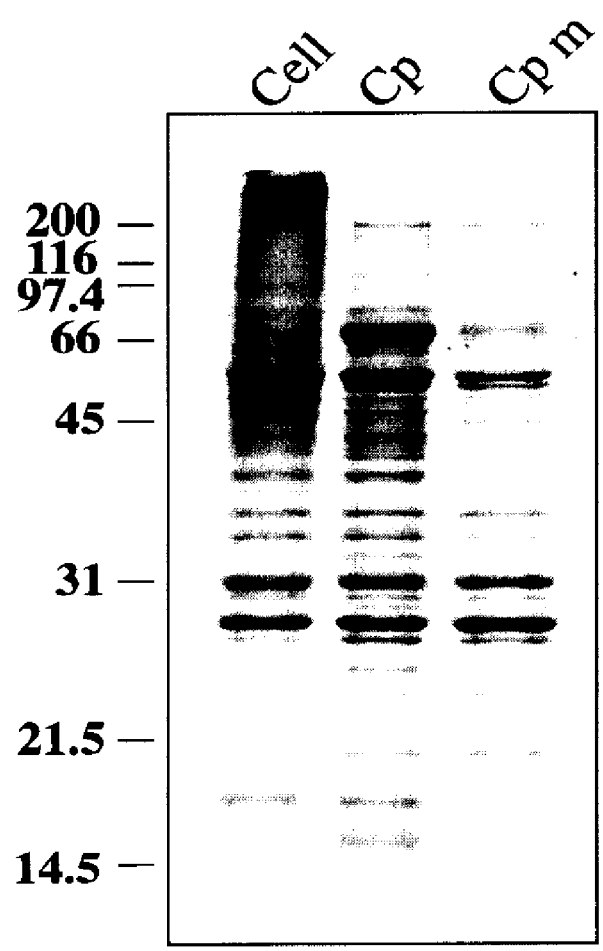
FIGS. 11A and 11B. Cellular localization of CrcpSulP protein.
Figure 11B:
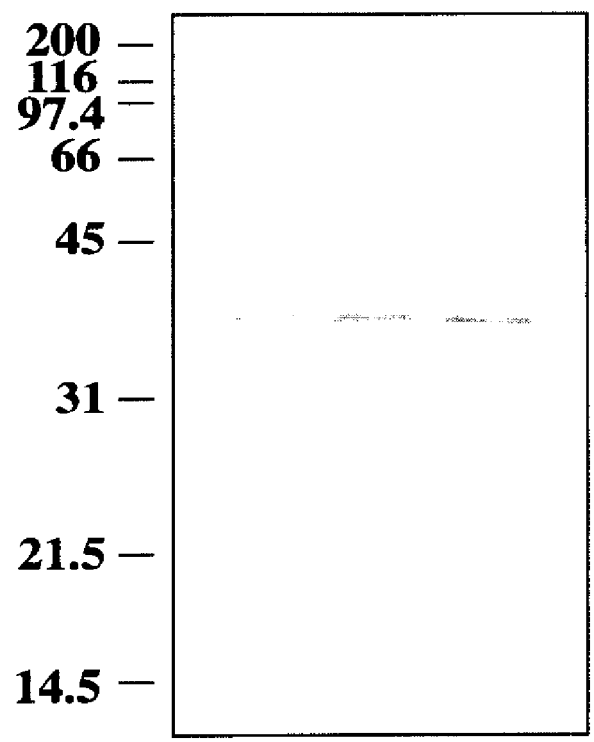

The high similarity of the CrcpSulP protein to other alga chloroplast sulfate permeases, which nevertheless are encoded by the chloroplast genome, and the presence of a predicted chloroplast transit peptide at the N-terminus of this protein, make it likely to be localized in the chloroplast envelope. Specific polyclonal antibodies were raised against an oligopeptide of the mature protein and used in Western blot analyses with different *C. reinhardtii* cellular fractions for the immuno-localization of the sulfate permease. Western blot analysis with total cellular protein extracts (FIG. 11B) showed a single antibody cross-reaction with a protein migrating to about 37 kD, which is smaller than the calculated molecular mass of the full length sulfate permease (411 amino acids =42 kD). However, a protein of 37 kD probably corresponds to the mature form of the sulfate permease, following excision of the predicted chloroplast transit peptide of 54 amino acids (357 amino acids=37.8 kD). On the basis of electrophoretic mobility, therefore, the antibodies appeared to specifically recognize the CrcpSulP protein. To strengthen the notion of an association of this protein with the chloroplast in *C. reinhardtii*, intact chloroplasts were isolated following a mild cell fractionation and Percoll gradient centrifugation (Mason et al. (1991) *Plant Physiol.* 97:1576–1580). FIG. 11A shows the Coomassie-stained SDS-PAGE profile of proteins associated with the isolated chloroplast protein fractions: total protein extracts (T), envelope proteins (Env) and thylakoid membrane proteins (Thy). FIG. 11B shows the corresponding Western blot analysis and immunodetection by using anti-SuIP polyclonal antibodies. The anti-SuIP antibodies specifically cross-reacted with a single protein band from the envelope protein extract. No cross-reaction could be detected with thylakoid membrane proteins while a fainter cross-reaction was detected with the total protein extract. These results provided evidence for a chloroplast envelope localization of the SulP protein.

Sulfate Regulation and CrcpSulP Gene Expression

Figure 12A:
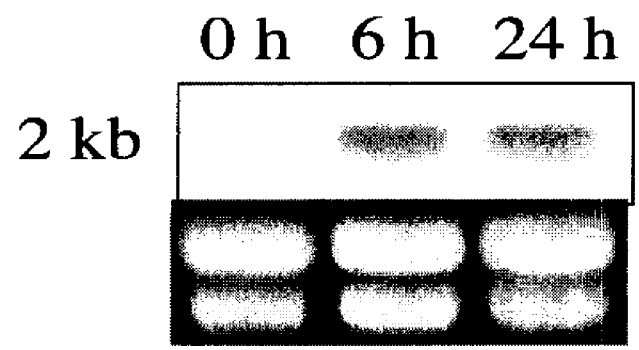
FIGS. 12A and 12B. Expression analysis of the CrcpSulP gene.
Figure 12B:
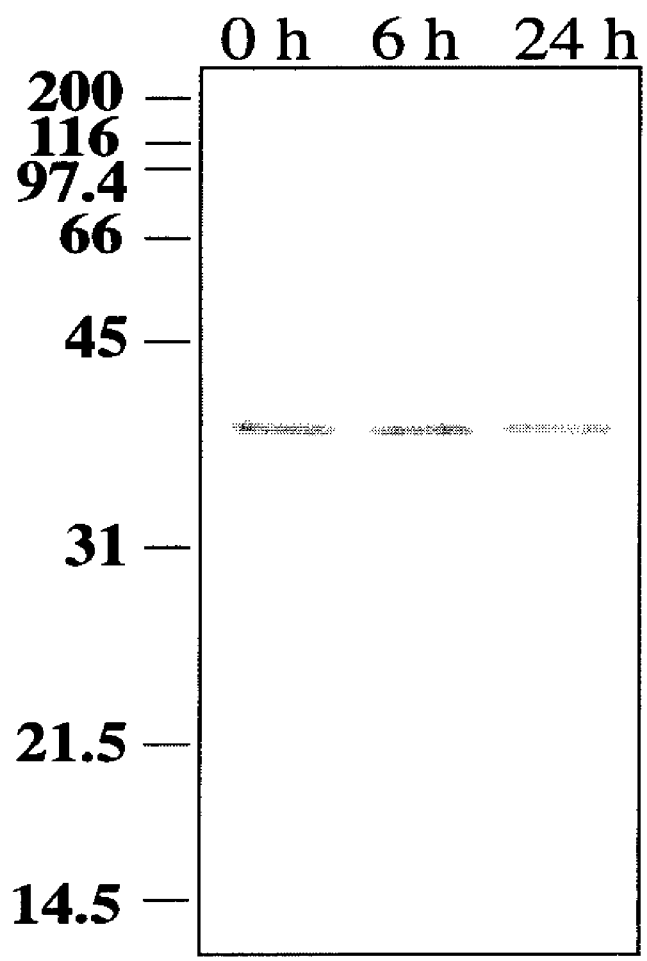

Expression of the sulfate permease in *Synechococcus* sp. strain PCC 7942 (encoded by the CysT gene) is induced under sulfur deprivation conditions (Laudenbach and Grossman (1991) *J. Bacteriol.* 173:2739–2750). The CrcpSulP gene, which is homologous to the CysT gene, also exhibits such induction. Levels of CrcpSulP gene transcripts in *C. reinhardtii* were measured in cells grown under nutrient control (400 µM sulfate) and sulfur deprivation conditions. In the control, levels of the CrcpSulP gene transcripts were low (FIG. 12A, 0 h). Upon a 6 h S-deprivation, transcripts increased substantially and remained at this high level for 24 h and beyond (FIG. 12A, 6 h and 24 h). FIG. 12B shows the corresponding Western blot analysis of total cell protein extracts from cells grown under control or S-deprivation conditions. The level of the SulP protein appeared rather low under normal (control) growth conditions (TAP medium containing 400 micromolar sulfate), which is consistent with the low transcript level for the SulP gene under these conditions. A substantial induction was observed upon 6 h of sulfur deprivation, and maximal induction was attained within 24 h of S-deprivation. Overall, it appeared that during the course of sulfate deprivation, the protein expression pattern follows that of the gene transcript level.

Characterization of CrcpSulP Antisense Transformants

Expression of the CrcpSulP gene is regulated at the transcript level by the amount of sulfate nutrients in the growth medium (FIG. 12A), indicating a possible link between the protein function and sulfate transport. Antisense technology was applied to down-regulate the CrcpSulP expression and test for the functional impact of such interference. An antisense construct of the CrcpSulP gene was made by fusing the rbcS2 promoter to a partial sequence of the CrcpSulP cDNA (in the reverse direction), followed by the rbcS2 3'UTR. In a first series of *C. reinhardtii* antisense transformation experiments, the arginine auxotroph CC425 strain (arg7–8 mt+ cw15 sr-u-2–60; *Chlamydomonas* Genetics Center, Duke University) was utilized in a co-transformation with the anti-CrcpSulP (pAntiSulP) construct and the pJD67 plasmid containing the ARG7 gene (Davies et al. (1996) *EMBO J.* 15:2150–2159). Transformants were selected first on the basis of arginine prototrophy. Out of about 120 arginine prototrophic transformants, co-transformants (containing both pJD67 and pAntiSulP) were selected by genomic DNA PCR, to test for the presence of the inserted anti-CrcpSulP cDNA sequence. From this secondary screening, 31 co-transformants were isolated. Therefore, the co-transformation efficiency was about 26%.

Figure 13:
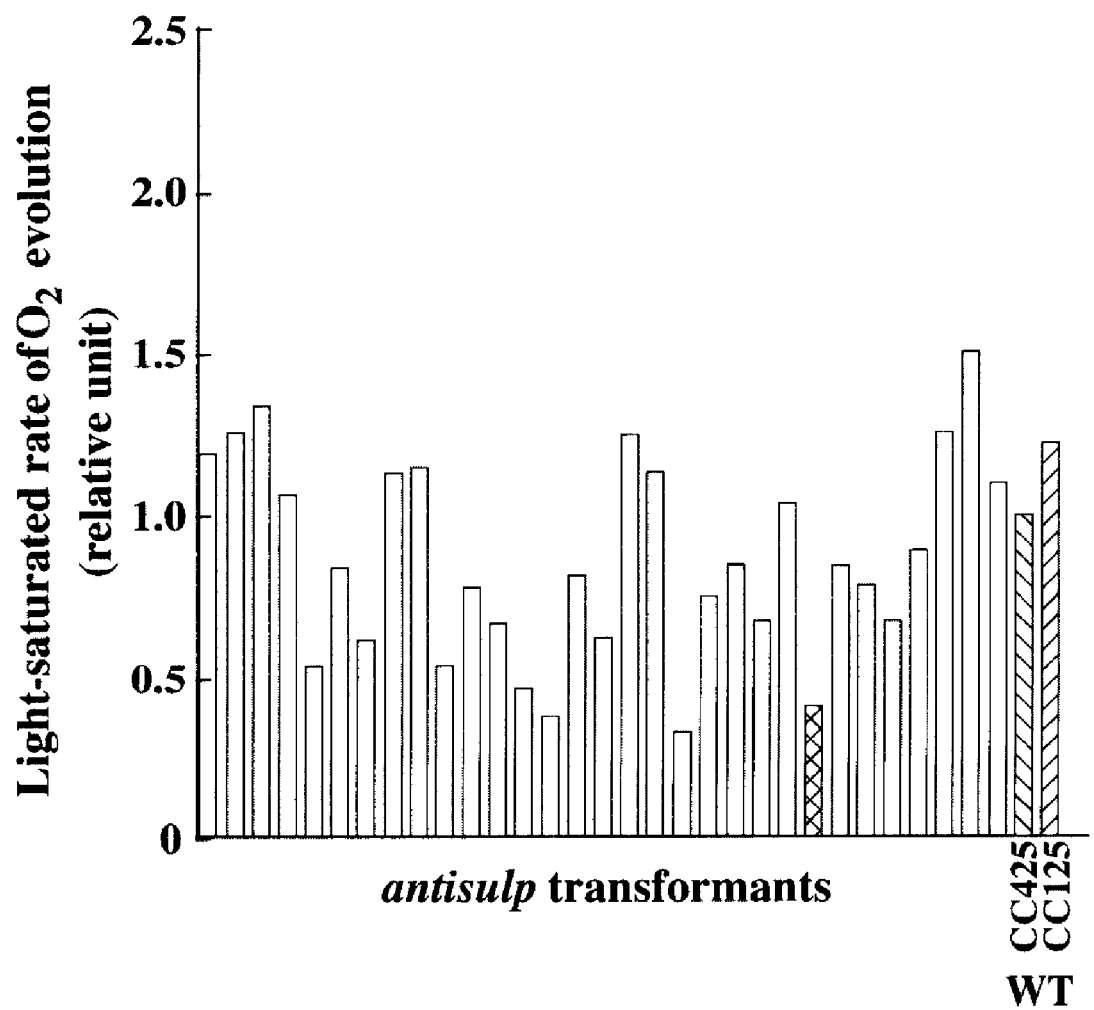
FIG. 13. Light-saturated rates of oxygen evolution in anti-CrcpSulP antisense transformants. Measurements were carried out as described in the Examples. A light intensity of 1,500 micromol of photons $m^{-2}s^{-1}$ was used for all measurements. Values are presented as relative rates of oxygen evolution, normalized to that of the CC425 (=40 micromol $O_2$ per mol Chl per s). Shown are 31 antisense transformants and two 'wild-type' strains. Black column: CC425; Dashed column: CC125. Gray-shaded column corresponds to the antisense transformant asulp29.

Sulfur deprivation causes a decrease in Photosystem-II (PSII) activity and in the light-saturated rate of oxygen evolution (Wykoff et al. (1998) *Plant Physiol.* 104:981–987). Tests were conducted on the anti-CrcpSulP antisense transformants by measuring their light-saturated rate of oxygen evolution. Analysis showed that about 50% of these transformants had rates of $O_2$ evolution that were lower by 20%, or more, compared to that of the CC425 wild-type (FIG. 13). Among these, three transformants named asulp17, asulp22 and asulp29 showed low rates, corresponding to about 42%, 36% and 44% of the wild-type, respectively. It is possible that such phenotype results from the pAntiSulP construct expression in these transformants, which lowers the levels of sulfate permease in the envelope and consequently lower rates of sulfate uptake by the chloroplast. Such scenario would cause lower rates of light-saturated photosynthesis due to the ensuing sulfur limitation in the chloroplast.

Figure 14A:
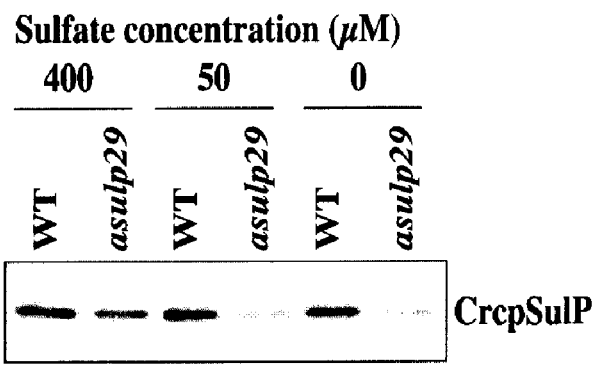
FIGS. 14A, 14B and 14C. Comparative protein profile analysis of wild-type and asulp29.

The antisense transformant asulp29 was selected for further biochemical analysis. First, the level of CrcpSulP protein in asulp29 cells was compared to that of the wild-type. Both cell types were grown in TAP to the early log phase ($1-2 \times 10^6$ cells/mL), then transferred in a medium containing different sulfate concentrations, i.e., 400 µM (control), 50 µM or 0 µM, and incubated for 24 h in the light. Total cell protein extracts were isolated from these samples and subjected to Western blot analysis with specific anti-CrcpSulP antibodies. FIG. 14A shows that, relative to the control (FIG. 14A, 400 µM), the level of this protein in the wild-type showed little or no increase upon incubation of the cells under S-limitation (FIG. 14A, 50 µM), or S-deprivation (FIG. 14A, 0 µM) conditions. Little or no increase in the level of this protein upon S-deprivation is consistent with the results in FIGS. 12A–B. There, an increase in the level of CrcpSulP gene transcripts (FIG. 12A) was not accompanied by a corresponding increase in the level of the protein (FIG. 12B) in this time range.

FIG. 14A also shows that, at 400 µM sulfate in the growth medium, the asulp29 antisense transformant expressed lower levels of the CrcpSulP protein than the wild-type. Moreover, the level of this protein was also lower upon incubation of the asulp29 antisense cells under S-limitation (FIG. 14A, 50 µM), or S-deprivation (FIG. 14A, 0 µM) conditions. These results suggest that expression of the pAntiSulP construct in asulp29 caused a lowering of the corresponding protein level in C. reinhardtii.

Figure 14B:
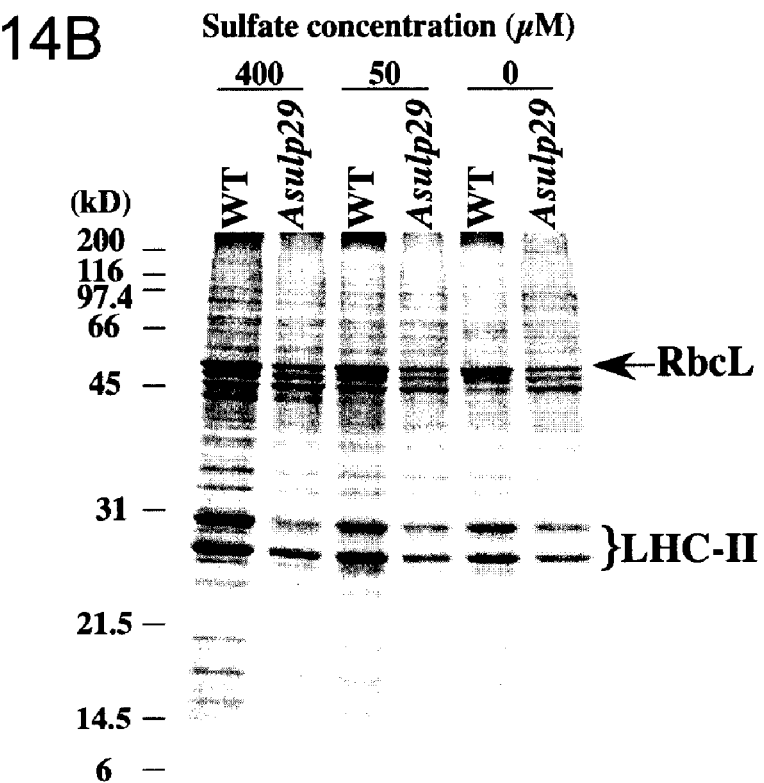
Figure 14C:
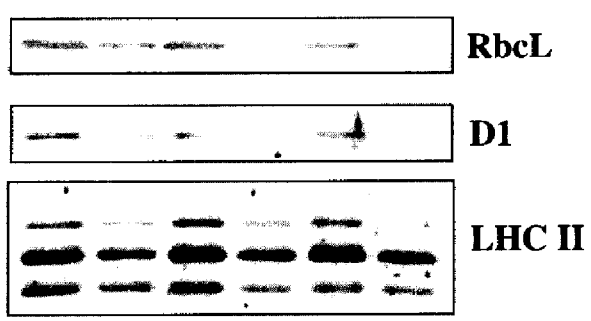

Sulfur deprivation causes changes in the chloroplast protein composition and function in green algae (Zhang et al. (2002) Planta 214:552–561). This includes much lower levels of Rubisco and of the D1 reaction center protein as biosynthesis/stability of these proteins is primarily affected by S-deprivation. FIGS. 14B and 14C show that compared to the control (400 µM), the level of RbcL and D1 in the wild-type declined upon incubation of the cells under S-limitation (50 µM), or S-deprivation (0 µM). The same trend was evident in the asulp29 strain, although the latter exhibited a distinct S-deprivation phenotype even under control conditions (400 µM sulfate).

Levels of the LHC-II (light harvesting complex of PSII) in C. reinhardtii are not affected in the early stages of S-deprivation. Rather, S-deprivation longer than 48–60 h is necessary to induce degradation of the LHC-II (Zhang et al. (2002), supra). This is reflected in the LHC-II Western blot results of FIG. 14C for the wild-type, where S-limitation or S-deprivation for 24 h does not appear to induce a lowering in the level of the LHC-II. The level of the LHC-II proteins was, however, lower in the asulp29 antisense transformant (FIGS. 14B and 14C), consistent with the notion of a prolonged S-limitation in this strain, even in the presence of 400 µM sulfate in the medium. Anti-CrcpSulP antisense transformation of C. reinhardtii caused a lowering in the level of the CrcpSulP protein in the cell. In turn, this caused a substantial lowering in the level of the major chloroplast proteins (Rubisco, D1 and the LHC-II), presumably because the rate of sulfate uptake and of protein biosynthesis is lowered in the chloroplast of the antisense transformant.

Figure 15A:
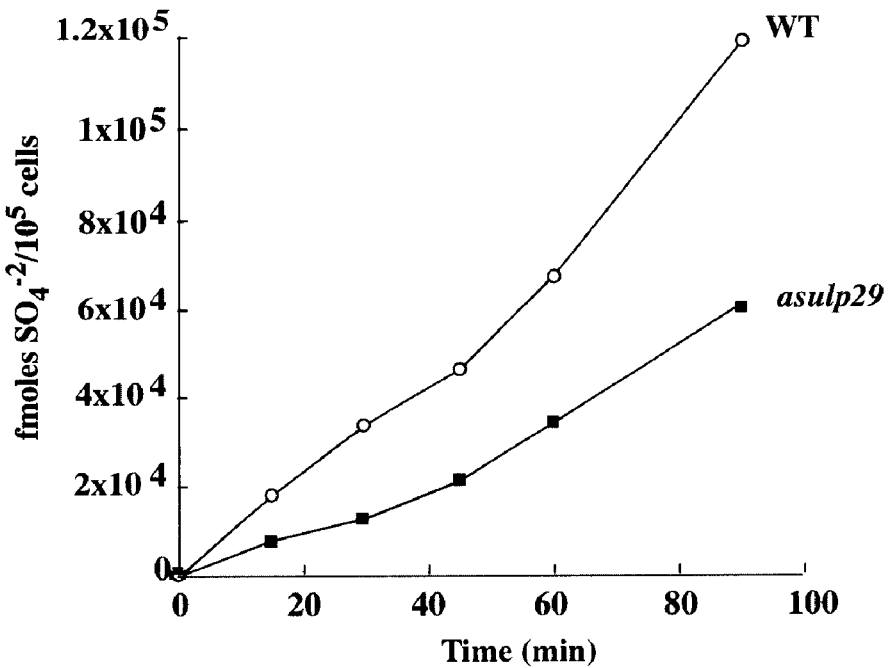
FIGS. 15A and 15B. Analysis of sulfate uptake by wild-type and the asulp29 antisense transformant of *C. reinhardtii*.
Figure 15B:
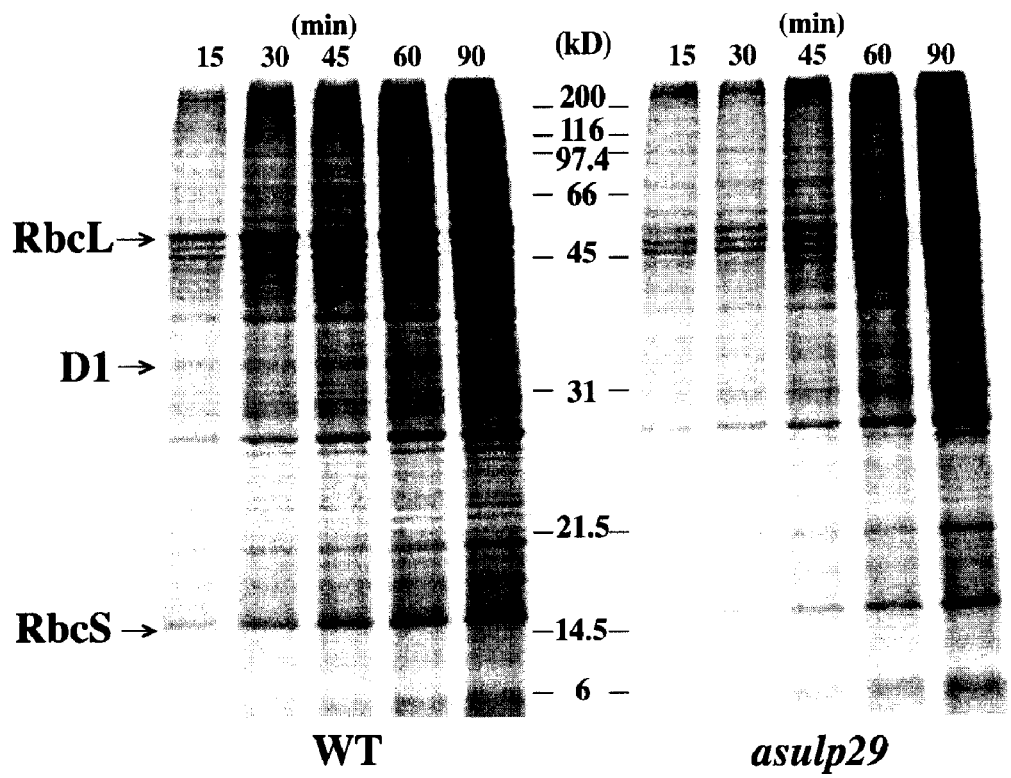

Functionally, a lower level of the CrcpSulP protein in the asulp29 strain is expected to have a ripple effect, lowering the overall sulfate uptake and assimilation capacity of the cell. This was tested in wild-type and asulp29 directly upon $^{35}$S-sulfate uptake measurements under control and S-limitation conditions. FIG. 15A shows the S-uptake by wild-type and asulp29 transformant, measured over a period of 90 min incubation of the cells in the light, in the presence of the $^{35}$S-sulfate. Results showed that under control growth conditions (TAP medium with 400 µM sulfate), the sulfate transport efficiency of asulp29 was only about 40–50% compared to the wild-type strain. The above contention was further investigated by $^{35}$S-pulse labeling of proteins in wild-type and asulp29 transformant (FIG. 15B). Analysis of such $^{35}$S-pulse labeling revealed lower rates, by about 40%, of RbcL, RbcS and D1 protein biosynthesis in the asulp29 transformant relative to the wild-type. Lower $^{35}$S incorporation rates into the Rubisco and D1 in the asulp29 transformant are consistent with a S-limitation in the latter, which would explain the lower steady-state level of these proteins in the antisense strain.

CrcSulP Assays

The co-transformation approach utilized above avoided use of a selectable marker based on antibiotic resistance for the CrcpSulP antisense transformants. Since the CrcpSulP protein might be essential for the survival of C. reinhardtii, lowering the level of this protein through antisense technology could have substantially lowered cell fitness. By avoiding selection of transformants based on antibiotic resistance, it was possible to increase the recovery of antisense mutants.

Antisense transformants were independently generated and isolated based on their antibiotic (zeocin) resistance. In this case, the Ble gene cassette (Lumbreras et al. (1998) Plant J. 14:441–448; and Stevens et al. (1996) Mol. Gen. Genet. 251:23–30) was inserted in the upstream region of the anti-CrcpSulP cDNA. This construct was used for the transformation of the C. reinhardtii cw15 wall-less strain. More than 600 antisense transformants were selected based on zeocin resistance.

A well-known response of C. reinhardtii to S-deprivation is induction of aryl-sulfatase (ARS) activity in the cell, an enzyme that cleaves sulfate groups from aromatic compounds in the cell exterior (de Hostos et al. (1989) Mol. Gen. Genet. 218(2):229–233; Lien and Schreiner (1975) Biochim. Biophys. Acta 384:168–179). CrcpSulP antisense transformants, in which the expression of the CrcpSulP gene is down regulated, are expected to show induction of the ARS activity. ARS activity useful in the present invention is at least 5%. CrcpSulP antisense transformants were screened on the basis of their ARS activity. Accordingly, the wild-type and a group of more than 600 antisense transformants were incubated in growth media containing different sulfate concentrations. In calibration experiments, it was found that the wild-type (cw15) already exhibited signs of S-limitation at 50 µM sulfate concentration, as evidenced from the induction of its ARS activity. A 150 µM sulfate concentration in the medium proved to be well above the threshold for the induction of the ARS activity in the wild-type. Thus, screening for CrcpSulP antisense transformants by the ARS activity was implemented upon cell suspension in TAP containing 150 μM sulfate. The results were compared with the response of the strains in a replica plate, where cells were suspended at 400 μM sulfate.

Figure 16:
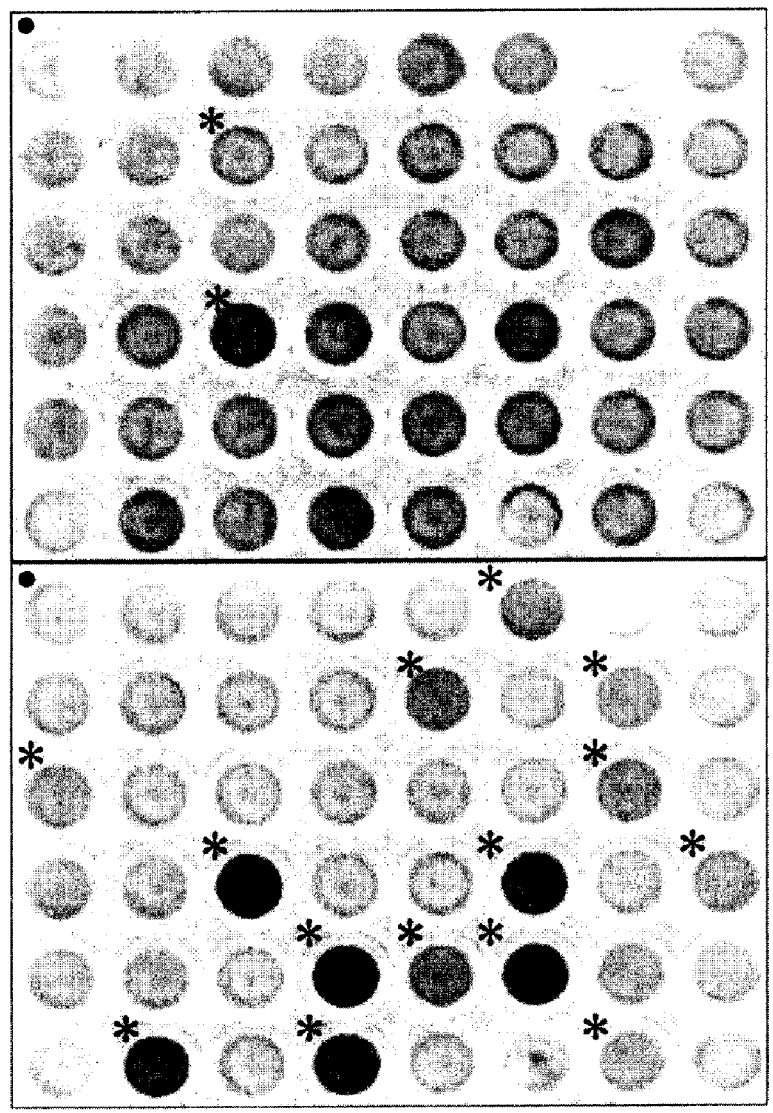
FIG. 16. Aryl-sulfatase (ARS) activity analysis of wild type and antisense transformants of *C. reinhardtii*. Microtiter plates with the algae were placed under continuous illumination for 24 h prior to the detection of the ARS activity. For the latter, 10 μl of 10 mM 5-bromo-4-chloro-3-indolyl sulfate (XSO$_4$, Sigma) in 10 mM Tris-HCl pH 7.5, was added to the cell suspension. The color of the mixture was allowed to develop over a 3–4 h period, followed by scanning of the microtiter plate for the recording of the resulting images. (Upper) Wild type and 47 antisense transformants were tested for their ARS activity induction when suspended in control TAP medium (400 μM sulfate). (Lower) Replica plate of the above with strains suspended in a TAP medium containing 150 μM sulfate. The wild type control strain is shown in the upper left corner of the liquid culture multi-well plates, marked by ".". Strains that showed ARS activity, as judged by the appearance of blue color in the 96-well plates, are indicated by "*".
Figure 17:
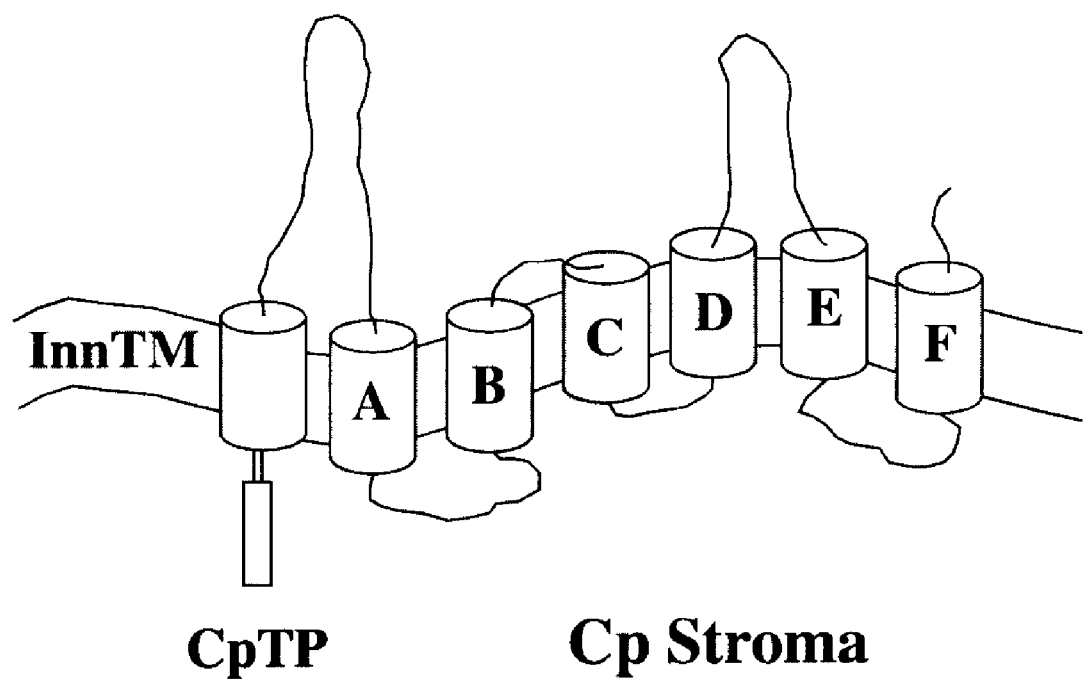
FIG. 17. Working hypothesis folding-model of the CrcpSulP protein. CpTP refers to the chloroplast transit peptide prior to cleavage by a stroma-localized peptidase. InnTM represents the first N-terminal transmembrane domain of the CrcpSulP protein, which is specific to *C. reinhardtii*. A through F represents the 6 conserved transmembrane domains of green alga chloroplast sulfate permeases. Note the two extended hydrophilic loops, occurring between transmembrane helices InnTM-A and D–E, facing toward the exterior of the chloroplast.
Figure 18A:
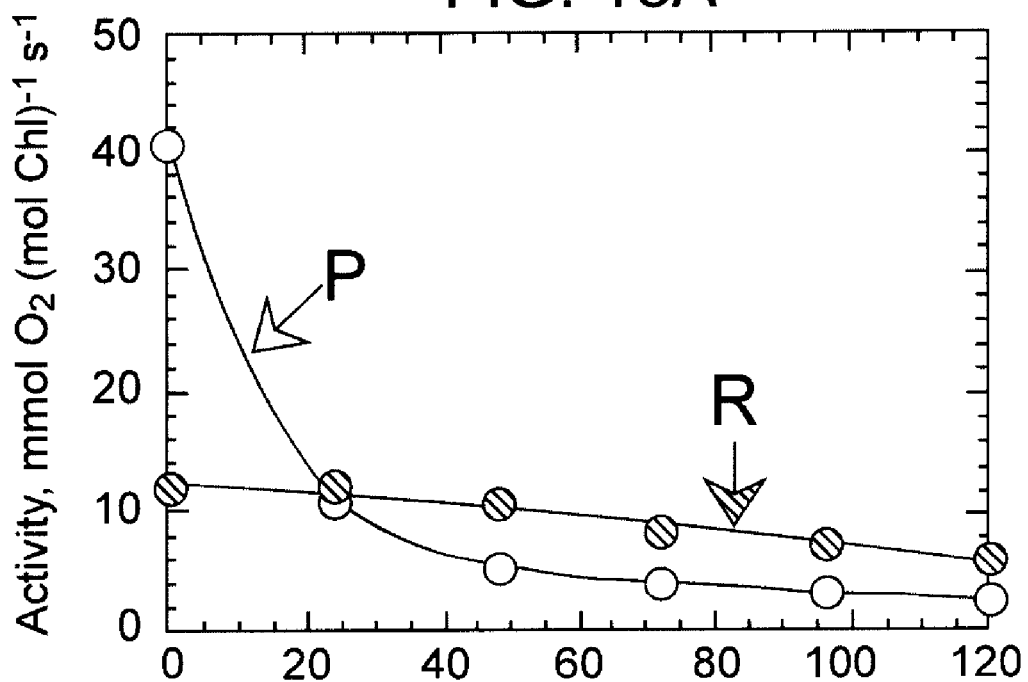
FIGS. 18A and 18B. Photosynthesis, respiration and hydrogen production as a function of sulfur-deprivation in *C. reinhardtii*.
Figure 18B:
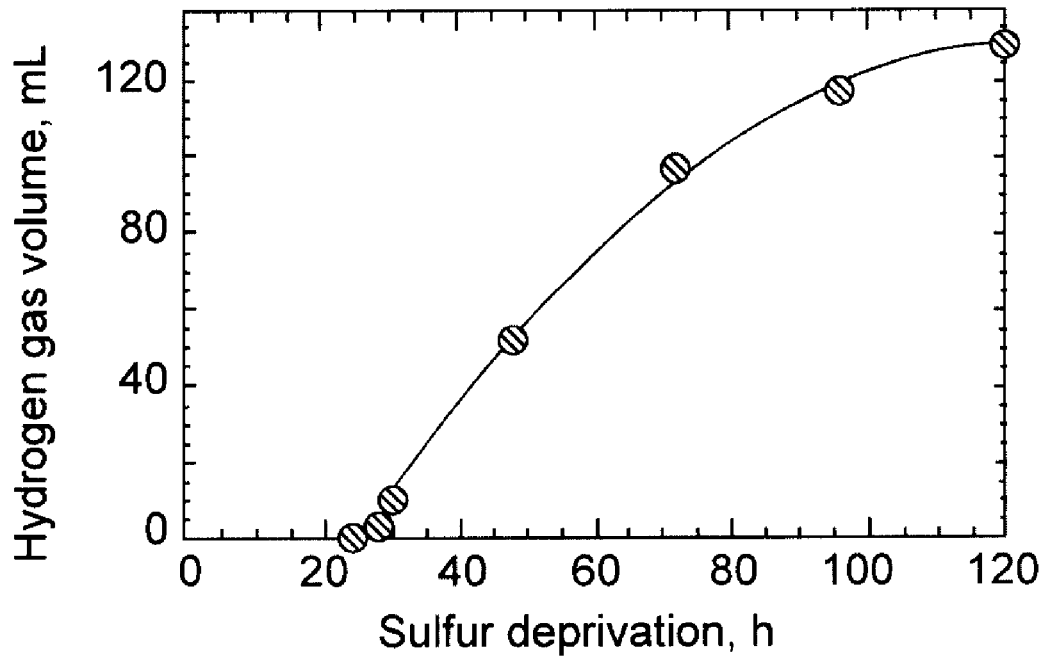
Figure 19:
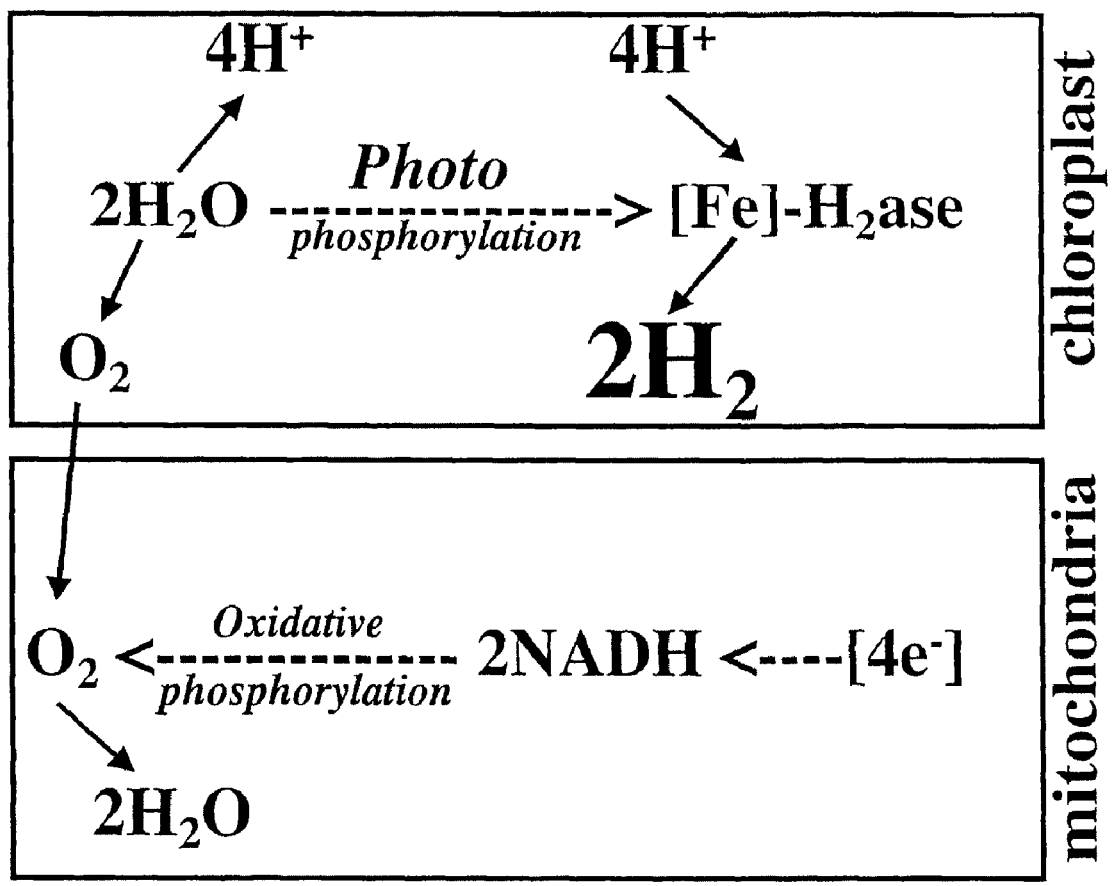
FIG. 19. Coordinated photosynthetic and respiratory electron transport and coupled phosphorylation during hydrogen production in green algae. Photosynthetic electron transport delivers electrons upon photo-oxidation of water to the hydrogenase, leading to photophosphorylation and hydrogen production. The oxygen generated by this process serves to drive the coordinate oxidative phosphorylation during mitochondrial respiration. Electrons for the latter ([4e]) are derived upon endogenous substrate catabolism, which yields reductant and CO$_2$. Release of molecular hydrogen by the chloroplast enables the sustained operation of this coordinated photosynthesis-respiration function in green algae and permits the continuous generation of ATP by the two bioenergetic organelles in the cell.

An example of such screening in replica plates, is shown in FIG. 16, where tests of ARS activity were conducted in the wild-type and 47 antisense transformants. FIG. 16 (upper) shows these strains suspended in control TAP (400 μM sulfate). In this plate, two transformants showed detectable induction of the ARS activity (transformant numbers 11 and 27). FIG. 16 (lower) shows the same strains, suspended under S-limitation conditions (TAP w/150 μM sulfate). In this plate, 14 anti-SulP antisense transformants, but not the wild-type, showed strong induction of the ARS activity. FIG. 16 (lower) shows that ARS activity varied considerably among the antisense transformants. This variable phenotype is consistent with the nature of antisense transformation. It is believed that the mutant(s) with the strongest ARS activity may have the most severe inhibition in the expression of the CrcpSulP gene. Nevertheless, these results prove the applicability of antisense technology in *Chlamydomonas reinhardtii* and the use of the ARS screening method for the isolation of antisense mutants with differential sulfate uptake capacities.

Green Algae

The photosynthetic metabolism of hydrogen in green algae was discovered by Hans Gaffron, who observed that under anaerobic conditions, green algae can either use hydrogen as an electron donor in the $CO_2$ fixation process in the dark, or evolve hydrogen in the light. Gaffron's original observations were extended to many green algae, including *Scenedesmus obliquus* (Gaffron and Rubin (1942) *J. Gen. Physiol.* 26:219–240; Bishop et al. (1977) in: Biological Solar Energy Conversion, Misui et al., eds., Academic Press, New York, pp. 3–22; and Schnackenberg et al. (1993) *FEBS Lett.* 327:21–24), *Chlorella fusca* (Kessler (1973) *Arch. Microbiol.* 93:91–100), and *Chlamydomonas reinhardtii* (McBride et al. (1977) in: Biological Solar Energy Conversion, Misui et al., eds., Academic Press, New York, pp. 77–86; Maione and Gibbs (1986) *Plant Physiol.* 80:364–368; Greenbaum et al. (1988) *Biophys. J.* 54:365–368).

Historically, hydrogen evolution activity in green algae was induced upon a prior anaerobic incubation of the cells in the dark (Roessler and Lien (1984) *Plant Physiol.* 76:1086–1089). A hydrogenase enzyme (Vignais et al. (2001) *FEMS Microbiol. Rev.* 25:455–501) was expressed under such incubation and catalyzed, with high specific activity, a light-mediated hydrogen evolution. The monomeric form of the enzyme, belongs to the class of [Fe]-hydrogenases (Voordouw et al. (1989) *J. Bacteriol.* 171: 3881–3889; Adams, M. (1990), supra, Meyer and Gagnon (1991), supra, Happe et al. (1994), supra), is encoded in the nucleus of the unicellular green algae. However, the mature protein is localized and functions in the chloroplast stroma. Light absorption by the photosynthetic apparatus is essential for the generation of molecular hydrogen since light-energy facilitates the oxidation of water molecules, the release of electrons and protons, and the endergonic transport of these electrons to ferredoxin. The photosynthetic ferredoxin (PetF) serves as the physiological electron donor to the [Fe]-hydrogenase and, therefore, links the soluble [Fe]-hydrogenase to the electron transport chain in the green alga chloroplast (Florin et al. (2001), supra). Absence of $CO_2$ enhanced the light-driven hydrogen production, suggesting a competition for electrons between the $CO_2$ fixation and the hydrogen production processes (Cinco et al. (1993) *Photosynth. Res.* 38:27–33).

Under oxygenic photosynthesis conditions, and following a dark anaerobic induction, the activity of the hydrogenase is only transient in nature. It lasts from several seconds to a few minutes. This is because photosynthetic $O_2$ is a powerful inhibitor of the [Fe]-hydrogenase (Ghirardi et al. (2000), supra) and a positive suppressor of hydrogenase gene expression (Florin et al. (2001), supra; and Happe and Kaminski (2002), supra). The physiological significance and role of the [Fe]-hydrogenase in green algae, which normally grow under aerobic photosynthetic conditions, has long been a mystery. Given the $O_2$ sensitivity of the [Fe]-hydrogenase and the prevailing oxidative environmental conditions on earth, questions have been asked as to whether the hydrogenase is anything more than a relic of the evolutionary past of the chloroplast in green algae. And whether this enzyme and the process of photosynthesis can ever be utilized to generate hydrogen for commercial purposes (Zhang et al. (2002), supra). Nevertheless, the ability of green algae to photosynthetically generate molecular hydrogen has captivated the fascination and interest of the scientific community because of the fundamental and practical importance of the process (Melis and Happe (2001), supra). The following lists the properties and promise of photosynthetic hydrogen production, and the problems that are encountered in the process:

Photosynthesis in green algae can operate with a photon conversion efficiency of greater than 80% (Ley and Mauzerall (1982) *Biochim. Biophys. Acta* 680:95–106).

Microalgae can produce hydrogen photosynthetically, with a photon conversion efficiency of greater than 80% (Greenbaum, E. (1988), supra).

Molecular oxygen is a powerful and effective switch by which the hydrogen production activity is turned off.

The incompatibility in the simultaneous $O_2$ and hydrogen photo-production was the limiting factor in 60 years of related research.

The Electron Transport Chain of Photosynthesis

The process of photosynthetic hydrogen production with electrons derived from water (also referred to as "biophotolysis" (Miura (1995), supra, and Benemann (1996), supra) entails water oxidation and a light-dependent transfer of electrons to the [Fe]-hydrogenase, leading to the synthesis of molecular hydrogen. Electrons are generated upon the photochemical oxidation of water by PSII. These are transferred through the thylakoid membrane electron-transport chain and, via PSI and ferredoxin, are donated to the HC cluster of [Fe]-hydrogenase (Florin et al. (2001), supra). Protons ($H^+$) are the terminal acceptors of these photosynthetically generated electrons in the chloroplast. The process does not involve $CO_2$ fixation or energy storage into cellular metabolites. This process results in the simultaneous production of oxygen and hydrogen with an $H_2:O_2=2:1$ ratio (Spruit, C. P. (1958), supra; Greenbaum et al. (1983), supra). This mechanism makes it possible to generate hydrogen continuously and efficiently through the solar conversion ability of the photosynthetic apparatus.

In the absence of provision for the active removal of oxygen, this mechanism can operate only transiently, as molecular oxygen is a powerful inhibitor of the enzymatic reaction and a positive suppressor of [Fe]-hydrogenase gene expression. This direct mechanism has limitations as a tool of further research and for practical application, mainly due to the great sensitivity of the [Fe]-hydrogenase to $O_2$, which is evolved upon illumination by the water oxidizing reactions of PSII (Ghirardi et al. (2000), supra). An additional problem, assuming that the mutual incompatibility of $O_2$ and $H_2$ co-production is overcome, entails the separation of the two gases, a costly and technologically challenging feat.

However, $O_2$ and $H_2$ co-production can be prolonged under conditions designed to actively remove $O_2$ from the reaction mixture. For example, Greenbaum and co-workers (Greenbaum, E. (1982) *Science* 196:879–880; Greenbaum, E. (1988), supra; Greenbaum et al. (1983), supra) have sustained a photosynthetic water-to-hydrogen process continuously for days upon sparging the reaction mixture with helium, thus removing from the vicinity of the cells the photosynthetic gas products (oxygen and hydrogen). The present invention provides a way to mutate or downregulate the expression of the sulfate permease (CrcpSulP) with the objective of altering or removing the oxygen presence within the cell (Ghirardi et al. (2000), supra), thereby permitting a light-driven oxygen and hydrogen co-production in the green algae.

Aside from the above-described PSII-dependent hydrogen photoproduction, which involves water as the source of electrons and, in the absence of $CO_2$, produces 2:1 stoichiometric amounts of $H_2$ and $O_2$, an alternative source of electrons has been described in the literature. Catabolism of endogenous substrate and the attendant oxidative carbon metabolism in green algae may generate electrons for the photosynthetic apparatus (Gfeller and Gibbs (1984) *Plant Physiol.* 75:212–218). Electrons from such endogenous substrate catabolism feed into the plastoquinone pool between the two photosystems (Stuart and Gaffron (1972) *Planta* (Berlin) 106:101–112; Godde and Trebst (1980) *Arch. Microbiol.* 127:245–252). An NAD(P)H-plastoquinone oxidoreductase that feeds electrons into the plastoquinone pool has recently been identified in many vascular plant chloroplasts (Shinozaki et al. (1986) *EMBO J.* 5:2043–2049; Neyland and Urbatsch (1996) *Planta* 200:273–277). However, this work has been generally limited to green alga *Nephroselmis olivacea* (Turmel et al. (1999) *Proc. Natl. Acad. Sci. USA* 96:10248–10253). Light absorption by PSI and the ensuing electron transport elevates the redox potential of these electrons to the redox equivalent of ferredoxin and the [Fe]-hydrogenase. In this case, protons ($H^+$) act as the terminal electron acceptor (Gfeller and Gibbs (1984), supra; Bennoun, P. (2001) *Biochim. Biophys. Acta* 1506: 133–142), thus permitting the generation of molecular hydrogen (Gibbs et al. (1986) *Plant Physiol.* 82:160–166). In the presence of DCMU, a PSII inhibitor, this process generates 2:1 stoichiometric amounts of hydrogen and $CO_2$ (Bamberger et al. (1982) *Plant Physiol.* 69:1268–1273). Thus, following a dark-anaerobic-incubation of the culture (induction of the [Fe]-hydrogenase), initially substantial rates hydrogen production can be detected upon illumination of the algae in the presence of DCMU (Happe and Naber (1993) *Eur. J. Biochem.* 214:475–481; and Florin et al. (2001) *J. Biol. Chem.* 276:6125–6132).

The regulation of endogenous substrate catabolism and the attendant supply of electrons to the electron transport chain of photosynthesis form an aspect of the invention. Whereas rates of water oxidation by the photosynthetic apparatus can be measured continuously and precisely, measurements of electron transport supported by endogenous substrate catabolism and NAD(P)H-plastoquinone oxidoreductase activity are more difficult to make. Hydrogen photoproduction with anaerobically-incubated and DCMU-poisoned chloroplasts (Florin et al. (2001), supra) suggests that, initially, substantial rates of hydrogen production can be detected. However, this process could not be sustained for significant periods of time (Zhang et al. (2002), supra). The present invention indicates that such is due to limitation(s) in the capacity of the electron transport reactions associated with the NAD(P)H-plastoquinone oxidoreductase activity. The present invention provides endogenous starch, protein and lipid catabolism to feed electrons into the plastoquinone pool, thus contributing to hydrogen photoproduction.

Effect of Sulfur Deprivation

Lack of sulfur nutrients from the growth medium of *Chlamydomonas reinhardtii* cause a specific but reversible decline in the rate of oxygenic photosynthesis (Wykoff et al. (1998), supra) but does not affect the rate of mitochondrial respiration (Melis et al. (2000), supra). In sealed cultures, imbalance in the photosynthesis-respiration relationship by S-deprivation resulted in net consumption of oxygen by the cells causing anaerobiosis in the growth medium. It was shown that expression of the [Fe]-hydrogenase is elicited in the light under these conditions, automatically leading to hydrogen production by the algae (Melis et al. (2000), supra; and Ghirardi et al. (2000), supra). Under S-deprivation, it was possible to photoproduce and to accumulate bulk amounts of hydrogen gas, emanating as bubbles from the green alga culture, a sustainable process that could be employed continuously for a few days. Hydrogen production can be obtained by circumventing the sensitivity of the [Fe]-hydrogenase to $O_2$ through a temporal separation of the reactions of $O_2$ and hydrogen photoproduction, i.e., by a so-called "two-stage photosynthesis and hydrogen production" process (Melis et al. (2000), supra). Application of this novel two-stage protocol revealed the occurrence of hitherto unknown metabolic, regulatory and electron-transport pathways in the green alga *C. reinhardtii* (Zhang et al. (2002), supra).

This method serves as a tool for the elucidation of the green alga photosynthesis/respiration relationship and as the foundation of a tri-organism integrated hydrogen production system. The method also provides for the generation of hydrogen gas for the agriculture, chemical and fuel industries. The temporal sequence of events in this two-stage photosynthesis and hydrogen production process is as follows:

a) Green algae are grown photosynthetically in the light (normal photosynthesis) until they reach a density of 3–6 million cells per mL in the culture. Under these growth conditions, the photosynthesis/respiration ratio of the algae (P/R ratio) is about 4:1, resulting in oxygen release and accumulation in the medium. Under such conditions, there can be no hydrogen production.

b) Sulfur deprivation is imposed upon the cells in the growth medium, either by carefully limiting sulfur supply so that it is consumed entirely, or by permitting cells to concentrate in the growth chamber prior to medium replacement with one that lacks sulfur nutrients. Cells respond to this S-deprivation by fundamentally altering photosynthesis and cellular metabolism in order to survive (Davies et al. (1996) *EMBO J.* 15:2150–2159; and Hell, R. (1997) *Planta* 202:138–148). Noteworthy in this respect is the 10-fold increase in cellular starch content during the first 24 h of S-deprivation (Cao et al. (2001) *J. Appl. Phycol.* 13:25–34; and Zhang et al. (2002), supra).

c) S-deprivation exerts a distinctly different effect on the cellular activities of photosynthesis and respiration (FIG. 1A). The capacity of oxygenic photosynthesis declines quasi-exponentially with a half time of 15–20 h to a value less than 10% of its original rate (Wykoff et al. (1998), supra). However, the capacity for cellular respiration remains fairly constant over the S-deprivation period (Melis et al. (2000), supra). In consequence, the absolute activity of photosynthesis crosses below the level of respiration after about 24 h of S-deprivation, resulting in a P/R<1 ratio (FIG. 1A). Following this cross-point between photosynthesis and respiration, sealed cultures of S-deprived *C. reinhardtii* quickly consume all dissolved oxygen and become anaerobic (Ghirardi et al. (2000), supra), even though they are maintained under continuous illumination.

d) Under S-deprivation conditions, sealed (anaerobic) cultures of *C. reinhardtii* induce the [Fe]-hydrogenase and produce hydrogen gas in the light but not in the dark (FIG. 1B). The rate of photosynthetic hydrogen production was about 2.5 mL per liter culture per hour and was sustained in the 24–96 h period. The rate gradually declined thereafter.

e) In the course of such hydrogen gas production, cells consumed significant amounts of internal starch and protein (Zhang et al. (2002), supra). Such catabolic reactions apparently sustain, directly or indirectly, the hydrogen production process.

The absence of sulfur nutrients from the growth medium of algae acts as a metabolic switch, one that selectively and reversibly lowers the P/R ratio. Thus, in the presence of S (P/R=4:1), green algae do normal photosynthesis (water oxidation, $O_2$ evolution and biomass accumulation). In the absence of S and absence of $O_2$ (P/R<1), photosynthesis in *C. reinhardtii* slips into the hydrogen production mode. Reversible application of the switch (presence/absence of S) permits the algae to alternate between $O_2$ production and hydrogen production (Cycling of the Stages, FIG. 2) thus bypassing the incompatibility and mutually exclusive nature of the $O_2$ and hydrogen producing reactions. Interplay between oxygenic photosynthesis, mitochondrial respiration, catabolism of endogenous substrate, and electron transport via the hydrogenase pathway is essential for this light-mediated hydrogen production process. The release of hydrogen gas serves to sustain baseline levels of chloroplast and mitochondrial electron transport activity (FIG. 3) for the generation of ATP (Arnon et al. (1961) *Science* 134:1425), which is needed for the survival of the organism under the protracted sulfur-deprivation stress conditions.

The present invention provides information on the 4-way interplay between the processes of oxygenic photosynthesis, mitochondrial respiration, catabolism of endogenous substrate, and electron transport via the [Fe]-hydrogenase pathway leading to hydrogen production. The present invention provides sustainable hydrogen production that bypasses the sensitivity of the [Fe]-hydrogenase to $O_2$. The invention provides a tool in the elucidation of the above regulation and integration of cellular metabolism, one aspect of which is hydrogen photoproduction. The invention uses the exploitation of green algae for the production of a clean and renewable fuel. However, the actual rate of hydrogen gas accumulation was at best 15–20% of the photosynthetic capacity of the cells, when the latter is based on the capacity for $O_2$ evolution under physiological conditions (Melis et al. (2000), supra). The relatively slow rate of hydrogen production suggests a rate-limiting step in the overall process.

Photosynthetic Bacteria Co-Cultured With Algae

Anoxygenic photosynthetic bacteria do not have the ability to oxidize water and to extract protons and electrons. However, they utilize the infrared (700–1,000 nm) region of the spectrum to drive photosynthetic electron transport for the generation of chemical energy in the form of ATP. The latter is critical for the function of the nitrogenase/hydrogenase enzyme and in hydrogen production by these organisms (equation 1). Thus, utilization of the infrared region of the spectrum for photosynthesis in these organisms offers another avenue of hydrogen production. Such organisms permit additional exploitation of the energy of the sun that substantially double the solar irradiance converted. The absorbance spectrum of photosynthetic bacteria, such as *Rhodobacter sphaeroides* RV, complements that of green algae (400–700 nm), such as *Chlamydomonas reinhardtii*, raising the prospect of co-cultivation of the two organisms for substantially enhanced rates and superior yields of photobiological hydrogen production. The recent isolation of green algae with a substantially lowered photosynthesis/respiration ratio (strain sulP1 having a P/R=1.1:1) permits unrestricted co-cultivation of a green alga with *Rhodobacter sphaeroides* RV. The hybrid hydrogen production system of the invention makes use of the best features in each of these organisms for superior rates and yields of hydrogen production. The present invention provides such a hybrid system for integrated hydrogen production.

The art of hydrogen production by photosynthetic bacteria is well established in the literature (Miyaki et al. (2001) in: BioHydrogen II. An Approach to Environmentally Acceptable Technology, Pergamon Press, New York). The enzyme responsible for hydrogen production in these organisms is the nitrogenase/hydrogenase (Fedorov et al. (1999) *Microbiol.* 68:379–386; Elsen et al. (2000) *J. Bacteriol.* 182:2831–2837). It is a highly oxygen-sensitive enzyme, as is the [Fe]-hydrogenase of the green algae, and requires anaerobiosis for its function. Previously, hydrogen production research with such photosynthetic bacteria was performed in pure cultures, which were provided with small organic acids as the initial carbon source. Rates of hydrogen production in these systems were high, typically 40–60 mL hydrogen per L culture per h. However, the process could not be sustained beyond 60 h as the small organic acid substrate was totally consumed by these microorganisms. The hybrid green alga/photosynthetic bacterium culture makes it possible to sustain this co-dependent process as green algae exude small organic acids in the course of hydrogen production (Winkler et al. (2002) *Intl. J. Hydrogen Energy* 27:1431–1439), which can be used by the photosynthetic bacteria, thus providing better continuity and enhanced yields.

Non-photosynthetic anaerobic bacteria, like members of the genus *Clostridium*, produce hydrogen from sugars and other organic molecules at rates ranging between 25–55 mL hydrogen per L culture per h. The basic biochemistry that underlines this process is shown in equation (2) below:

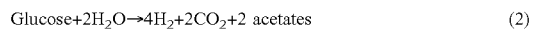

$$\text{Glucose} + 2H_2O \rightarrow 4H_2 + 2CO_2 + 2 \text{ acetates} \qquad (2)$$

Depending on the bacterial species and conditions used, other small organic acid molecules, such as malate, lactate, propionate and/or butyrate may result. The further conversion of these small organic acids to hydrogen is an energetically unfavorable reaction and will not be supported by the non-photosynthetic anaerobic bacteria. Rather, these organic acids accumulate in the growth medium, causing inhibition in the growth and hydrogen production of the microorganism. In consequence, the duration of the hydrogen production reaction (equation 2) could be relatively short and yields can be limited because of the accumulated small organic acids, which are the end product of the anaerobic fermentation.

Additional genes, more completely defining the sulfate transporter complex in the chloroplast of *Chlamydomonas reinhardtii* and pertaining to green alga hydrogen production are disclosed in FIGS. 21, 22 and 23. Novel genes Sulp2, Sabc and Sbp encode proteins that are components of the chloroplast sulfate transport system in this green alga. These sequences as well as the above disclosed CrcpSulP gene, obviate the requirement of sulfur-deprivation in photosynthetic hydrogen production.

These sequences can be operatively inserted into an organism in order to alleviate cumbersome nutrient removal procedures. Moreover, each of these sequences individually, or all of them collectively, permit a continuous production of hydrogen as they alleviate the need of the cells to go back to normal photosynthesis in order to recover lost metabolites such as starch and protein.

FIGS. 21, 22 and 23 show the nuclear-encoded *Chlamydomonas reinhardtii* (green alga) genes, hereby termed Sulp2, Sabc and Sbp. Complete cDNA and protein sequences for these genes are also provided in SEQ ID NOS:4, 5 and 6 and the proteins encoded thereby are shown in FIGS. 24, 25 and 26 and SEQ ID NOS:7, 8 and 9. The proteins encoded by Sulp2 and Sabc, along with the previously disclosed CrcpSulP gene, form a sulfate transport complex that regulates sulfate transport into the chloroplast.

Sbp encodes a sulfate binding protein that functions to bind and carry sulfate to the chloroplast sulfate transport system, a process that is necessary for the transport of sulfate into the chloroplast. The expression of these genes can be manipulated by genetic transformation of the algae (antisense or RNAi technology) to attenuate the uptake of sulfate by the chloroplast. Such transformants of green algae produce hydrogen in the light without a prior need to remove sulfur nutrients from the growth medium.

The application of antisense or RNAi technology to these novel genes renders obsolete the sulfur-deprivation method in green alga hydrogen production, as it obviates the need to physically remove sulfur nutrients from the growth medium of the algae in order to induce the hydrogen production process. Moreover, application of such gene technology with the Sulp2, Sabc and Sbp genes permits a continuous hydrogen production with the green algae as opposed to the discontinuous process currently achieved upon physical removal of sulfate from the growth medium.

The nucleotide sequence of the cDNA of Sulp2, Sabc and Sbp genes is shown in FIGS. 21, 22 and 23, respectively. The deduced amino acid sequence corresponding to each protein is shown respectively in FIGS. 24, 25 and 26.

Sequence analysis of these novel genes showed unobvious features, which are unique to the green alga *Chlamydomonas reinhardtii*. However, their deduced amino acid sequence showed similarity with corresponding proteins in *Synechococcus* sp PCC 7942 for which the function in sulfate uptake has been shown.

This amino acid sequence similarity suggests that the Sulp2, Sabc and Sbp genes play a role in sulfate uptake by the chloroplast in *Chlamydomonas reinhardtii*. FIG. 6 schematically illustrates the process of the sulfate nutrient uptake and transport through the cytosol and chloroplast-envelope of the *Chlamydomonas reinhardtii*. Sulfur nutrients are taken-up by the cell as sulfate anions through a plasma membrane sulfate transporter. Once inside the cytosol, sulfate anions need be transported into the chloroplast, where the sulfate assimilation exclusively takes place. This is the function of the Chloroplast Sulfate Transport System (FIG. 6).

Figure 27:
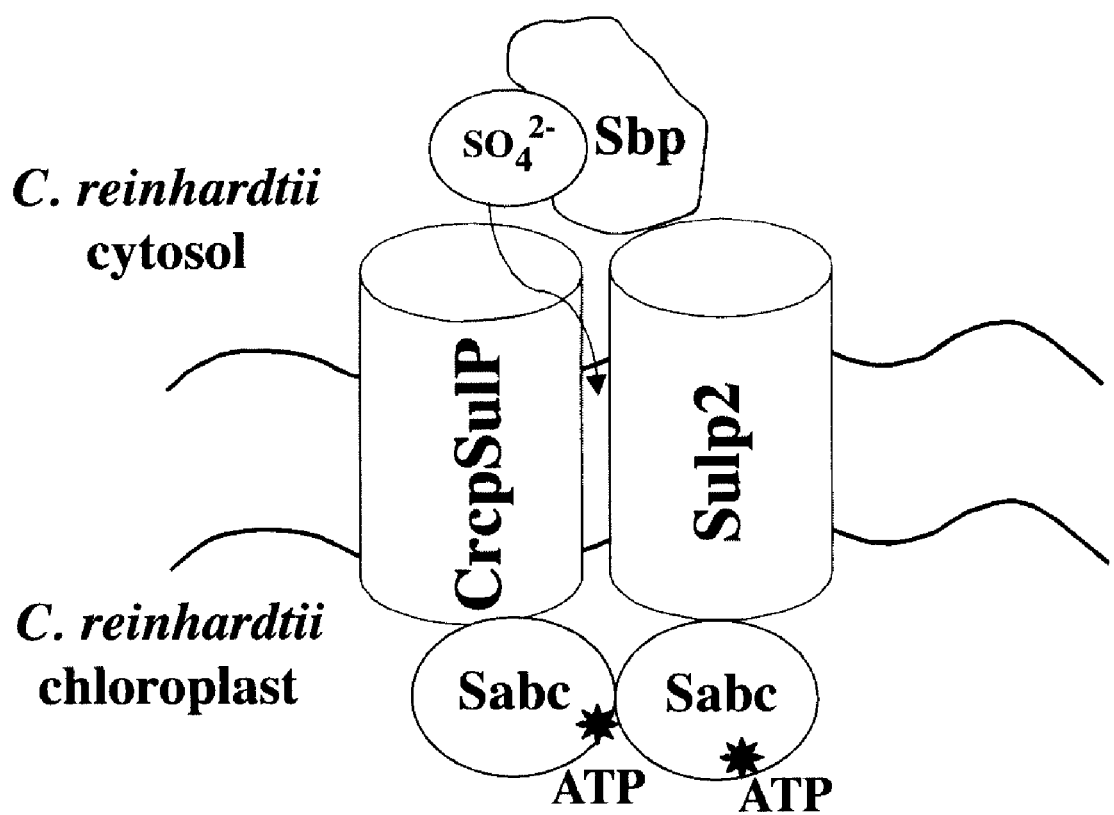

Inside the chloroplast, sulfate anions are assimilated into the essential amino acid cysteine. Cysteine is required for protein biosynthesis, which in turn enables normal oxygenic photosynthesis, carbon accumulation and biomass increase. Based on the sequence analysis of CrcpSulP, Sulp2, Sabc and Sbp genes, FIG. 27 schematically shows the organization and function of the Chloroplast Sulfate Transport System, of the present invention and, as a working model, the pathway by which sulfate anions are transported through the Chloroplast Sulfate Transport System into the chloroplast. The pathway postulates that sulfate anions from the cytosol are carried by the sulfate binding protein, Sbp, to the transmembrane component of the Chloroplast Sulfate Transport System in order for them to be transported through the envelope membrane into the chloroplast. The envelope component of the chloroplast sulfate transporter is composed of two transmembrane proteins: CrcpSulP and Sulp2, which form a dimeric complex integral to the chloroplast envelope and capable of forming a channel suitable for the transport of sulfates; and an ATP-binding protein, Sabc, localized on the chloroplast side of the envelope. Binding of ATP to the Sabc protein causes a conformational change in the two transmembrane CrcpSulP-Sulp2 proteins, which opens the channel between them allowing the sulfate anions to pass through.

The function of the genes (Sulp2, Sabc and Sbp) shown in FIGS. 21, 22 and 23 is to regulate sulfate uptake by the chloroplast in this green alga. Sulfate availability to the chloroplast regulates the rate of oxygenic photosynthesis and leads to hydrogen production. Application of antisense (or RNAi) technology in *C. reinhardtii* to down-regulate the expression of either Sulp2, Sabc or Sbp, or any combination of these genes leads to the generation of transformants with a capacity of photosynthesis that is less than that of cellular respiration.

Sealed cultures of such transformants become anaerobic in the light, as the capacity for respiration is equal to or greater than the capacity of photosynthesis. In sealed cultures, such strains express the "hydrogenase pathway" and produce hydrogen upon illumination continuously, even when sulfate nutrients are abundant in the growth medium. The engineering of such *C. reinhardtii* strains permits a continuous hydrogen production process in the light as it obviates the need to perform nutrient replacement (S-deprivation) or nutrient calibration (S-titration) in order to induce the $H_2$-production activity in the green algae. When produced in large quantities, hydrogen can serve as a non-polluting and renewable fuel.

EXAMPLES

Example 1

Materials and Methods

The green alga *Chlamydomonas reinhardtii* was grown mixotrophically in a Tris-Acetate-Phosphate (TAP) medium, pH 7 (Gorman and Levin (1996)), either in liquid cultures or on 1.5% agar plates. Liquid cultures were grown on TAP or TAP with modified sulfate concentration as specified, at 25° C. in flat bottles with stirring or flasks with shaking under continuous illumination at approximately 20 μmol of photons $m^{-2}s^{-1}$. Culture density was measured by cell counting using a Neubauer ultraplane hemacytometer and a BH-2 light microscope (Olympus, Tokyo). Cells were grown to the early logarithmic phase (about $1-2 \times 10^6$ cells/ml) for all photosynthesis measurements.

Oxygen evolution activity of the cultures was measured with a Clark-type oxygen electrode illuminated with a slide projector lamp. Yellow actinic excitation was provided by a CS 3–69 Corning cut-off filter. Measurement of the light-saturation rate of photosynthesis was implemented with the oxygen electrode, beginning with the registration of dark respiration in the cell suspension, and followed by measurement of the rate of oxygen evolution at 1,500 μmol of photons $m^{-2}s^{-1}$. Registration of the rate (slope) of oxygen evolution was recorded for 5 min in each case.

Cloning of the Flanking Regions of the Insertion Site

Inverse PCR was carried out by using two sets of primers, located in the Arg7 gene coding sequence and in the pBluescript part respectively (FIG. 1). For a review of inverse PCR techniques, see Sambrook and Russell (2001) in: Molecular Cloning, A Laboratory Manual, $3^{rd}$ Edition, Protocol 14, pp. 8.81–8.85. C. reinhardtii genomic DNA was extracted using Stratagene's genomic DNA extraction kit. Ten micrograms of rep55 genomic DNA was digested with the restriction enzyme KpnI. After completion of the digestion (carried out overnight), DNA was ethanol-precipitated, resuspended in water and resolved through electrophoresis in a 0.7% agarose gel. The size of the KpnI fragment that hybridized to the pBluescript probe was previously determined by Southern blot analysis as being about 4 kb. The agarose piece containing DNA fragments of 3–5 kb was isolated and DNA was extracted using the gel extraction kit from Qiagen, Inc. (Valencia, Calif.). The gel-purified DNA was subjected to a ligation reaction, carried out in 100 μl with 400 u of DNA ligase (DNA ligase, 400 u/μl, New England Biolabs, Inc., Beverly, Mass.). The ligation reaction was carried out at room temperature for 3 h. Following inactivation of the ligase by incubation at 65° C. for 15 min, the ligation mix was purified through the column using the PCR purification kit from Qiagen, Inc. The purified DNA solution was then subjected to linearization by restriction digestion with ScaI. After 2 h of digestion, the DNA was purified again through the column as before, and used for the PCR reaction with the first set of primers, iPCR-5' and iPCR-3'. The PCR reaction was carried out in a volume of 50 μl, using a Robotic Thermal Cycler (Stratagene, La Jolla, Calif.). Settings on the apparatus were as follows: 95° C./4 min, then 35 cycles of 95° C./45 sec, 58° C./45 sec, and 72° C./1.5 min, then 10 min at 72° C. to terminate the reaction. An aliquot of the reaction product was analyzed through 0.8% agarose gel electrophoresis and the remaining reaction mix was purified through a PCR column purification kit (Qiagen, Inc.). One μl of a 50× dilution of the purified PCR product was used for the nested PCR reaction using the Nested-5' and Nested-3' primers. The settings for the nested PCR were essentially the same, except that the annealing temperature was raised to 60° C. The DNA band from the nested PCR was purified from the gel, cloned into the pGEMT vector (Stratagene) and sequenced.

Southern and Northern Blot Analyses

Southern blot analyses were carried out according to standard protocol (Sambrook et al. (1989) Molecular Cloning: A Laboratory Manual, $2^{nd}$ Ed., Cold Spring Harbor, N.Y., Cold Spring Harbor Laboratory Press). 10 μg DNA was restriction digested and size separated through electrophoresis in a 0.7% agarose gel. DNA was transferred from the agarose to a positively charged nylon membrane (PALL, BiodyneB) by capillary diffusion, using a 20× SSC buffer over a 16 h incubation. Nucleic acid hybridization reactions were carried out with the non-radioactive labeling kit Alka-Phos from Amersham-Pharmacia according to the manufacturer's specifications. Hybridization images were captured on BioMax-R film from Kodak. For Northern blot analyses, total RNA was extracted from 30 ml of cell culture with a cell density of $1-2\times10^6$ cells/ml, using the "Plant total RNA extraction kit" from Qiagen, Inc. 30 μg of total RNA was electrophoresed through a formamide/formaldehyde gel (Sambrook et al. (1989), supra). RNA was transferred onto positively charged nylon membrane (PALL, BiodyneB) overnight, through capillary transfer using 10×SSC buffer. RNA-DNA hybridization reactions were carried out with radiolabeled probes (random primed labeling kit, La Roche) according to the manufacturer's specifications.

SDS-PAGE and Western Blot Analysis

Cells were harvested by centrifugation at 3,000×g for 5 min at 4° C. For total protein extraction, pellets were lysed upon incubation with solubilization buffer containing 0.5M Tris-HCl (pH 6.8), 7% SDS, 20% glycerol, 2M urea, and 10% β-mercaptoethanol for 30 min. The crude cell extracts were then centrifuged at maximum speed in a microfuge for 3 min to remove cell debris and other insoluble matter. Chlorophyll concentration was determined by measuring the absorbance of a pigment extract obtained upon mixing 10 μl of the solubilized cells with 990 μl of 80% acetone, followed by a brief vigorous vortexing. The sample was then centrifuged at maximum speed in a microfuge for 1 min to remove undissolved matter prior to the spectrophotometry measurement for the determination of Chl (Arnon, D. (1949) Plant Physiol. 24:1–5).

Proteins were resolved by SDS-PAGE using the discontinuous buffer system of (Laemmli, U.K. (1970) Nature 227:680–685) with 12.5% acrylamide and 0.2% bis-acrylamide. The stacking gel contained 4.5% acrylamide. Electrophoresis on 0.75 mm×7 cm×8 cm slab gels was performed at 4° C. at a constant current of 10 mA for 2.5 h. After completion of the electrophoresis, proteins on the gel were either stained with Coomassie or electro-transferred onto a nitrocellulose membrane. Immunoblot analysis was carried out with specific polyclonal antibodies. Both chemiluminescence (ECL, Amersham-Pharmacia) and colorimetic (Biorad) detection methods were employed for the visualization of the antibody-antigen cross-reactions.

FIG. 14A shows wild-type and asulp29 were incubated for 24 h in media containing variable concentrations of sulfate nutrients (400, 50 and 0 μM). Total cellular protein was extracted and loaded on the gels (equal cell basis). Anti-CrcpSulP specific polyclonal antibodies were used for the Western blot analysis. Note the nearly similar levels of the CrcpSulP protein in the wild-type (400, 50 and 0 μM sulfate) and the substantially lower levels of this protein in the asulp29 transformant. FIG. 14B. Coomassie-stained SDS-PAGE profile of total protein extracts from wild-type and asulp29 that were incubated for 24 h in media containing variable concentrations of sulfate nutrients (400, 50 and 0 μM), as described above. The protein bands corresponding to the large subunit of Rubisco (RbcL) and the LHC-II are indicated. The molecular weight of the protein markers are indicated on the left-hand side. Note the declining levels of the RbcL protein as a function of the lowered sulfate concentration (400, 50 and 0 μM sulfate) in both wild-type and antisense transformant. FIG. 14C. Western blot analysis of the SDS-PAGE-resolved proteins shown in FIG. 14B.

Specific polyclonal antibodies against RbcL (large subunit of Rubisco), D1 (PS II reaction center protein) and the LHC-II (light harvesting complex of PSII) were used to detect the level of the corresponding proteins in wild-type and asulp29 antisense transfornant.

Example 2

C. reinhardtii Fractionation Studies

Cells were grown under 12 h: 12 h light/dark cycles in TAP medium to the early log phase until they reached a cell density of $1-2\times10^6$ cells/ml. Chloroplasts were isolated according to the method described by Mason et al. (1991) Plant Physiol. 97:1576–1580. Intact chloroplasts were collected from the 45 to 65% interface of Percoll centrifugation gradients. After washing twice with buffer (300 mM sorbitol, 50 mM Hepes-KOH, pH 7.5, 2 mM Na-EDTA, 1 mM $MgCl_2$), the intact chloroplasts were lysed hypotonically by suspension in a 50 mM Hepes-KOH, pH 7.5, 2 mM $MgCl_2$ buffer. The crude chloroplast membrane fraction was collected from the pellet at the bottom of the gradient. Membranes were dissolved in solubilization buffer and analyzed by SDS-PAGE.

Construction of Antisense-CrcpSulP Plasmid and Generation of Antisense Transformants The anti-SulP plasmid (pAntiSulp) employed in this work was constructed by placing a partial sequence of the CrcpSulP cDNA (from amino acid 118 to the stop codon 412) downstream of the rbcS2 promoter in reverse orientation, followed by the rbcS2 3'UTR. Both the rbcS2 promoter and the 3' UTR sequences were PCR amplified from the vector pSP124S (Stevens et al. (1996) Mol. Gen. Genet. 251: 23–30). The pAntiSulP was linearized and used in the co-transformation of Chlamydomonas reinhardtii with the pJD67 plasmid that carries the ARG7 gene in the pBluescriptII KS+ vector (Stratagene). The arginine auxotroph strain CC425 (arg7–8 mt+cw15 sr-u-2–60; Chlamydomonas Genetics center, Duke University) was co-transformed by the glass-bead method (Kindle, 1990) with the linearized pAntiSulP and pJD67. Transformants were first selected on TAP plates lacking arginine. For the selection of co-transformants, genomic DNA was prepared from arginine prototroph transformants, and used for PCR analysis with primers located at both ends of the CrcpSulP cDNA. The transformants that gave positive amplification of a DNA fragment of about 900 bp were considered positive co-transformants.

C. reinhardtii cw15 antisense transformants were also generated and isolated based on selection for zeocin resistance. In this case, the Ble gene cassette (Lumbreras et al. (1998) Plant J. 14:441–448; and Stevens et al. (1996) Mol. Gen. Genet. 251:23–30) was inserted in the upstream region of the RbcS2.pm-AntiSULP-RbcS2.3' cassette. Transformation by the glass bead method (Kindle (1990) Proc. Natl. Acad. Sci. USA 87:1228–1232) was used and the transformants were selected on TAP agar plates containing zeocin (Invitrogen) as described (Lumbreras et al. (1998) Plant J. 14:441–448; Stevens et al. (1996) Mol. Gen. Genet. 251: 23–30), except that the zeocin working concentration was 2.5 μg/ml.

Example 3

Sulfate Uptake and $^{35}$S-Pulse Labeling

Sulfate uptake experiments were carried out (Yildiz et al. (1994) Plant Physiol. 104:981–987) with the following modifications. Cells were grown under continuous illumination at approximately 50 μmol of photons $m^{-2}s^{-1}$ to a density of $1-2\times10^6$ cells/ml. Cells were pelleted and washed twice with TAP (TAP-$S_{400}$). Cells were finally suspended in the wash medium at a cell density of $0.5\times10^6$ cells/ml. Samples were placed under illumination for 24 h prior to the $^{35}$S-sulfate uptake experiments. Prior to sulfate uptake experiments, cells were centrifuged and washed twice with TAP-$S_0$ (Tris-Acetate-Phosphate medium without sulfate) and concentrated by about 10-fold to a density of $2-3\times10^7$ cells/ml in TAP-$S_0$ medium. 1.25 ml of the concentrated cell suspension was then transferred into a glass vial, stirred under continuous illumination of 200 μmol of photons $m^{-2}s^{-}$for 2 min, followed by addition of 50 μl of $^{35}$S—$Na_2SO_4$ (NEN, specific activity of 560 μCi/μmol, 1 mCi/ml, final concentration of sulfate was 72 μM). An aliquot of 100 μl was removed from the cell suspension at each time point (0, 15, 30, 45, 60 and 90 min), and transferred into a tube containing 1 ml of cold TAP medium. Cells were pelleted by centrifugation, washed twice with 1 ml of TAP, and resuspended in 50 μl of TAP, then transferred into a Nano-Sep column (PALL). Following centrifugation at 10,000 rpm for 2 min, the filter of each Nano-Sep column containing the cells was removed and the radioactivity of the sample was measured. The $^{35}$S-pulse labeling experiments were carried out essentially in the same way as described above for the sulfate uptake experiments, except that, after washing twice with TAP medium, cells were suspended in solubilization buffer and subjected to SDS-PAGE analysis.

Example 4

Construction of Plasmids

Two types of DNA constructs were created. The forward SulPcDNA(5'→3') construct is used to over-express the sulfate permease under the control of the RbcS2 promoter. The diagram below illustrates the structure of this particular construct, which is used to transform wild-type C. reinhardtii.

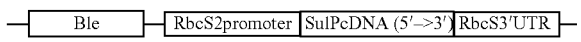

The SulPcDNA(3'→5') antisense construct is used to lower levels of expression of the endogenous sulfate permease gene.

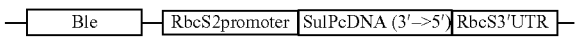

where Ble: antibiotic selection marker confers zeocin resistance to the algae; RbcS2 promoter: a strong promoter from the Rbc2 gene of C. reinhardtii; RbcS3'UTR: 3'UTR from the RbcS2 gene of C. reinhardtii serves as a transcription terminator; SulPcDNA(5'→3'): full length cDNA of CrcpSulP gene, begins with the ATG translation start codon, ends with the TGA translation stop codon; SulPcDNA (3'→5'): full length cDNA of CrcpSulP gene in the antisense direction, starts with the TGA translation stop codon, ends with the ATG translation start codon.

Example 5

Engineering the Expression Level of Sulfate Permease Gene in Chlamydomonas reinhardtii.

(i) Mutagenesis and Screening Procedures: Generate Chlamydomonas reinhardtii by transformation of a wild-type strain with plasmid DNA containing the CrcpSulP gene in the sense or antisense direction. The integration of the transformant DNA occurs almost exclusively by non-homologous recombination (Kindle (1990) *Proc. Natl. Acad. Sci. USA* 87:1228–1232). Thus, transformants carrying integrated CrcpSulP DNA at random locations in the *Chlamydomonas* nuclear genome will be generated. Transformants will be isolated as colonies on TAP in the presence of the antibiotic zeocin (5–10 μg/mL) as the selectable marker (Stevens et al. (1996) *Mol. Gen. Genet.* 251:23–30).

(ii) DNA and RNA blot analyses: Subject the genomic DNA of cells transformed with the cloned DNA to Southern blot analysis with a probe specific for the ble gene and, separately, with the SulP DNA. This comparative Southern blot analysis provides a way to visualize the number of independent insertions of plasmid/SulP genes in the *C. reinhardtii* genome (Gumpel and Purton (1994) *Trends Cell Biol.* 4:299–301). Selected transformants will be tested for mRNA levels of the SulP gene.

(iii) Functional analyses: Rates of photosynthesis and respiration of sense and antisense strains can be undertaken in order to assess the effect of transformation on the *C. reinhardtii* chloroplast ability to uptake sulfate and to sustain the function of PSII in oxygenic photosynthesis. Analysis of the photosynthetic apparatus in sense and antisense strains can be undertaken upon measurements of the concentration of PSII ($Q_A$), cytochrome b-f complex and PSI (P700) (Melis et al. (2000) *Plant Physiol.* 122:127–136). The amount of Rubisco (Zhang et al. (2002), supra) and comparative rates of D1 labeling by [$^{35}$S]sulfate (Vasilikiotis and Melis (1994) *Proc. Natl. Acad. Sci. USA* 91:7222–7226) can be undertaken in wild-type and transformants, as previously described in work from this lab. Lines in which the rate of photosynthesis is equal to or less than that of respiration can be tested for expression of the hydrogenase pathway and hydrogen production while suspended in S-replete TAP media.

This experimental protocol provides a genetic approach by which to alter the relationship between photosynthesis and respiration in the green algae and by which to probe the function of the hydrogenase pathway. A green alga transformant (sulP1) was isolated in which the P/R ratio (=1.1:1) is substantially lower than that of the wild-type (=4:1). The sulP1 is be used in a *Chlamydomonas/Rhodobacter* co-cultivation system for enhanced hydrogen production.

A green alga (*Chlamydomonas/Rhodobacter*) hybrid system may have failed in the past due to the great capacity of green algae to produce $O_2$ photosynthetically (P/R=4:1 ratio). Oxygen is a powerful positive suppressor of the [Fe]-hydrogenase and nitrogenase/hydrogenase gene expression, and inhibitor of the function of the respective enzymes (Sasikala and Ramana (1995) *Adv. Appl. Microbiol.* 41:211–295; and Ogata et al. (2001) *Proc. JSWE* 35:540). However, availability of the sulP1 strain (P/R=1.1:1 ratio) alleviates this problem because it removes the dominance of the oxygen-producing reactions without impairing oxygenic photosynthesis. Thus, the existence of sulP1 allows for the co-cultivation of the two organisms under anaerobic conditions. Anaerobiosis is necessary and sufficient to induce the hydrogen production activities in both of these organisms.

Example 6

Cultivation of the green alga *Chlamydomonas reinhardtii* and the anoxygenic photosynthetic bacterium *Rhodobacter sphaeroides* autotrophically/photoheterotrophically according to established protocols (Harris (1989) in: The *Chlamydomonas* Sourcebook, Academic Press, Inc., San Diego, p. 780; and Rocha et al. (2001), supra). Initially, cultures are inoculated with *C. reinhardtii* and permitted to grow phototrophically until a significant biomass has accumulated (about $3 \times 10^6$ cells/mL). At that stage, the growth medium will be supplemented with the organic nutrients needed for the photoheterotrophic growth of *R. sphaeroides*. Under these photoheterotrophic growth conditions, *C. reinhardtii* lowers its operational P/R ratio (Polle et al. (2000) *Planta* 211(3):335–344; and Zhang et al. (2002), supra). In the sulP1, such photoheterotrophic growth conditions cause the P/R ratio to drop below unity, resulting in anaerobiosis of the culture. Anaerobiosis, once it is established in the growth medium, permits inoculation and co-cultivation of *R. sphaeroides* under the same conditions (Miura et al. (1992) *Bioshi. Biotech. Biochem.* 56:751–754). *C. reinhardtii* and *R. sphaeroides* in the growth medium of the latter co-exist and produce biomass and hydrogen in a facultative process in which *R. sphaeroides* benefits from the small organic acids exuded by the *C. reinhardtii* cells (FIG. 20).

The invention optimizes the process by measuring physiological and biochemical parameters of the cells in the integrated culture. The following parameters are measured:
a. Rates of growth;
b. Rates of gas production;
c. Rates of photosynthesis and respiration;
d. Absorbance spectra and densities on a per cell basis;
e. Cellular metabolite content (starch, protein, lipid per cell); and
f. Duration of hydrogen production of the hybrid culture as compared to single cell cultures.

On the basis of these measurements, necessary and sufficient mix ratios are defined to permit a mixture of the two organisms that perform photosynthesis and hydrogen production under negative oxygen exchange rates (i.e., rates of respiration greater than rates of oxygenic photosynthesis). Protocols for the regulation of the *Chlamydomonas/Rhodobacter* mix ratio can be developed by following protocol described here.

Individually, under optimal conditions and on the basis of current technology, *C. reinhardtii* and *R. sphaeroides* will produce 2.5 and 40–50 mL hydrogen per L culture per h, respectively. During the course of photosynthesis and hydrogen production, *R. sphaeroides* consumes substantial amounts of small organic molecules (such as glycolate, acetate, lactate, malate, etc.). Once these metabolites are exhausted, hydrogen production stops. During the course of photoheterotrophic growth under anaerobic conditions and hydrogen production, *C. reinhardtii* catabolism of endogenous substrate results in the generation and release of such small organic acids, which are exuded from the cell.

An advantage of this two-organism hybrid system is that *C. reinhardtii* (strain sulP1) generates biomass and small organic acid molecules in the medium. *R. sphaeroides* would then benefit from the supply of these small organic molecules for an extended period of hydrogen production, resulting is substantially greater yields and lower costs. This provides a hydrogen production hybrid system in which the duration and yield of the integrated process far exceeds that of the individual components.

Example 7

ARS Activity Assay

Cells were transferred from TAP-agar plates into a 96-well microtiter plate containing liquid TAP medium, and incubated for 24 h under light. An aliquot of cell suspension (38 μl) was then transferred into another microtiter plate containing 62 μl of TAP-S$_0$ medium per well, so that the final concentration of sulfate in the medium was approximately 150 μM. The microtiter plate was placed under continuous illumination for 24 h prior to the detection of the ARS activity. To detect ARS activity, 10 μl of 10 mM 5-bromo-4-chloro-3-indolyl sulfate potassium salt (Product No. B1379, Sigma-Aldrich) in 10 mM Tris-HCl, pH 7.5, was added to the cell suspension. The color of the mixture was allowed to develop over a 3–4 h period, followed by scanning of the microtiter plate for the recording of the resulting images.

Results of an assay are shown in FIGS. 16A and 16B. FIG. 16A shows wild-type and 47 antisense transformants were tested for their ARS activity induction when suspended in normal TAP medium (400 μM sulfate). The wild-type control strain is shown in the upper left of the liquid culture multi-well plate, indicated by "•". Strains that showed ARS activity, as judged by the appearance of blue color in the 96-well plate, are indicated by "*". A 5% or more difference in color is indicative of a positive result for downregulation of sulfate uptake. FIG. 16B shows a replica plate of the above with strains suspended in a TAP medium containing 150 μM sulfate. Other conditions are identical to FIG. 16A.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of hydrogen gas generation, comprising the steps of:
   culturing genetically modified algae under illuminated conditions wherein sulfate permease expression of the algae, comprising SEQ ID NO:1, is reduced relative to unmodified wild-type algae wherein the algae is genetically modified to disrupt expression of chloroplast sulfate permease gene CrcpSulP comprising SEQ ID NO:2 by insertion of an antisense sequence which hybridizes under high stringency conditions, wherein said conditions are hybridization and/or washing conditions at 68° C. in 0.2. times. SSC or at 42° C. in 50% foramide, 4. times SSC to a portion of SEQ ID NO:2 mRNA;
   sealing the algae culture from atmospheric oxygen; and collecting hydrogen gas evolved.

2. A method of hydrogen gas generation, comprising the steps of:
   culturing genetically modified algae under illuminated conditions wherein sulfate permease expression of the algae is reduced relative to unmodified wild-type algae wherein the algae is a green algae and the algae comprises a genome which is artificially engineered to reduce sulfate permease expression comprising SEQ ID NO:1 relative to a wild-type algae by insertion of an antisense sequence which hybridizes under high stringency conditions, wherein said conditions are hybridization and/or washing conditions at 68° C. 0.2. times. SSC or at 42° C. in 50% foramide, 4. times. SSC to a portion of SEQ ID NO:2 mRNA.

3. The method of claim 2, wherein the algae is a unicellular, photosynthetic algae.

4. A method of hydrogen gas generation, comprising the steps of:
   culturing algae under illuminated conditions, wherein the algae is an isolated strain with downregulated expression of sulfate permease with 50% or less expression of chloroplast sulfate permease gene CrcpSulP comprising SEQ ID NO:2 by insertion of an antisense sequence which hybridizes under high stringency conditions, wherein said conditions are hybridization and/or washing conditions at 68° C. in 0.2. times. SSC or at 42° C. in 50% foramide, 4. times. SSC to a portion of SEQ ID NO:2 mRNA;
   sealing the algae culture from atmospheric oxygen; and collecting hydrogen gas evolved.

5. A method of hydrogen gas generation, comprising the steps of:
    culturing genetically modified algae under illuminated conditions wherein sulfate permease expression of the algae, comprising SEQ ID NO:1, is reduced relative to unmodified wild-type algae wherein the algae is genetically modified to disrupt expression of chloroplast sulfate permease gene CrcpSulP comprising SEQ ID NO:3 by insertion of an antisense sequence which hybridizes under high stringency conditions, wherein said conditions are hybridization and/or washing conditions at 68° C. in 0.2. times. SSC or at 42° C. in 50% foramide, 4. times. SSC to a portion of SEQ ID NO:3 mRNA;
    sealing the algae culture from atmospheric oxygen; and collecting hydrogen gas evolved.

* * * * *